(12) United States Patent
Echigo et al.

(10) Patent No.: US 9,540,339 B2
(45) Date of Patent: Jan. 10, 2017

(54) RESIST COMPOSITION, METHOD FOR FORMING RESIST PATTERN, POLYPHENOLIC COMPOUND FOR USE IN THE COMPOSITION, AND ALCOHOLIC COMPOUND THAT CAN BE DERIVED THEREFROM

(71) Applicant: Mitsubishi Gas Chemical Company, Inc., Tokyo (JP)

(72) Inventors: Masatoshi Echigo, Hiratsuka (JP); Masako Yamakawa, Hiratsuka (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/005,177

(22) Filed: Jan. 25, 2016

(65) Prior Publication Data

US 2016/0176840 A1   Jun. 23, 2016

Related U.S. Application Data

(62) Division of application No. 14/238,402, filed as application No. PCT/JP2012/070304 on Aug. 9, 2012.

(30) Foreign Application Priority Data

Aug. 12, 2011  (JP) .................... 2011-176923
Sep. 15, 2011  (JP) .................... 2011-201757
Sep. 30, 2011  (JP) .................... 2011-218626

(51) Int. Cl.
| C07D 311/78 | (2006.01) |
| C07C 39/225 | (2006.01) |
| C07D 311/96 | (2006.01) |
| C07C 37/20 | (2006.01) |
| G03F 7/031 | (2006.01) |
| G03F 7/038 | (2006.01) |
| C07C 39/14 | (2006.01) |
| C07C 39/17 | (2006.01) |
| G03F 7/004 | (2006.01) |
| G03F 7/20 | (2006.01) |
| G03F 7/32 | (2006.01) |

(52) U.S. Cl.
CPC ............ *C07D 311/78* (2013.01); *C07C 37/20* (2013.01); *C07C 39/14* (2013.01); *C07C 39/17* (2013.01); *C07C 39/225* (2013.01); *C07D 311/96* (2013.01); *G03F 7/0045* (2013.01); *G03F 7/031* (2013.01); *G03F 7/038* (2013.01); *G03F 7/20* (2013.01); *G03F 7/32* (2013.01); *C07C 2101/10* (2013.01); *C07C 2101/14* (2013.01)

(58) Field of Classification Search
None
See application file for complete search history.

(56) References Cited

U.S. PATENT DOCUMENTS 6,784,228 B2   8/2004  Ogura
2007/0232839 A1  10/2007  Yoshitomo et al.
2008/0153031 A1   6/2008  Echigo et al.
2010/0047709 A1   2/2010  Echigo et al.
2010/0099044 A1   4/2010  Hatakeyama et al.
2010/0104977 A1   4/2010  Hatakeyama et al.
2010/0285407 A1  11/2010  Ogihara et al.

FOREIGN PATENT DOCUMENTS

| CN | 1414031 A | 4/2003 |
| EP | 1275673 A2 | 1/2003 |
| JP | H04-217675 A | 8/1992 |
| JP | 2001-042525 A | 2/2001 |
| JP | 2005-326838 A | 11/2005 |
| JP | 2006-036648 A | 2/2006 |
| JP | 2006-098869 A | 4/2006 |
| JP | 2006-113136 A | 4/2006 |
| JP | 2006-213634 A | 8/2006 |
| JP | 2007199653 A * | 8/2007 |
| JP | 2007-326847 A | 12/2007 |
| JP | 2008-145539 A | 6/2008 |
| JP | 2008-239868 A | 10/2008 |
| JP | 2009-155256 A | 7/2009 |
| JP | 2009-173623 A | 8/2009 |
| JP | 2009-300978 A | 12/2009 |
| JP | 2010-160189 A | 7/2010 |
| JP | 2010-235643 A | 10/2010 |
| JP | 2011-068624 A | 4/2011 |
| JP | 2011-105887 A | 6/2011 |
| WO | 2011034062 A1 | 3/2011 |

OTHER PUBLICATIONS

Ohishi, Takeshi. Tetrahedron Letters 42 (2001) 2493-2496.*
T. Nakayama, M. Nomura, K. Haga, M. Ueda, Bull Chem. Soc. Jpn., 71, 2979 (1998).
International Search Report dated Oct. 23, 2012, issued in International Application No. PCT/JP2012/070304.
Written Opinion of the International Searching Authority issued in International Application No. PCT/JP2012/070304 (including translation), Dated Oct. 23, 2012.
Okan Sirkecioglu et al., A novel synthesis of 14-(hydroxymethylalkyl) derivatives of dibenzoxanthenes and 3, 3-dimethyl-4-(2-hydroxy-1-naphthyl) benzo [f] chroman', Journal of Heterocyclic Chemistry, vol. 35, No. 2, Mar. 1, 1998, pp. 457-460.
Ghodratbeigi et al., Design, modeling and synthesis of molecular tweezers with self-assembly properties, Journal of Molecular Structure, 990:140-151 (2011).
Brecher, Jonathan, Graphical Representation Standards for Chemical Structure Diagrams, Pure Appl. Chem., 2008, pp. 277-410, vol. 80, No. 2, Cambridge, Massachusetts.

* cited by examiner

Primary Examiner — Golam M M Shameem
Assistant Examiner — Laura Daniel
(74) *Attorney, Agent, or Firm* — Fitch, Even, Tabin & Flannery LLP

(57) ABSTRACT

A resist composition containing a compound represented by the general formula (1) or (2), a method for forming a resist pattern using the composition, a polyphenolic compound for use in the composition, and an alcoholic compound that can be derived therefrom are described.

3 Claims, No Drawings

RESIST COMPOSITION, METHOD FOR FORMING RESIST PATTERN, POLYPHENOLIC COMPOUND FOR USE IN THE COMPOSITION, AND ALCOHOLIC COMPOUND THAT CAN BE DERIVED THEREFROM

CROSS-REFERENCE TO RELATED APPLICATIONS

This Application is a divisional application of U.S. application Ser. No. 14/238,402, filed Feb. 11, 2014, which is the U.S. National Stage Application filed under 35 U.S.C. §371 of International Application PCT/JP2012/070304, filed Aug. 9, 2012, designating the United States, and claims priority from Japanese Patent Application 2011-176923, filed Aug. 12, 2011, Japanese Patent Application 2011-201757, filed Sep. 15, 2011, and Japanese Patent Application 2011-218626, filed Sep. 30, 2011, the complete disclosures of which are hereby incorporated herein by reference in their entirety for all purposes.

TECHNICAL FIELD

The present invention relates to a resist composition and a method for forming a resist pattern using the composition.

The present invention also relates to a polyphenolic compound that can be used in the resist composition, etc. and an alcoholic compound that can be derived therefrom.

BACKGROUND ART

Conventional typical resist materials are polymer based materials capable of forming amorphous thin films. For example, a line pattern of about 45 to 100 nm is formed by irradiating a resist thin film made by coating a substrate with a solution of a polymer resist material such as polymethyl methacrylate, polyhydroxy styrene with an acid dissociation reactive group, or polyalkyl methacrylate with ultraviolet, far ultraviolet, electron beam, extreme ultraviolet (EUV), and X-ray or the like.

However, because polymer based resists have a molecular weight as large as about 10,000 to 100,000 and also wide molecular weight distribution, in lithography using a polymer based resist, roughness occurs on a fine pattern surface; the pattern dimension becomes difficult to be controlled; and the yield decreases. Therefore, there is a limitation in miniaturization with lithography using a conventional polymer based resist material. In order to make a finer pattern, various low molecular weight resist materials have been proposed.

For example, an alkaline development type negative type radiation-sensitive composition (see Patent Literatures 1 and 2) using a low molecular weight polynuclear polyphenolic compound as a main component has been suggested. As a candidate of a low molecular weight resist material having high heat resistance, an alkaline development type, negative type radiation-sensitive composition (see Patent Literature 3 and Non Patent Literature 1) using a low molecular weight cyclic polyphenolic compound as a main component has also been suggested.

As a base compound of a resist material, a polyphenolic compound is known to be useful in imparting high heat resistance and improving the resolution or roughness of a resist pattern, in spite of its low molecular weight (see Non Patent Literature 2). Also, various polyphenols are used as raw materials for thermoplastic resins such as polycarbonate and polyarylate, raw materials for thermosetting resins such as epoxy resins, curing agents, modifiers, and the like (see Patent Literatures 4 and 5).

As resin raw materials or resin curing agents, fluorene compounds having a cardo structure are known to have various characteristics (optical characteristics, heat resistance, water resistance, moisture resistance, chemical resistance, electrical characteristics, mechanical characteristics, dimensional stability, etc.) improved by substitution with polyhydric phenol or the like (see Patent Literatures 6 to 9).

CITATION LIST

Patent Literature

Patent Literature 1: Japanese Patent Application Laid-Open No. 2005-326838
Patent Literature 2: Japanese Patent Application Laid-Open No. 2008-145539
Patent Literature 3: Japanese Patent Application Laid-Open No. 2009-173623
Patent Literature 4: Japanese Patent Application Laid-Open No. 2006-213634
Patent Literature 5: Japanese Patent Application Laid-Open No. 2007-326847
Patent Literature 6: Japanese Patent Application Laid-Open No. 2006-36648
Patent Literature 7: Japanese Patent Application Laid-Open No. 2009-155256
Patent Literature 8: Japanese Patent Application Laid-Open No. 2011-68624
Patent Literature 9: Japanese Patent Application Laid-Open No. 2011-105887

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazaki et al., "Innovation of Photoresist Material Development", CMC Publishing Co., Ltd., September 2009, p. 211-259

SUMMARY OF INVENTION

Technical Problem

However, the compositions of Patent Literatures 1 and 2 have the disadvantages that the heat resistance is not sufficient and the shape of the resulting resist pattern becomes poor. The compositions of Patent Literature 3 and Non Patent Literature 1 have problems such as low solubility in a safe solvent used in a semiconductor production process, low sensitivity, and the poor shape of the resulting resist pattern. Improvement in such low molecular weight resist materials is desired.

Patent Literatures 4 and 5 and Non Patent Literature 2 make no mention about solubility. Still, the heat resistance of the compounds described therein is not sufficient. Further improvement is desired in terms of characteristics such as heat resistance, water resistance, chemical resistance, electrical characteristics, and mechanical characteristics.

The characteristics such as heat resistance of the alcoholic compounds of Patent Literatures 6 to 9 are not sufficient. Alcoholic compounds improved in heat resistance are further desired.

An object of the present invention is to provide a resist composition which is excellent in heat resistance, has high solubility in a safe solvent, has high sensitivity, and can impart a good shape to a resist pattern, and a method for forming a resist pattern using the resist composition.

Another object of the present invention is to provide a polyphenolic compound which is excellent in heat resistance and has high solubility in a safe solvent.

A further object of the present invention is to provide an alcoholic compound which has high heat resistance.

Solution to Problem

The inventors have, as a result of devoted examinations to solve the above problems, found out that by having a compound having a specific structure, a resist composition is excellent in heat resistance, has high solubility in a safe solvent, has high sensitivity, and can impart a good shape to a resist pattern, and reached the present invention.

More specifically, the present invention is as follows.
1. A resist composition comprising a compound represented by the general formula (1) or (2):

[Chemical Formula 1]

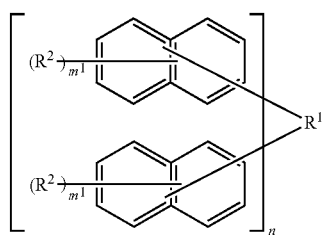

(1)

[Chemical Formula 2]

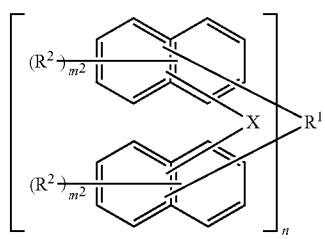

(2)

wherein $R^1$ are each independently a single bond or a 2n-valent hydrocarbon group having 1 to 30 carbon atoms wherein the hydrocarbon group may have a cyclic hydrocarbon group, a double bond, a heteroatom, or an aromatic group having 6 to 30 carbon atoms; $R^2$ are each independently a hydrogen atom, a halogen atom, a linear, branched, or cyclic alkyl group having 1 to 10 carbon atoms, an aryl group having 6 to 10 carbon atoms, an alkenyl group having 2 to 10 carbon atoms, or a hydroxyl group and may be the same or different on the same naphthalene ring; at least one of $R^2$ is a hydroxyl group; n is an integer of 1 to 4; the structural formulas of the repeating units in the formulas (1) and (2) may be the same or different; in the general formula (1), $m^1$ are each independently an integer of 1 to 7; and in the general formula (2), X are each independently an oxygen atom or a sulfur atom, and $m^2$ are each independently an integer of 1 to 6.
2. The resist composition according to the above item 1, wherein the general formula (1) is the general formula (1-1), and the general formula (2) is the general formula (2-1):

[Chemical Formula 3]

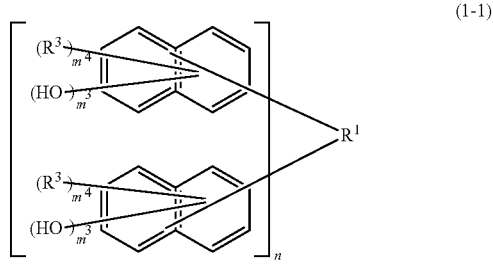

(1-1)

[Chemical Formula 4]

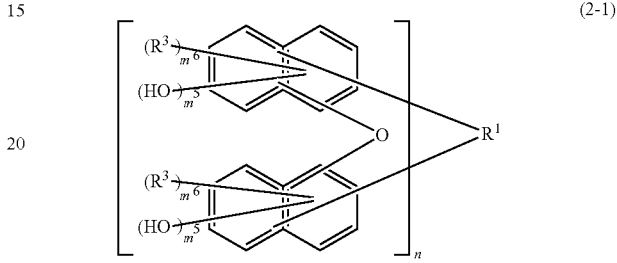

(2-1)

wherein $R^1$ and n are the same as in the above formula (1); $R^3$ are each independently a hydrogen atom, a linear, branched, or cyclic alkyl group having 1 to 10 carbon atoms, an aryl group having 6 to 10 carbon atoms, or an alkenyl group having 2 to 10 carbon atoms and may be the same or different on the same naphthalene ring; the structural formulas of the repeating units in the formulas (1) and (2) may be the same or different; n is an integer of 1 to 4; in the general formula (1-1), $m^3$ are each independently an integer of 1 to 7, $m^4$ are each independently an integer of 0 to 6, and $m^3+m^4$ is an integer of 1 to 7; and in the general formula (2-1), $m^5$ are each independently an integer of 1 to 6, $m^6$ are each independently an integer of 0 to 5, and $m^5+m^6$ is an integer of 1 to 6.
3. The resist composition according to the above item 1, wherein the general formula (1) is the general formula (1-2), and the general formula (2) is the general formula (2-2):

[Chemical Formula 5]

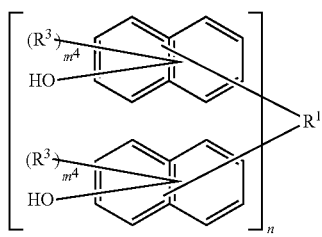

(1-2)

[Chemical Formula 6]

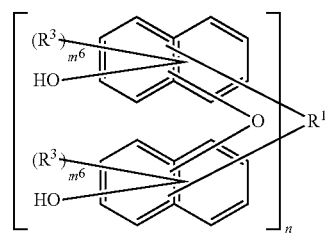

(2-2)

wherein $R^1$, $R^3$, n, $m^4$, $m^6$, and the like are the same as above.

4. The resist composition according to any one of the above items 1 to 3, further comprising a solvent.

5. The resist composition according to any one of the above items 1 to 4, further comprising an acid generating agent.

6. The resist composition according to any one of the above items 1 to 5, further comprising an acid crosslinking agent.

7. A method for forming a resist pattern, comprising the steps of:

coating a substrate with the resist composition according to any one of the above items 1 to 6, thereby forming a resist film;

exposing the formed resist film; and developing the exposed resist film.

The inventor has also, as a result of devoted examinations to solve the above problems, found out that the problems can be solved by means of a novel polyphenolic compound having a specific structure and a composition comprising the compound, and reached the present invention.

More specifically, the present invention is as follows.

8. The resist composition according to any one of the above items 1 and 4 to 6, wherein the compound represented by the general formula (1) is a polyphenolic compound represented by the general formula (3), and the compound represented by the general formula (2) is a polyphenolic compound represented by the general formula (4):

[Chemical Formula 7]

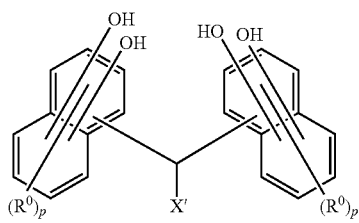

(3)

[Chemical Formula 8]

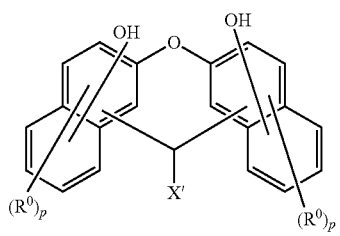

(4)

wherein X' are each independently a hydrogen atom or a monovalent substituent having 1 to 18 carbon atoms; $R^0$ are each independently an alkyl group having 1 to 4 carbon atoms or a halogen atom and may be the same or different on the same naphthalene ring; and p is an integer of 0 to 5.

9. A polyphenolic compound represented by the above general formula (3) or (4).

10. The resist composition according to the above item 8, wherein the compound represented by the general formula (3) is a polyphenolic compound represented by the general formula (30), and the compound represented by the general formula (4) is a polyphenolic compound represented by the general formula (40):

[Chemical Formula 9]

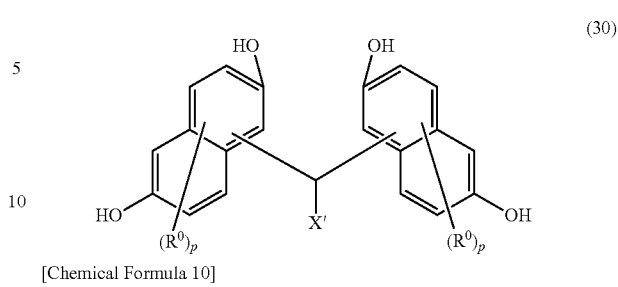

(30)

[Chemical Formula 10]

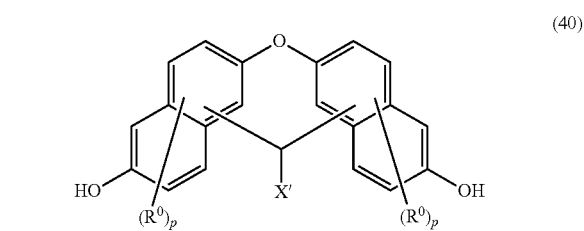

(40)

wherein X' are each independently a hydrogen atom or a monovalent substituent having 1 to 18 carbon atoms; $R^0$ are each independently an alkyl group having 1 to 4 carbon atoms or a halogen atom and may be the same or different on the same naphthalene ring; and p is an integer of 0 to 5.

11. The polyphenolic compound according to the above item 9, wherein the general formula (3) is the general formula (30), and the general formula (4) is the general formula (40).

12. A method for producing the polyphenolic compound according to the above item 9, comprising reacting a compound represented by the general formula (5) with an aldehyde having 1 to 19 carbon atoms in the presence of an acid catalyst:

[Chemical Formula 11]

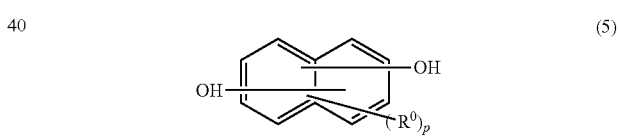

(5)

wherein $R^0$ and p are the same as above.

13. The method for producing the polyphenolic compound according to the above item 10, comprising reacting a compound represented by the general formula (50) with an aldehyde having 1 to 19 carbon atoms in the presence of an acid catalyst:

[Chemical Formula 12]

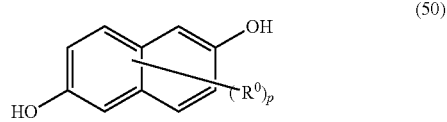

(50)

wherein $R^0$ and p are the same as above.

The inventor has further, as a result of devoted examinations to solve the above problems, found out that the problems can be solved by means of a novel alcoholic compound having a specific structure, and reached the present invention.

More specifically, the present invention is as follows.
14. A method for producing an alcoholic compound represented by the general formula (6) or (7), comprising reacting the polyphenolic compound according to the above item 9 with an alkylene oxide introducing agent in the presence of a basic catalyst:

[Chemical Formula 13]

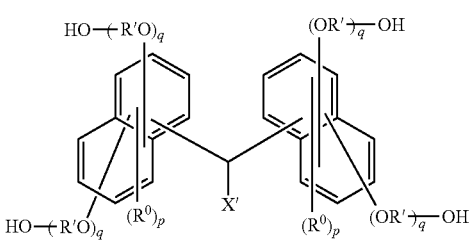

(6)

[Chemical Formula 14]

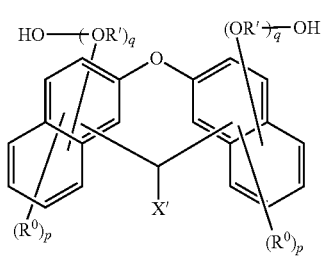

(7)

wherein X', R', R⁰, q, and p are the same as above.
15. An alcoholic compound represented by the above general formula (6) or (7).
16. A method for producing an alcoholic compound represented by the general formula (60) or (70), comprising reacting the polyphenolic compound according to the above item 10 with an alkylene oxide introducing agent in the presence of a basic catalyst:

[Chemical Formula 15]

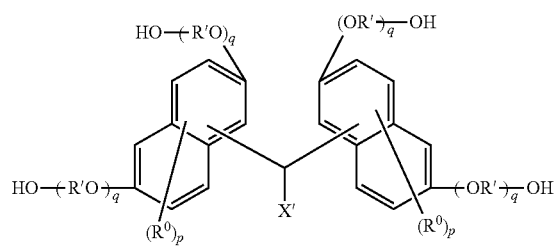

(60)

[Chemical Formula 16]

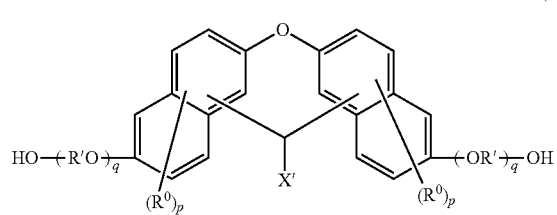

(70)

wherein X', R', R⁰, q, and p are the same as above.

17. The alcoholic compound according to the above item 15, wherein the general formula (6) is the general formula (60), and the general formula (7) is the general formula (70).

Advantageous Effects of Invention

The present invention can provide a resist composition which is excellent in heat resistance, has high solubility in a safe solvent, has high sensitivity, and can impart a good shape to a resist pattern, and a method for forming a resist pattern using the composition.

The present invention can also provide a polyphenolic compound which is excellent in heat resistance and has high solubility in a safe solvent.

The present invention can further provide an alcoholic compound which has high heat resistance.

DESCRIPTION OF EMBODIMENTS

Hereinafter, an embodiment of the present invention will be described (hereinafter, referred to as "present embodiment"). The present embodiment is given in order to illustrate the present invention. The present invention is not limited to only the present embodiment.

[Resist Composition]

The resist composition of the present embodiment contains a compound represented by the above general formula (1) or (2).

Composition of First Embodiment

According to the first embodiment, the resist composition of the present embodiment contains a compound represented by the following formula (1):

[Chemical Formula 17]

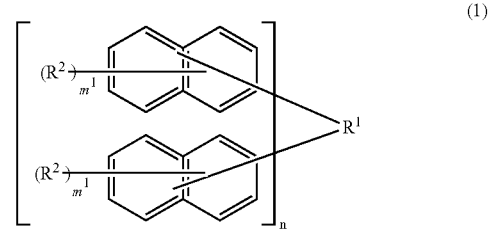

(1)

The chemical structure of the compound of the present embodiment can be determined by $^1$H-NMR analysis.

The composition of the present embodiment has a naphthalene skeleton as shown in the above formula (1) and is therefore excellent in heat resistance.

In the formula (1), the structural formulas of the repeating units may be the same or different, and n is an integer of 1 to 4. In terms of resist characteristics such as heat resistance, resolution, and roughness, n is preferably 1 to 3.

Although the compound of the present embodiment is not a polymer, the structure of the moiety [ ] bonded to R$^1$ in the above formula (1) is referred to as the structural formula of a repeating unit (hereinafter, the same holds true for the formula (2)) for the sake of convenience.

In the above formula (1), R$^1$ are each independently a single bond or a 2n-valent hydrocarbon group having 1 to 30 carbon atoms (hereinafter, may be referred to as "C1-30") wherein the hydrocarbon group may have a cyclic hydrocarbon group, a double bond, a heteroatom, or a C6-30 aromatic group.

The above 2n-valent hydrocarbon group refers to a C1-30 alkylene group (n=1), a C1-30 alkanetetrayl group (n=2), a C2-30 alkanehexayl group (n=3), or a C3-30 alkaneoctayl group (n=4). Examples of the 2n-valent hydrocarbon group include ones having a linear, branched or cyclic structure.

The above 2n-valent hydrocarbon group may have a cyclic hydrocarbon group, a double bond, a heteroatom, or a C6-30 aromatic group. Herein, the cyclic hydrocarbon group also includes bridged cyclic hydrocarbon groups.

$R^1$ preferably has a condensed polycyclic aromatic group (particularly, a bicyclic to tetracyclic condensed ring structure) in terms of heat resistance and preferably has a polyphenyl group such as a biphenyl group in terms of solubility in a safe solvent and heat resistance.

$R^2$ are each independently a hydrogen atom, a halogen atom, a C1-10 linear, branched, or cyclic alkyl group, a C6-10 aryl group, a C2-10 alkenyl group, or a hydroxyl group and may be the same or different on the same naphthalene ring, and $m^1$ are each independently an integer of 1 to 7.

In terms of prevention of equipment contamination upon resist film exposure, $R^2$ is preferably a hydrogen atom, a C1-10 linear, branched, or cyclic alkyl group, a C6-10 aryl group, a C2-10 alkenyl group, or a hydroxyl group.

For the resist composition of the present embodiment, in terms of heat resistance and solubility in a safe solvent, it is required that at least one of $R^2$ in the formula (1) should be a hydroxyl group.

By virtue of the above structural features, the compound represented by the above formula (1) has high heat resistance attributed to its rigidity, in spite of its low molecular weight, and may be used even under high temperature baking conditions. Since the compound represented by the formula (1) has a low molecular weight and may be baked at a high temperature, the compound is highly sensitive and, in addition, can impart a good shape to a resist pattern.

In the present embodiment, in terms of solubility in a safe solvent and resist pattern characteristics, the compound represented by the above formula (1) is preferably a compound represented by the general formula (1-1) having one or more phenolic hydroxyl groups per one naphthalene group:

[Chemical Formula 18]

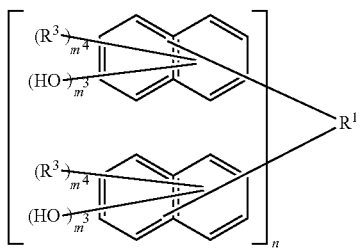

(1-1)

wherein $R^1$ is the same as above; $R^3$ are each independently a hydrogen atom, a C1-10 linear, branched, or cyclic alkyl group, a C6-10 aryl group, or a C2-10 alkenyl group; $m^3$ are each independently an integer of 1 to 7; $m^4$ are each independently an integer of 0 to 6; $m^3+m^4$ is an integer of 1 to 7; and n is an integer of 1 to 4.

In the present embodiment, in terms of sensitivity as a resist composition, the compound represented by the above formula (1-1) is preferably a compound represented by the formula (1-2):

[Chemical Formula 19]

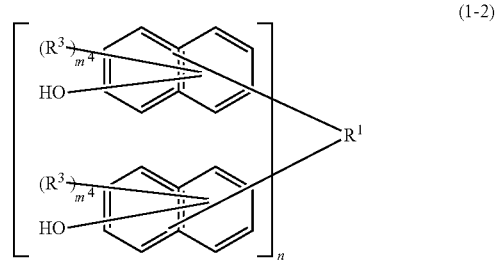

(1-2)

wherein $R^1$, $R^3$, $m^4$, and n are the same as in the above formula (1-1).

In terms of solubility and sensitivity as a resist composition, $m^3$ in the above formula (1-1) is preferably 2.

In the present embodiment, in terms of resist characteristics such as heat resistance, sensitivity, resolution, and roughness, the compound represented by the above formula (1-1) is preferably a compound represented by the above formula (1-1) wherein n is 1.

In the present embodiment, in terms of solubility, the compound represented by the above formula (1-1) is more preferably a compound represented by the general formula (1-3):

[Chemical Formula 20]

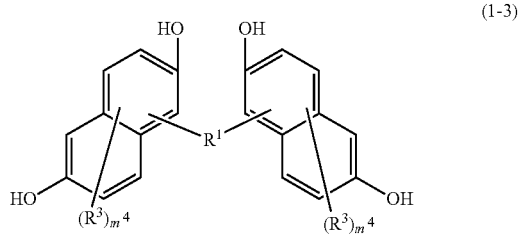

(1-3)

wherein $R^1$, $R^3$, and $m^4$ are the same as in the above general formula (1-1).

Specific examples of the compound represented by the above formula (1) can include, but not limited to, the followings:

[Chemical Formula 21]

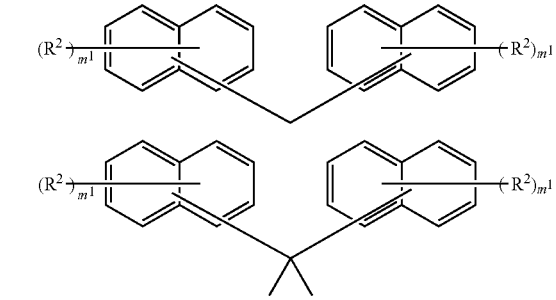

-continued
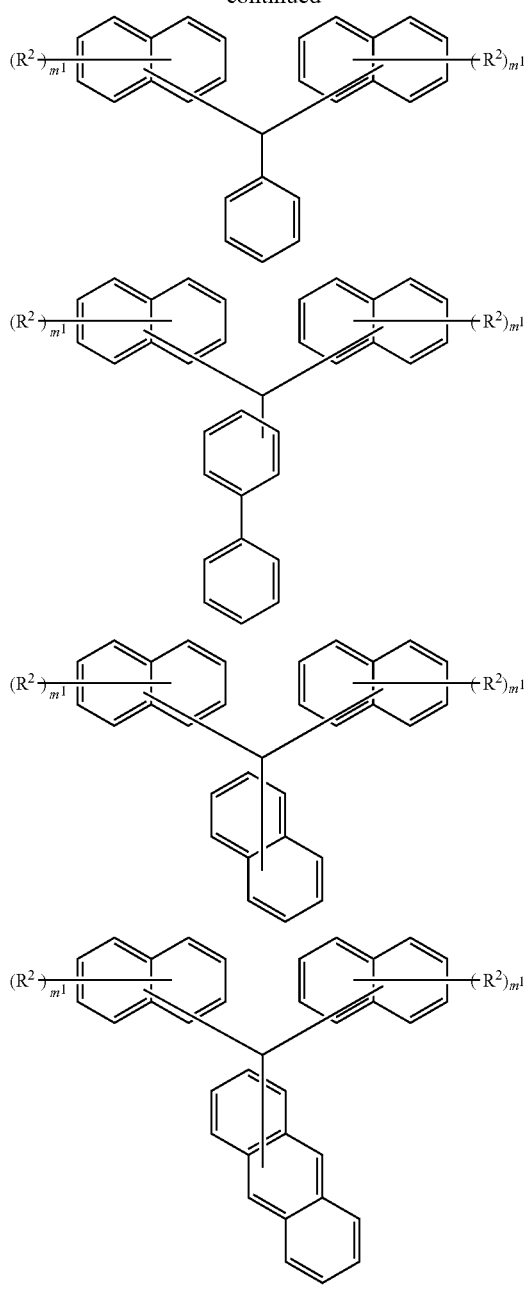
[Chemical Formula 22]
-continued
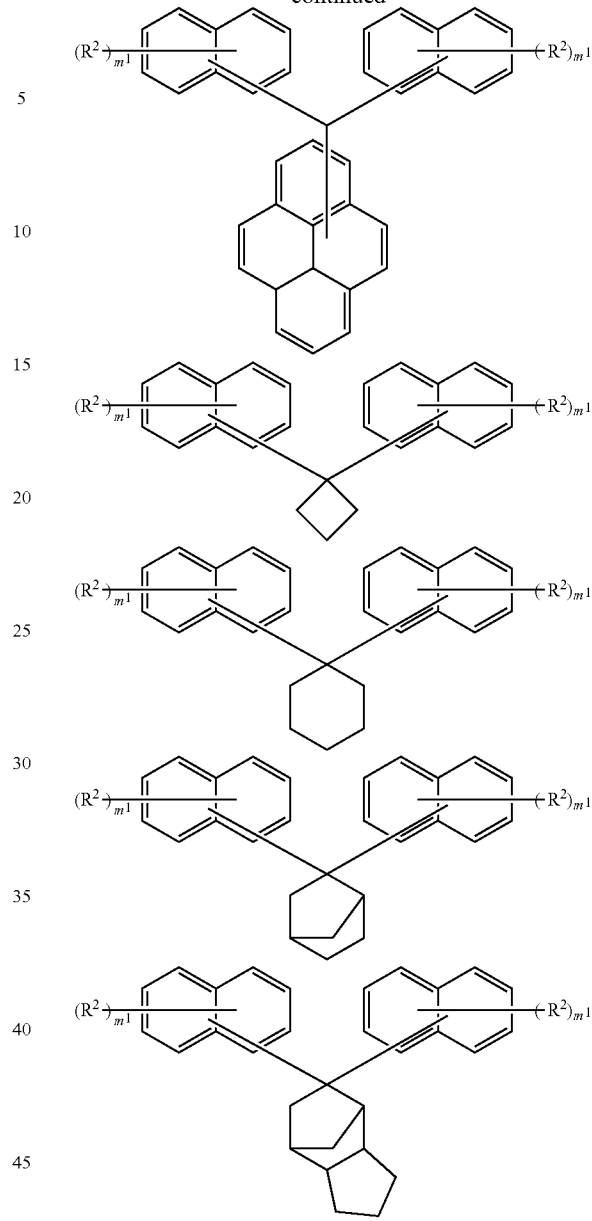
[Chemical Formula 23]
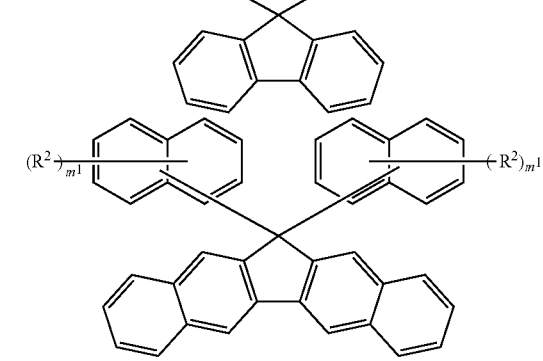

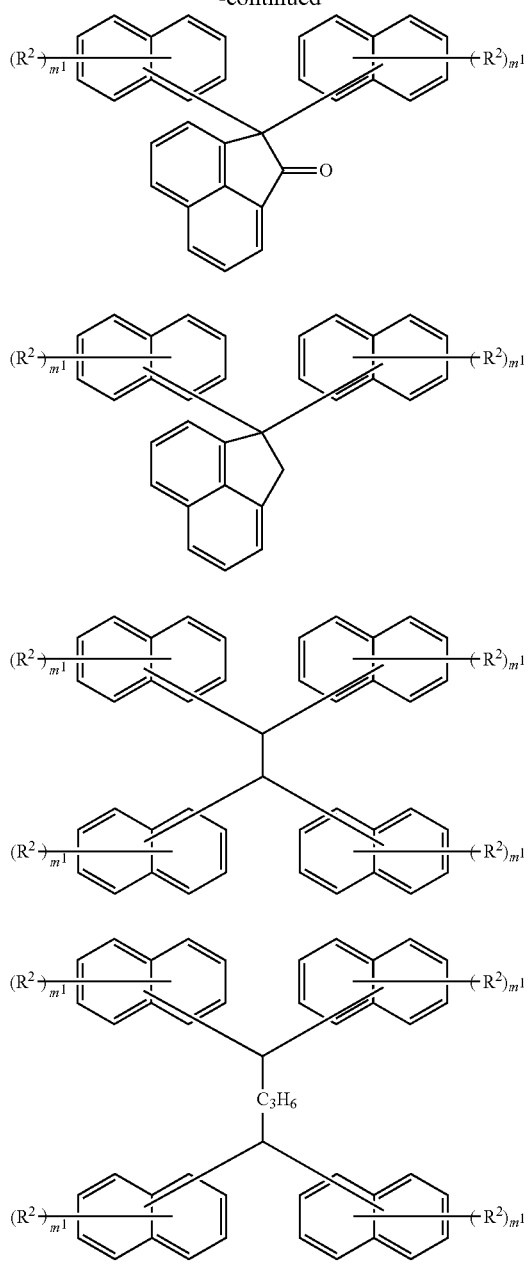
[Chemical Formula 24]
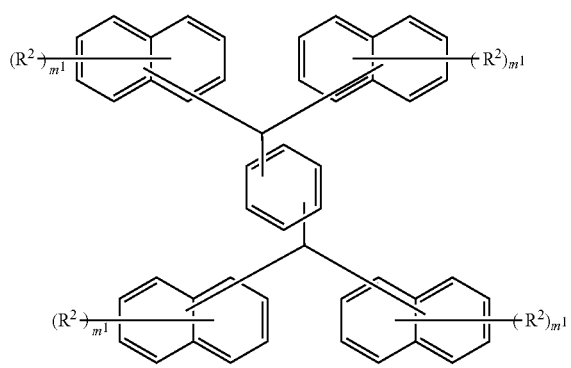
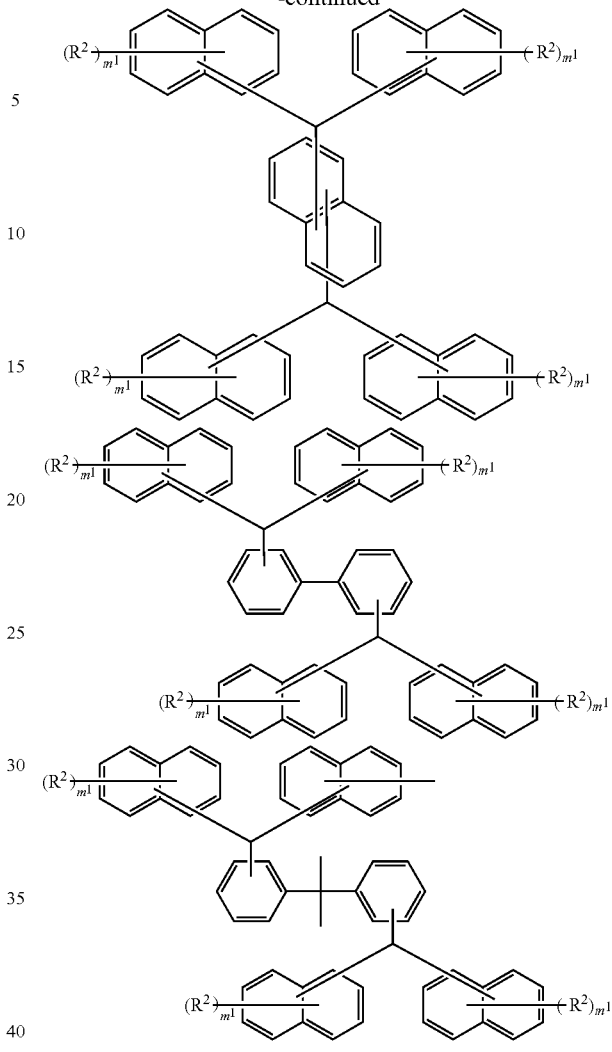
[Chemical Formula 25]
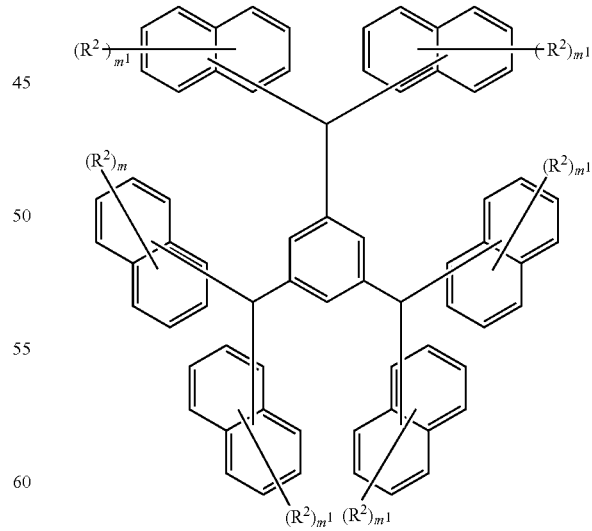
wherein $R^2$ and $m^1$ are the same as above.
Further examples of the compound represented by the above formula (1) can include, but not limited to, the followings:

[Chemical Formula 26]
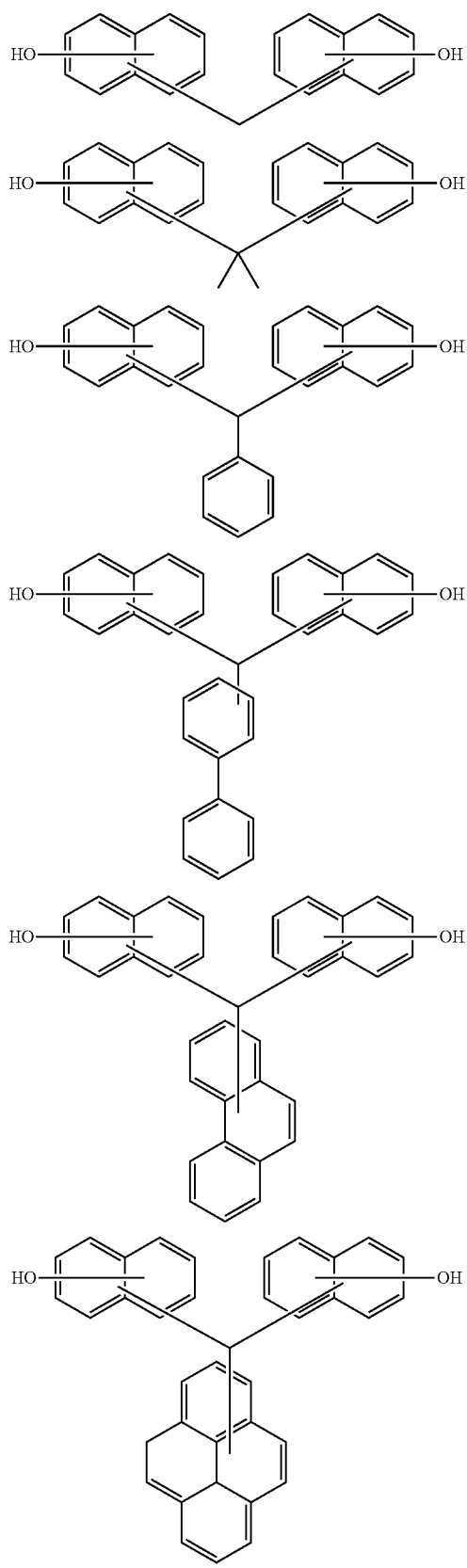
[Chemical Formula 27]
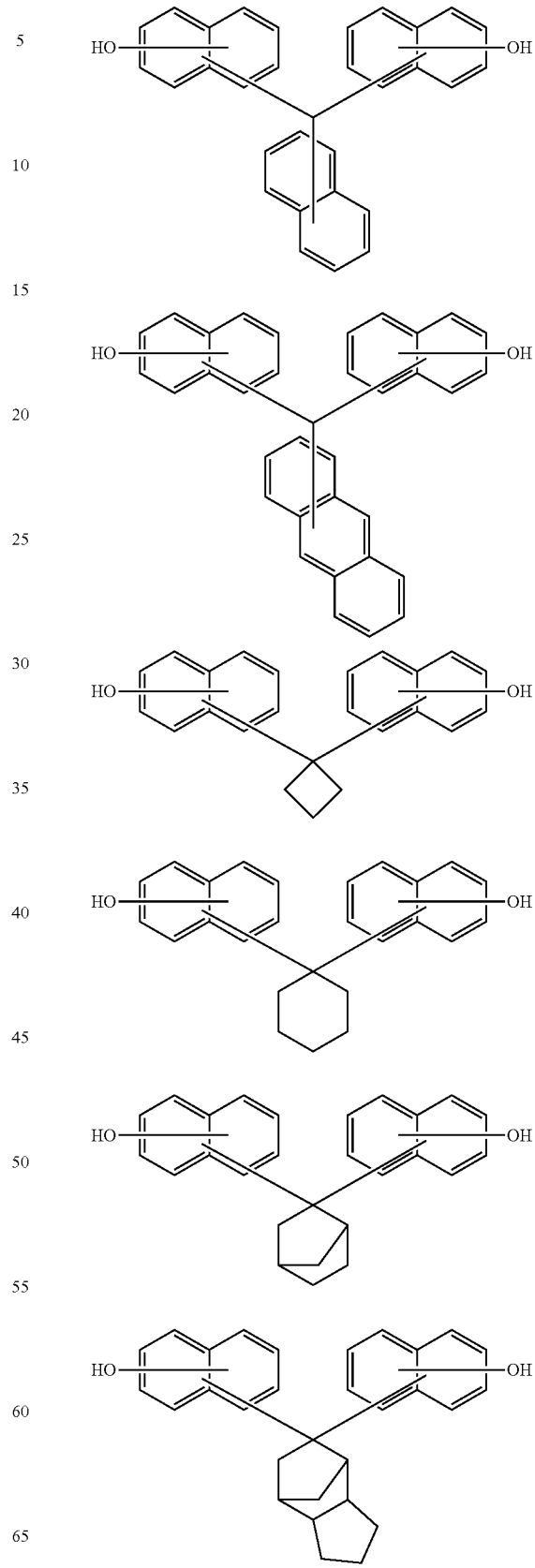

-continued
[Chemical Formula 28]
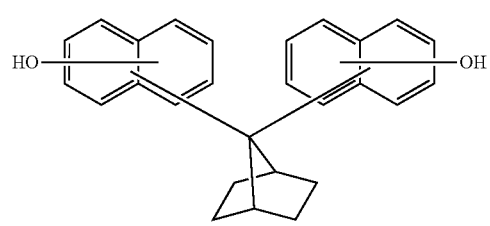
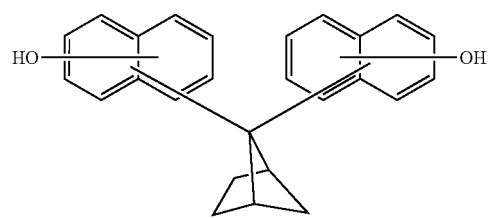
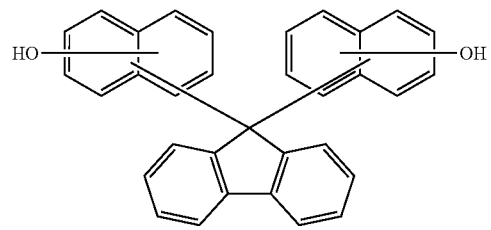
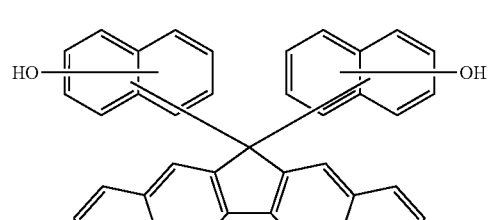
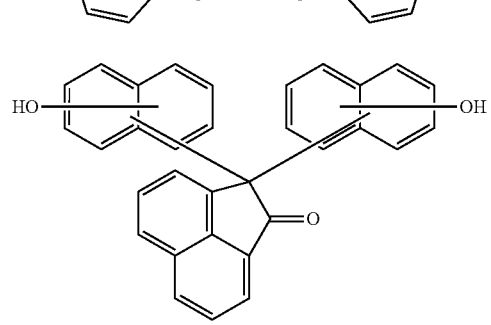
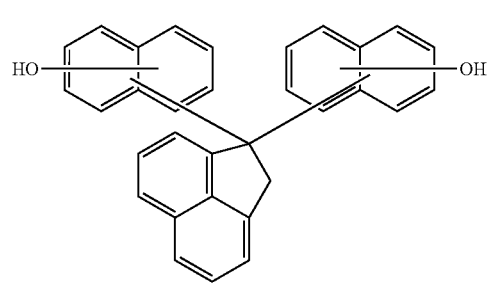
[Chemical Formula 29]
-continued
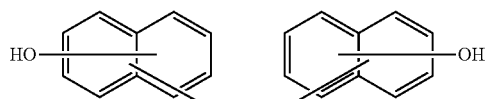
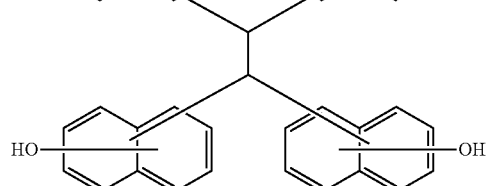
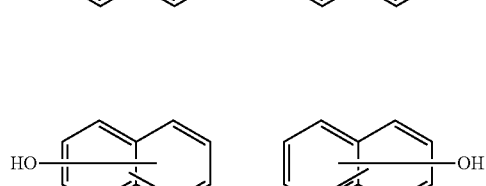
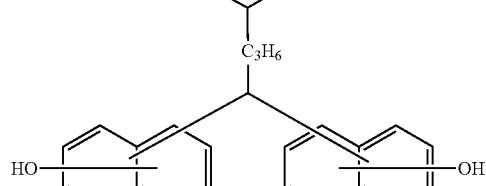
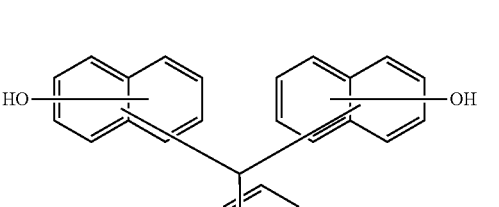
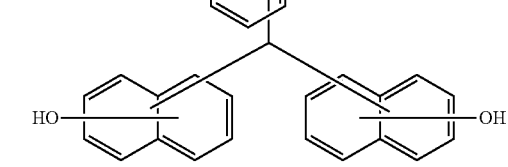
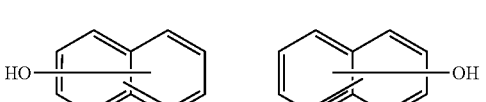
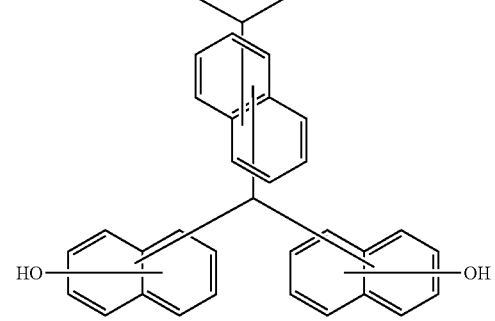

-continued

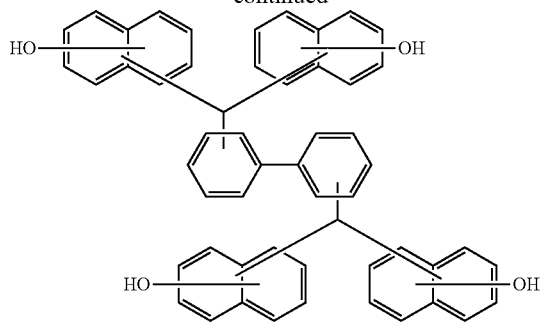

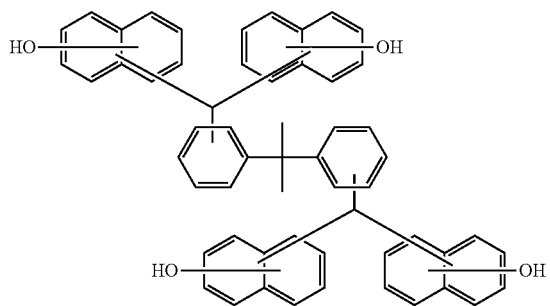

[Chemical Formula 30]

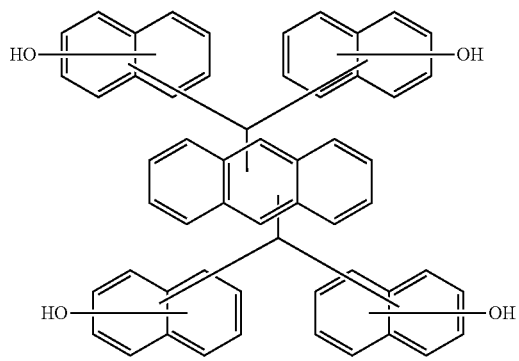

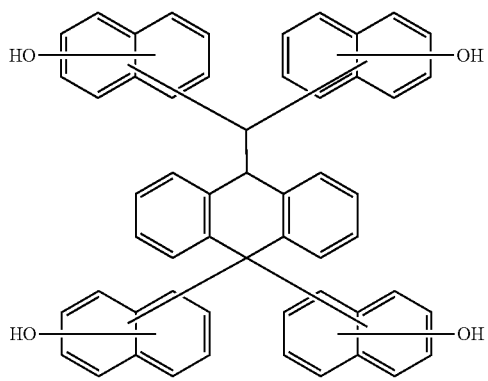

-continued

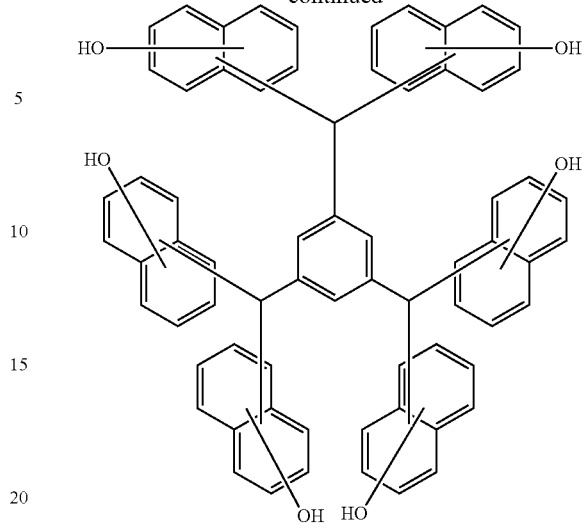

A method for producing the compound represented by the above formula (1) according to the present embodiment is not particularly limited. For example, the compound can be obtained by reacting a naphthol or a thionaphthol with a corresponding aldehyde or ketone in the presence of an acid catalyst.

Examples of the naphthol include, but not particularly limited to, naphthol, methylnaphthol, methoxynaphthol, and naphthalenediol. Naphthalenediol is more preferably used because a xanthene structure can be easily created.

Examples of the thionaphthol include, but not particularly limited to, naphthalenethiol, methylnaphthalenethiol, methoxynaphthalenethiol, and naphthalenedithiol.

Examples of the aldehyde include, but not particularly limited to, formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, bis(diformylphenyl)methane, bis(diformylphenyl)propane, and benzenetricarboxaldehyde. Benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, or benzenetricarboxaldehyde is preferably used in terms of providing high heat resistance.

Examples of the ketone include, but not particularly limited to, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone. Cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used in terms of providing high heat resistance.

The above acid catalyst is not particularly limited and can be arbitrarily selected from well known inorganic acids and organic acids. Examples thereof include: inorganic acids such as hydrochloric acid, sulfuric acid, phosphoric acid, hydrobromic acid, and hydrofluoric acid; organic acids such as oxalic acid, formic acid, p-toluenesulfonic acid, methanesulfonic acid, trifluoroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. From the viewpoint of production such as easy availability and handleability, hydrochloric acid or sulfuric acid is preferably used. As the acid catalyst, one kind or two or more kinds can be used.

Upon producing the compound represented by the above general formula (1), a reaction solvent may be used. The reaction solvent is not particularly limited as long as the reaction of the aldehyde or the ketone used with the naphthol or the thionaphthol proceeds. For example, water, methanol, ethanol, propanol, butanol, tetrahydrofuran, dioxane, or a mixed solvent thereof can be used. The amount of the solvent is not particularly limited and is within the range of, for example, 0 to 2000 parts by mass based on 100 parts by mass of the reaction raw materials.

Upon producing the compound represented by the above general formula (1), the reaction temperature is not particularly limited and can be arbitrarily selected according to the reactivity of the reaction raw materials. The reaction temperature is preferably within the range of 10 to 200° C. For highly selectively synthesizing the compound represented by the general formula (1) of the present embodiment, a lower temperature is more effective, and the range of 10 to 60° C. is more preferable.

The method for producing the compound represented by the above general formula (1) is not particularly limited and is, for example, a method of charging the naphthol or the thionaphthol, the aldehyde or the ketone, and the catalyst in one portion, or a method of dropping the naphthol or the thionaphthol and the aldehyde or the ketone in the presence of the catalyst. After the polycondensation reaction terminates, the temperature of the reaction vessel is elevated to 130 to 230° C. in order to remove unreacted raw materials, catalyst, etc. present in the system, and volatile portions can also be removed at about 1 to 50 mmHg.

Upon producing the compound represented by the above general formula (1), the amounts of the raw materials are not particularly limited. For example, by using 2 mol to an excess of the naphthol or the thionaphthol or the aldehyde or the ketone and 0.001 to 1 mol of the acid catalyst, based on 1 mol of the aldehyde or the ketone, the reaction proceeds at 20 to 60° C. at normal pressure for about 20 minutes to 100 hours.

Upon producing the compound represented by the above general formula (1), the target component is isolated by a publicly known method after the reaction terminates. Examples of a method for isolating the target component include, but not particularly limited to, a method of concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the objective compound.

Composition of Second Embodiment

According to the second embodiment, the resist composition of the present embodiment contains a compound represented by the following formula (2):

[Chemical Formula 31]

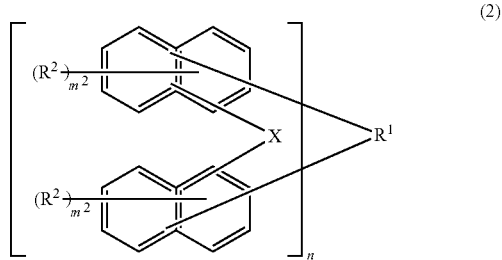

(2)

wherein X are each independently an oxygen atom or a sulfur atom; $R^1$ are each independently a single bond or a C1-30 2n-valent hydrocarbon group wherein the hydrocarbon group may have a cyclic hydrocarbon group, a double bond, a heteroatom, or a C6-30 aromatic group; $R^2$ are each independently a hydrogen atom, a halogen atom, a C1-10 linear, branched, or cyclic alkyl group, a C6-10 aryl group, a C2-10 alkenyl group, or a hydroxyl group and may be the same or different on the same naphthalene ring; at least one of $R^2$ is a hydroxyl group; the structural formulas of the repeating units in the formulas (1) and (2) may be the same or different; $m^2$ are each independently an integer of 1 to 6; and n is an integer of 1 to 4.

The 2n-valent hydrocarbon group is the same as in the above compound represented by the formula (1).

In the compound represented by the above formula (2), in terms of prevention of equipment contamination upon resist film exposure, X is preferably an oxygen atom. In terms of solubility in a safe solvent and resist pattern characteristics, the compound represented by the formula (2) is preferably a compound represented by the formula (2-1) having one or more phenolic hydroxyl groups per naphthalene group:

[Chemical Formula 32]

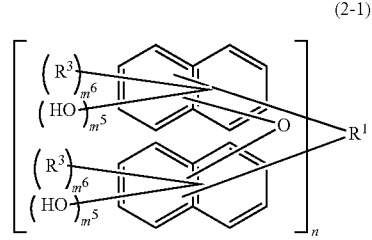

(2-1)

wherein $R^1$ is the same as above; $R^3$ are each independently a hydrogen atom, a C1-10 linear, branched, or cyclic alkyl group, a C6-10 aryl group, or a C2-10 alkenyl group; $m^5$ are each independently an integer of 1 to 6; $m^6$ are each independently an integer of 0 to 5; $m^5+m^6$ is an integer of 1 to 6; and n is the same as above.

In terms of sensitivity as a resist composition, the compound represented by the above formula (2-1) is more preferably a compound represented by the formula (2-2):

[Chemical Formula 33]

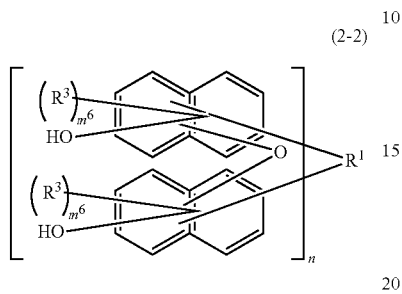

(2-2)

wherein $R^1$, $R^3$, and $m^6$ are the same as in the above formula (2-1).

In terms of solubility and sensitivity as a resist composition, $m^3$ in the above formula (2-1) is preferably 2.

In the present embodiment, in terms of resist characteristics such as heat resistance, sensitivity, resolution, and roughness, the compound represented by the above formula (2-1) is preferably a compound represented by the above formula (2-1) wherein n is 1.

In the present embodiment, in terms of solubility, the compound represented by the above formula (2-1) is still more preferably a compound represented by the formula (2-3):

[Chemical Formula 34]

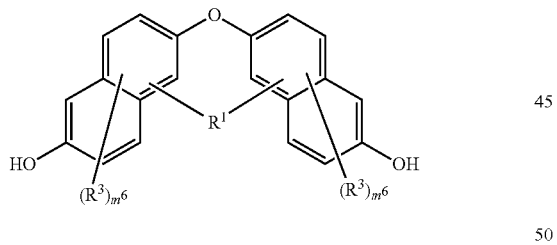

(2-3)

wherein $R^1$, $R^3$, and $m^6$ are the same as in the above formula (2-1).

Specific examples of the compound represented by the above general formula (2) can include, but not limited to, the followings:

[Chemical Formula 35]

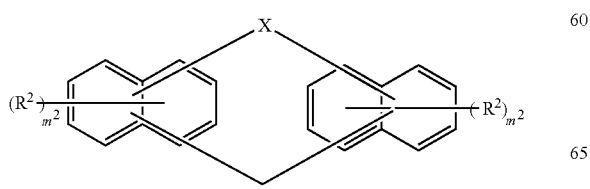

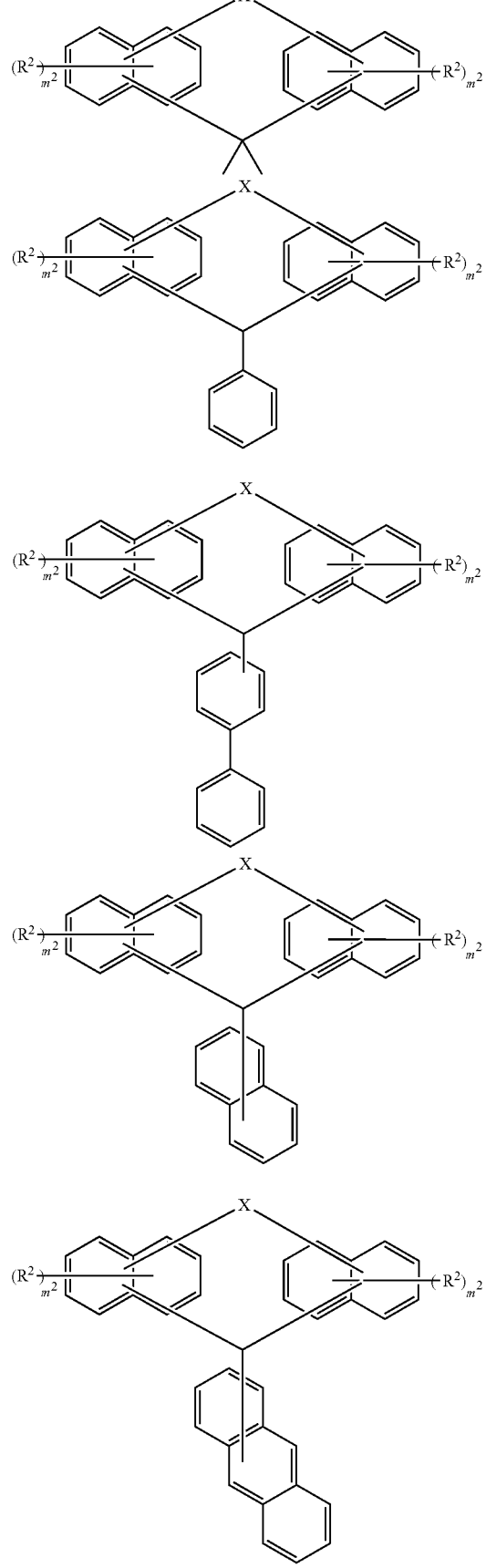

[Chemical Formula 36]
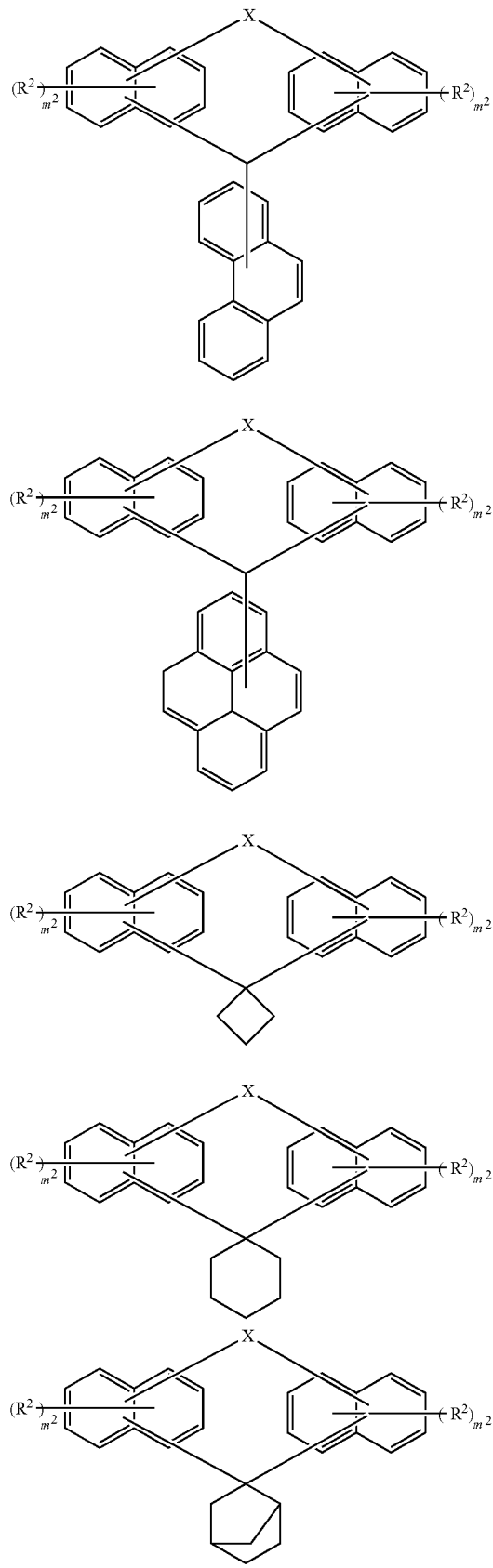
[Chemical Formula 37]
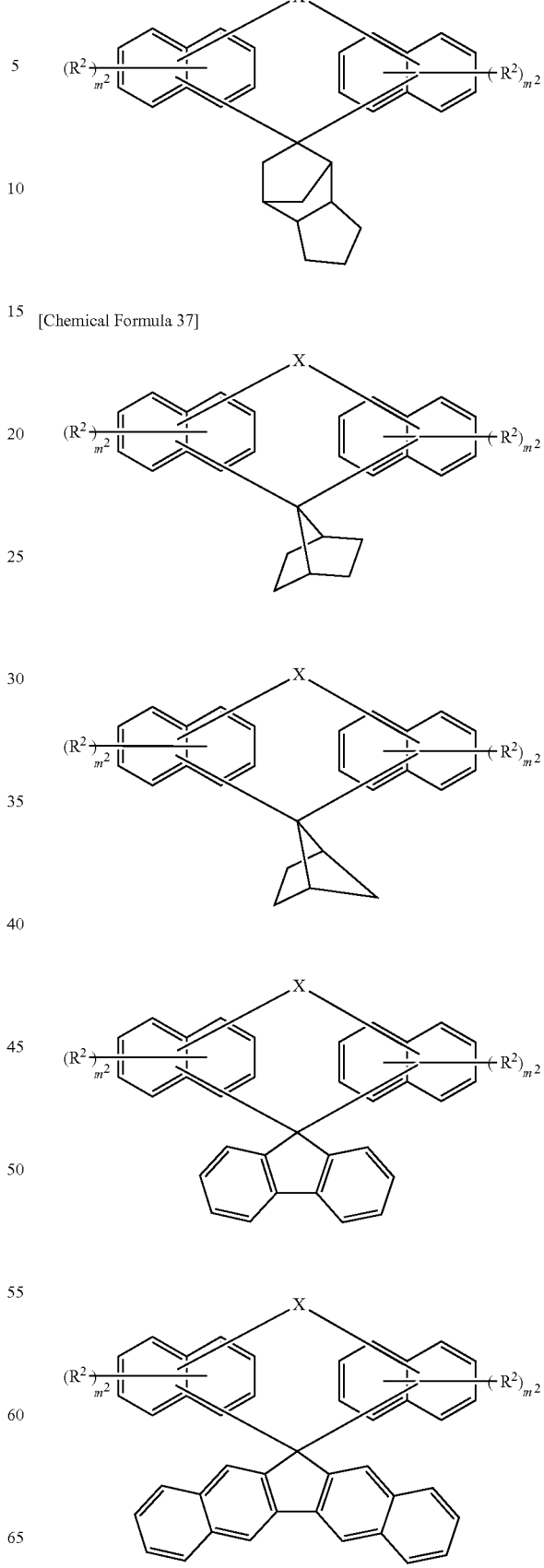

27
-continued
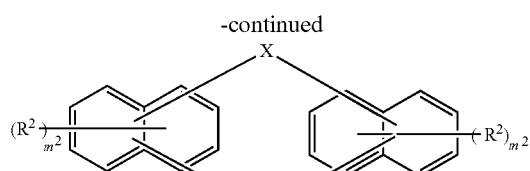
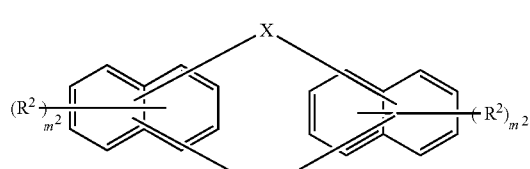
[Chemical Formula 38]
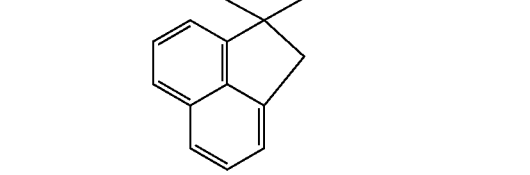
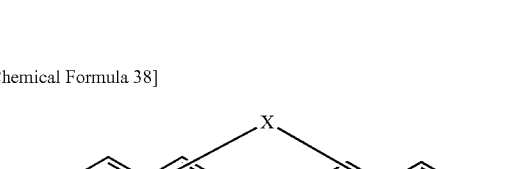
28
-continued
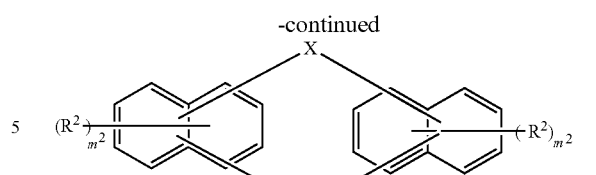
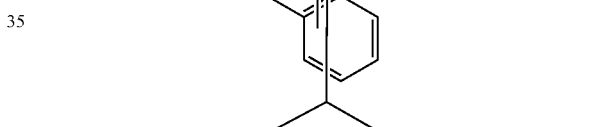
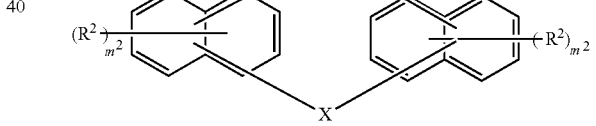
[Chemical Formula 39]
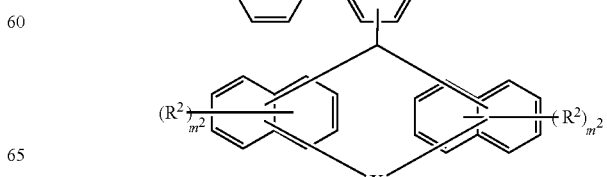

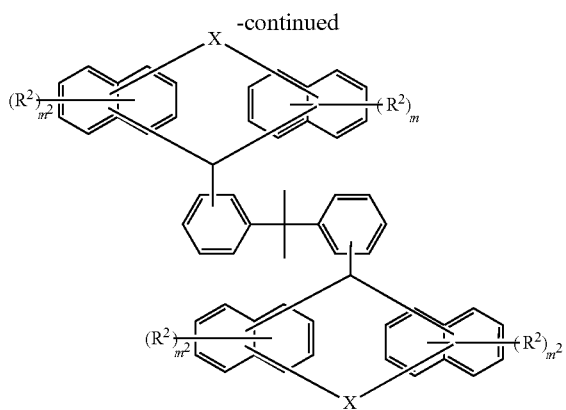
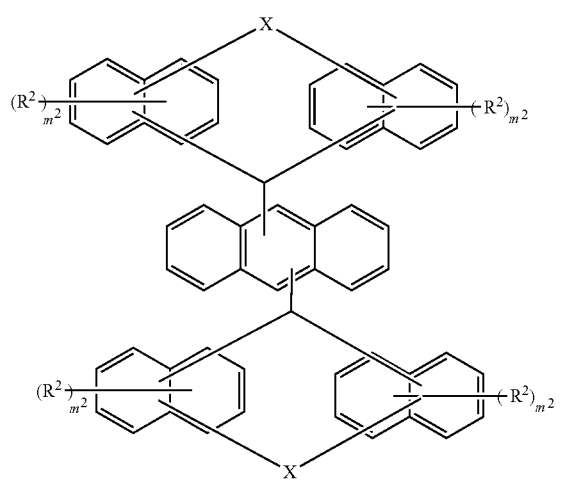
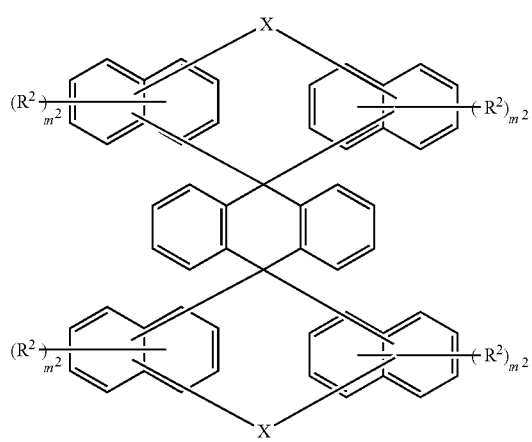
[Chemical Formula 40]
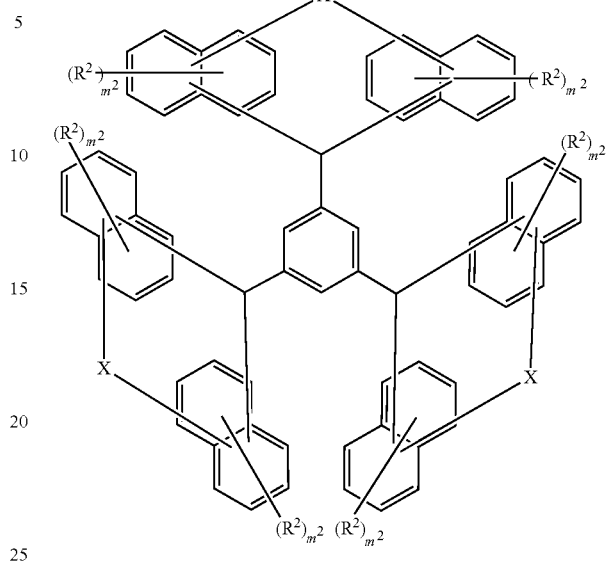
wherein R², X, and m² are the same as above.
Further examples of the compound represented by the general formula (2) can include, but not limited to, the followings:
[Chemical Formula 41]
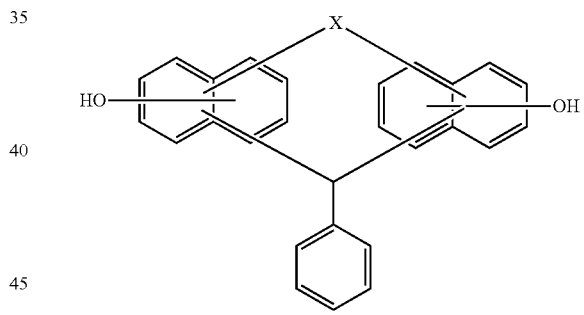
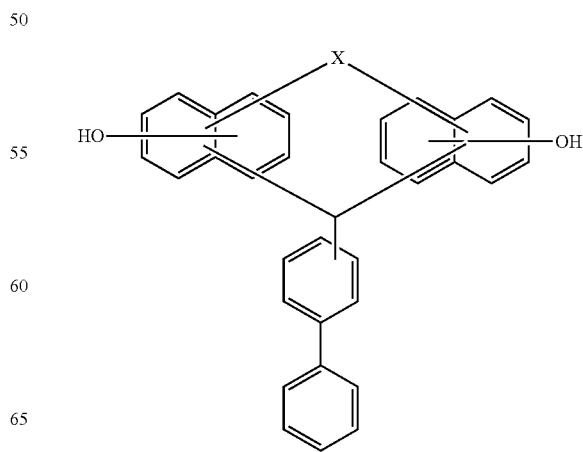

-continued
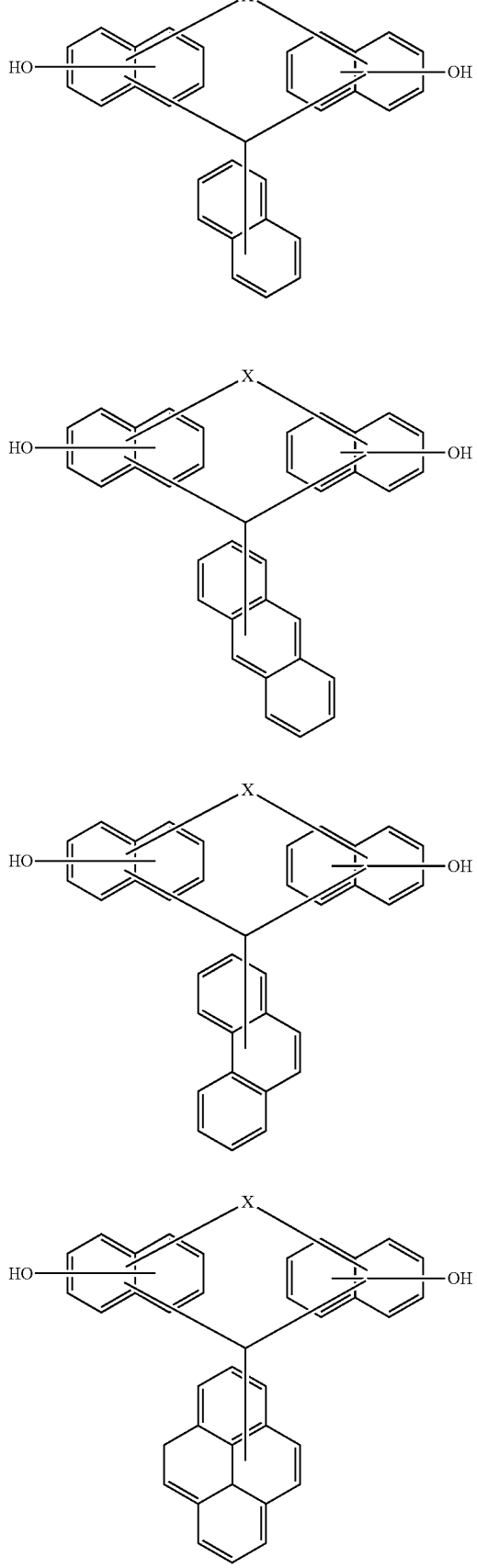
[Chemical Formula 42]
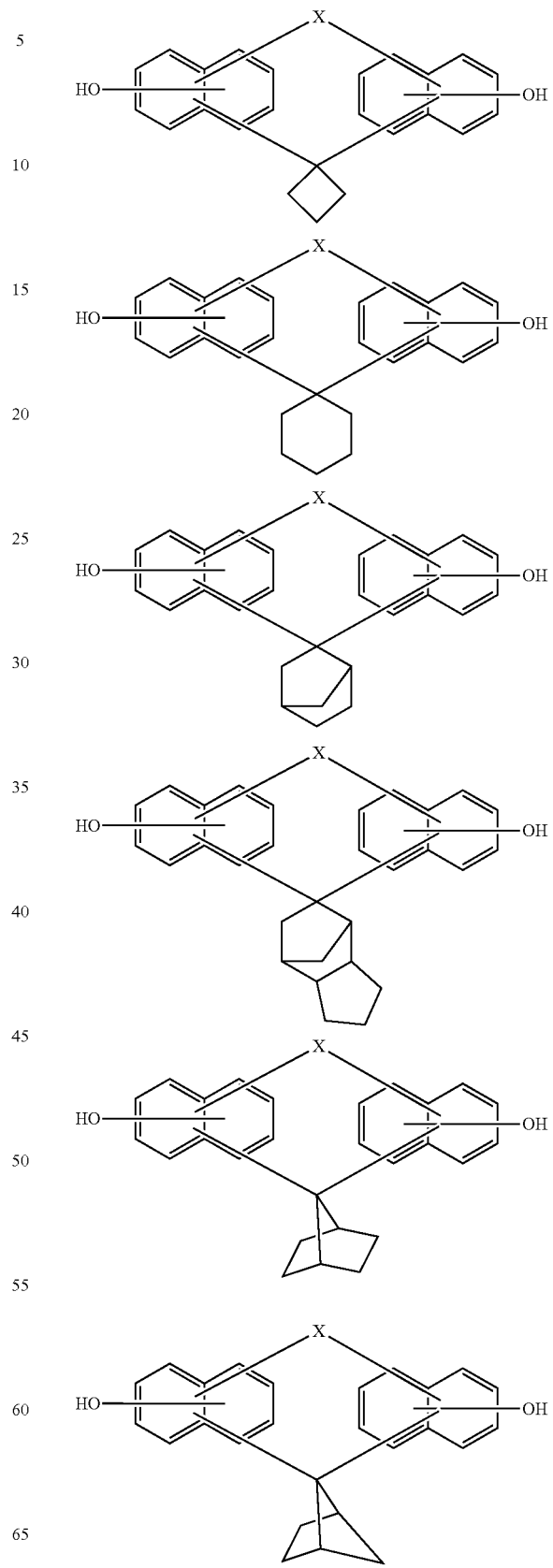

-continued
[Chemical Formula 43]
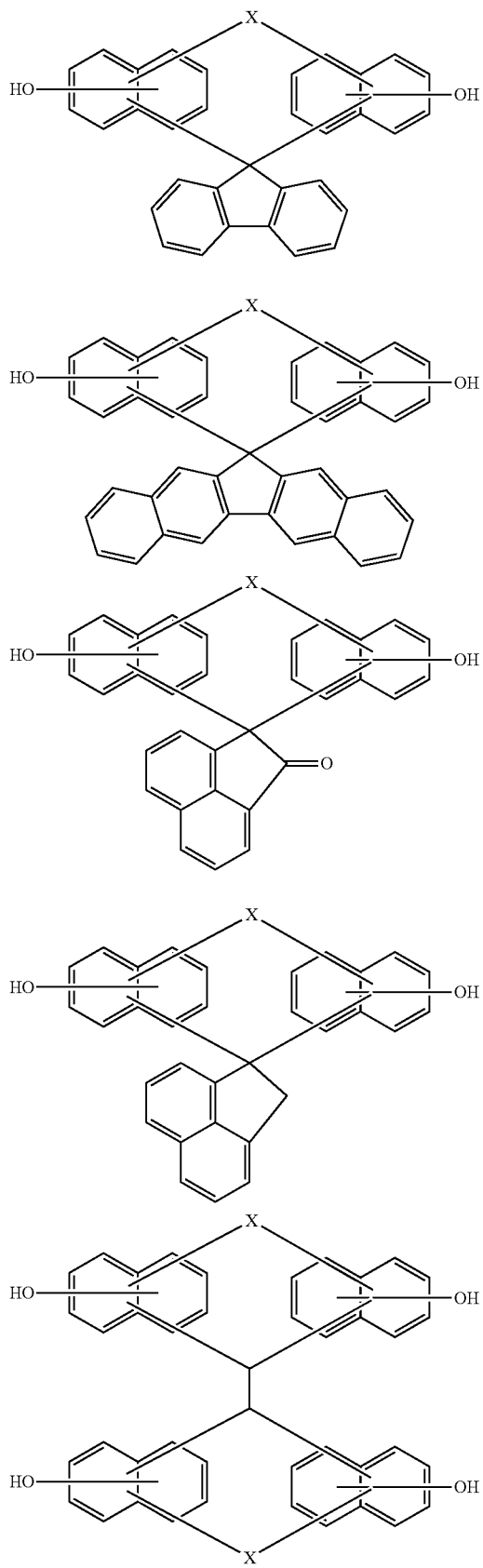
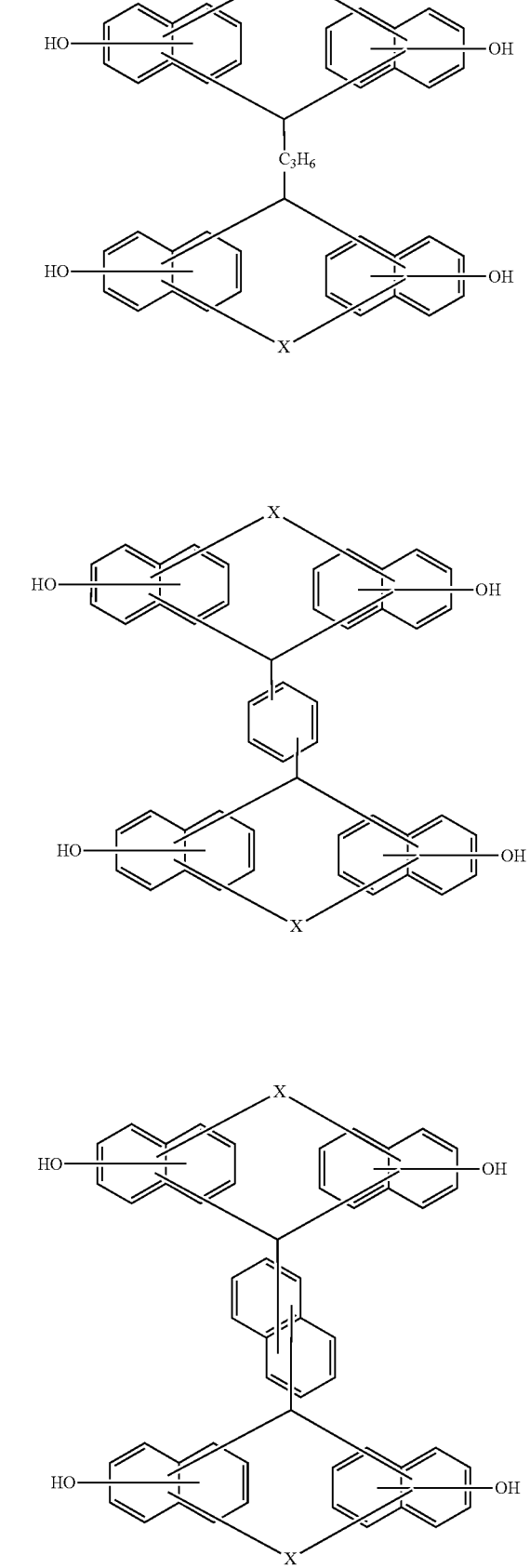

-continued

[Chemical Formula 44]

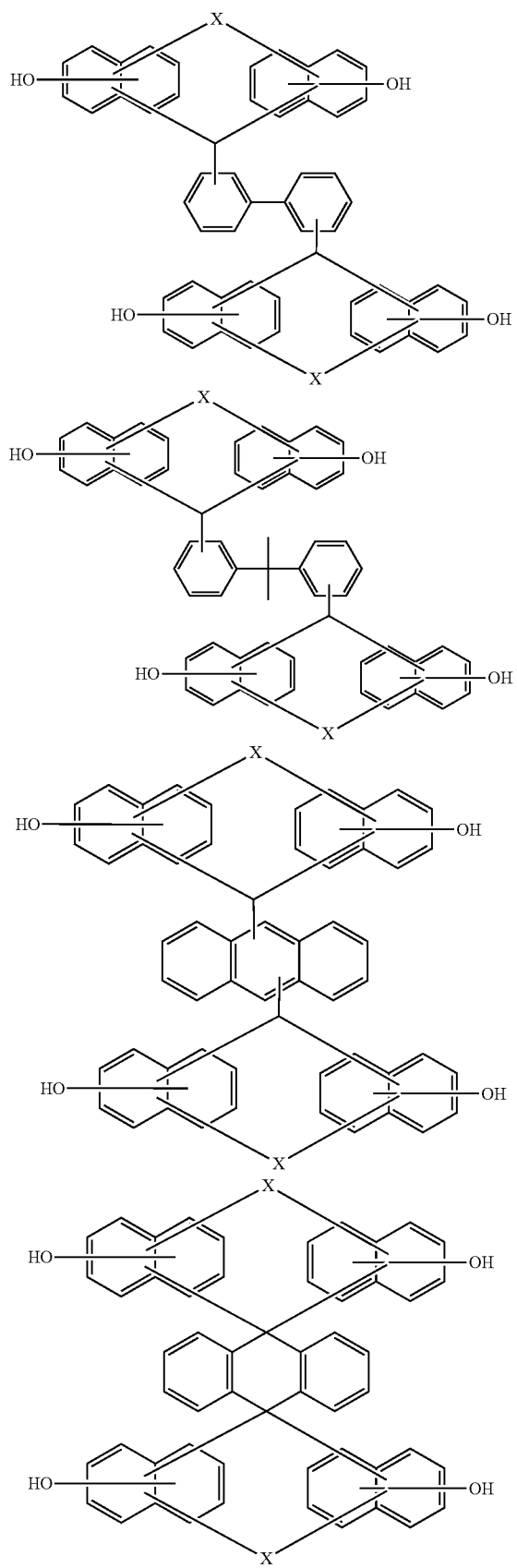

[Chemical Formula 45]

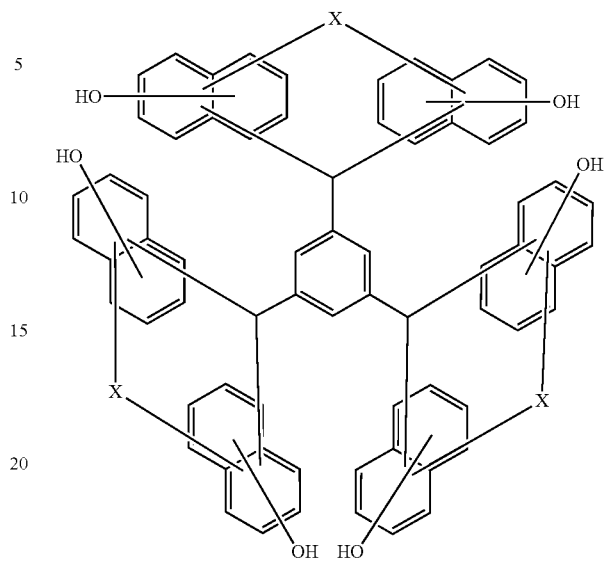

In the above formulas, X is the same as above and is preferably an oxygen atom in terms of prevention of equipment contamination upon resist film exposure.

The compound represented by the above formula (2) can be obtained, as in the compound (A) represented by the above formula (1), by reacting a naphthol or a thionaphthol with a corresponding aldehyde or ketone in the presence of an acid catalyst.

(Physical Properties, Etc. of Resist Composition)

The resist composition of the present embodiment can form an amorphous film by spin coating. In this case, the dissolution rate of the amorphous film formed by spin coating with the resist composition of the present embodiment in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film more easily dissolves in a developing solution, and is more suitably used for a resist. When the amorphous film has the dissolution rate of 10000 angstrom/sec or less, the resolution may improve. It is presumed that this is because due to the change in the solubility before and after exposure of the compound represented by the above formula (1) or (2), contrast at the interface between the unexposed portion being dissolved in a developing solution and the exposed portion not being dissolved in a developing solution is increased. There are also reduction effects of LER and defect. The dissolution rate can be determined by dipping the amorphous film in the developing solution at 23° C. for a predetermined time, and measuring film thicknesses before and after dipping according to a publicly known method such as visual observation, an ellipsometer, or a QCM method.

The dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the amorphous film is insoluble in a developing solution, and is suitably used for a resist. When the amorphous film has the dissolution rate of 0.0005 angstrom/sec or more, the resolution may improve. It is presumed that this is because the micro surface portion of the compound represented by the above formula (1) or (2) dissolves and LER is reduced. There is also a reduction effect of defect.

(Other Components of Resist Composition)

The resist composition of the present embodiment contains the compound represented by the above formula (1) or the compound represented by the above formula (2) as a solid component. The resist composition of the present embodiment may contain both of the compound represented by the above formula (1) and the compound represented by the above formula (2).

The resist composition of the present embodiment preferably further contains a solvent, in addition to the compound represented by the above formula (1) or (2).

Examples of the solvent used in the present embodiment include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate (PGMEA), propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as methyl ethyl ketone, 2-heptanone, 3-heptanone, 4-heptanone, cyclopentanone, and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the present embodiment is preferably a safe solvent, more preferably at least one kind selected from PGMEA, PGME, CHN, CPN, 2-heptanone, anisole, butyl acetate, ethyl propionate, and ethyl lactate, and still more preferably at least one kind selected from PGMEA, PGME, and CHN.

The amount of the solid component and the amount of the solvent are not particularly limited are preferably 1 to 80% by mass of the solid component and 20 to 99% by mass of the solvent, based on 100% by mass of the total mass of the solid component and the solvent, more preferably 1 to 50% by mass of the solid component and 50 to 99% by mass of the solvent, still more preferably 2 to 40% by mass of the solid component and 60 to 98% by mass of the solvent, and particularly preferably 2 to 10% by mass of the solid component and 90 to 98% by mass of the solvent.

The resist composition of the present embodiment may contain, as an additional solid component, at least one kind selected from the group consisting of an acid generating agent (C), an acid crosslinking agent (G), an acid diffusion controlling agent (E), and other component(s) (F).

The content of the compound represented by the formula (1) or (2) used in the present embodiment is not particularly limited and is preferably 50 to 99.4% by mass of the total mass of the solid component (summation of optionally used solid component such as compound represented by the formula (1), compound represented by the formula (2), acid generating agent (C), acid crosslinking agent (G), acid diffusion controlling agent (E), and other component (F), hereinafter the same), more preferably 55 to 90% by mass, still more preferably 60 to 80% by mass, and particularly preferably 60 to 70% by mass. In the case of the above content, resolution further improves, and line edge roughness (LER) further decreases.

When the resist composition contains both of the compound represented by the above formula (1) and the compound represented by the formula (2), the above content is the total amount of the compound represented by the above formula (1) and the compound represented by the formula (2).

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam.

In this case, the content of the acid generating agent (C) is preferably 0.001 to 49% by mass of the total mass of the solid component, more preferably 1 to 40% by mass, still more preferably 3 to 30% by mass, and particularly preferably 10 to 25% by mass. By using it within the above range, a pattern profile with higher sensitivity and lower edge roughness can be obtained.

In the present embodiment, the acid generation method is not limited as long as an acid is generated within a system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is not particularly limited. The acid generating agent (C) is preferably at least one kind selected from the group consisting of compounds represented by the following formulae (8-1) to (8-8):

[Chemical Formula 46]

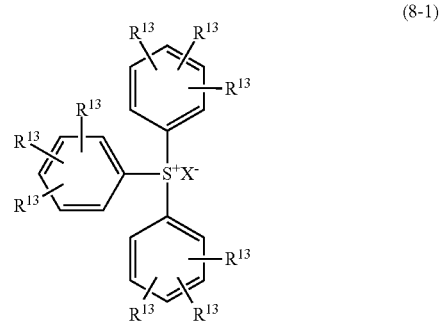

(8-1)

In the formula (8-1), $R^{13}$ may be the same or different, and are each independently a hydrogen atom, a linear, branched or cyclic alkyl group, a linear, branched or cyclic alkoxy group, a hydroxyl group, or a halogen atom; $X^-$ is a sulfonic acid ion having an alkyl group, an aryl group, a halogen substituted alkyl group or a halogen substituted aryl group, or a halide ion.

The compound represented by the above formula (8-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

[Chemical Formula 47]

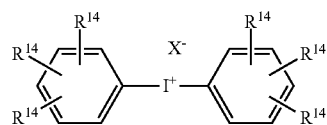

(8-2)

In the formula (8-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as above.

The compound represented by the above formula (8-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphersulfonate.

[Chemical Formula 48]

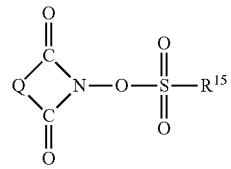

(8-3)

In the formula (8-3), Q is an alkylene group, an arylene group, or an alkoxylene group, and $R^{15}$ is an alkyl group, an aryl group, a halogen substituted alkyl group, or a halogen substituted aryl group.

The compound represented by the above formula (8-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxy)bicyclo[2.2.1]hept-5-en-2,3-dicarboxyimide, N-(2-trifluoromethylbenzenesulfonyloxy)naphthylimide, N-(4-trifluoromethylbenzenesulfonyloxy)bicyclo[2.2.1]hept-5-en-2,3-dicarboxyimide, N-(4-trifluoromethylbenzenesulfonyloxy)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxy)bicyclo[2.2.1]hept-5-en-2,3-dicarboxyimide, N-(1-naphthalenesulfonyloxy)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

[Chemical Formula 49]

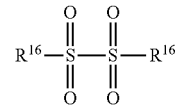

(8-4)

In the formula (8-4), $R^{16}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (8-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

[Chemical Formula 50]

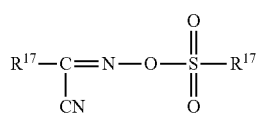

(8-5)

In the formula (8-5), $R^{17}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (8-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

[Chemical Formula 51]

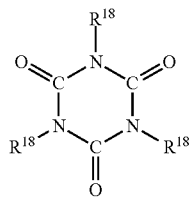

(8-6)

In the formula (8-6), $R^{18}$ may be the same or different, and are each independently a halogenated alkyl group having one or more chlorine atoms and one or more bromine atoms. The number of carbon atoms of the halogenated alkyl group is preferably 1 to 5.

[Chemical Formula 52]

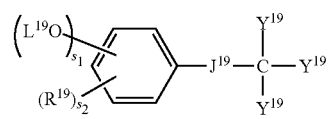

(8-7)

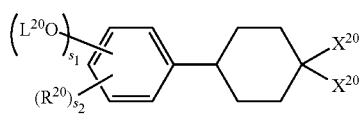

(8-8)

In the formulae (8-7) and (8-8), $R^{18}$ and $R^{20}$ are each independently an alkyl group having C1-3 such as a methyl group, an ethyl group, an n-propyl group, and an isopropyl group; a cycloalkyl group such as a cyclopentyl group and a cyclohexyl group; an alkoxyl group having C1-3 such as a methoxy group, an ethoxy group, and a propoxy group; or an aryl group such as a phenyl group, a toluoyl group, and a naphthyl group, and preferably an aryl group having C6-10. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. $s_1$ is an integer of 1 to 3; $s_2$ is an integer of 0 to 4; and $1 \le s_1 + s_2 \le 5$. $J^{19}$ is a single bond, a polymethylene group having C1-4, a cycloalkylene group, a phenylene group, a group represented by the following formula (8-7-1), a carbonyl group, an ester group, an amide group, or an ether group. $Y^{19}$ is a hydrogen atom, an alkyl group, or an aryl group, and $X^{20}$ are each independently a group represented by the following formula (8-8-1):

[Chemical Formula 53]

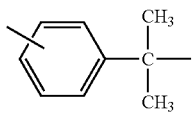

(8-7-1)

[Chemical Formula 54]

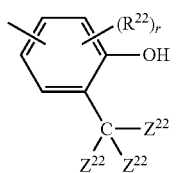

(8-8-1)

In the formula (8-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.

Examples of the other acid generating agent include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the acid generating agents, an acid generating agent having an aromatic ring is preferable, and an acid generating agent represented by the formula (8-1) or (8-2) is more preferable. An acid generating agent having a sulfonate ion wherein X⁻ of the formula (8-1) or (8-2) has an aryl group or a halogen-substituted aryl group is still more preferable; an acid generating agent having a sulfonate ion having an aryl group is particularly preferable; and diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate are particularly preferable. By using the acid generating agent, LER can be reduced.

The acid generating agent (C) can be used alone or in combination of two or more kinds.

The resist composition of the present embodiment preferably contains one or more acid crosslinking agents (G). The acid crosslinking agent (G) is a compound capable of intramolecular or intermolecular crosslinking the compound represented by the formula (1) in the presence of the acid generated from the acid generating agent (C). Examples of such an acid crosslinking agent (G) include, but not particularly limited to, a compound having one or more groups (hereinafter, referred to as "crosslinkable group") capable of crosslinking the compound represented by the formula (1).

Specific examples of such a crosslinkable group include (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group having the acid crosslinking agent (G) of the present invention, a hydroxyalkyl group and an alkoxyalkyl group or the like are preferable, and an alkoxymethyl group is particularly preferable.

Examples of the acid crosslinking agent (G) having the above crosslinkable group include (i) a methylol group-containing compound such as a methylol group-containing melamine compound, a methylol group-containing benzoguanamine compound, a methylol group-containing urea compound, a methylol group-containing glycoluryl compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluryl compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound and resin where the above crosslinkable group is introduced into an acid functional group in an alkali soluble resin to impart crosslinkability can be further used. The introduction rate of the crosslinkable group in that case is not particularly limited, but is adjusted, for example, to be normally 5 to 100 mol %, preferably 10 to 60 mol %, and more preferably 15 to 40 mol % based on the total acid functional groups in the compound having a phenolic hydroxyl group, and the alkali soluble resin. Within the above range, the crosslinking reaction sufficiently occurs, and a decrease in the film remaining rate, and swelling phenomena and meandering or the like of a pattern can be avoided, which is preferable.

In the resist composition of the present embodiment, as the acid crosslinking agent (G), an alkoxyalkylated urea compound or resin thereof, or an alkoxyalkylated glycoluryl compound or resin thereof is preferable. Particularly preferable examples of the acid crosslinking agent (G) include compounds represented by the following formulae (9-1) to (9-3) and an alkoxymethylated melamine compound (acid crosslinking agent (G1)).

[Chemical Formula 55]

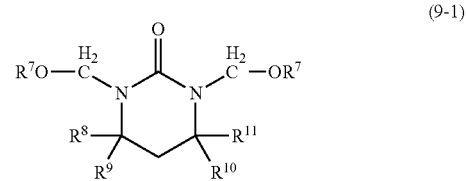

(9-1)

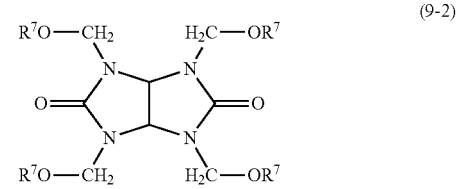

(9-2)

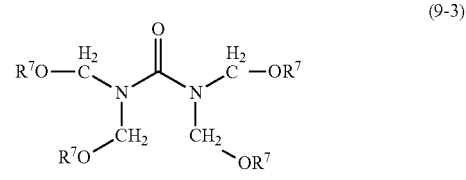

(9-3)

In the formulae (9-1) to (9-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.

The alkyl group represented by $R^7$ is not particularly limited, but is preferably C1-6, and more preferably C1-3. Examples thereof include a methyl group, an ethyl group, and a propyl group. The acyl group represented by $R^7$ is not particularly limited, but is preferably C2-6, and more preferably C2-4. Examples thereof include an acetyl group and a propyonyl group. The alkyl group represented by $R^8$ to $R^{11}$ is not particularly limited, but is preferably C1-6, and more preferably C1-3. Examples thereof include a methyl group, an ethyl group, and a propyl group. The alkoxy group represented by $R^8$ to $R^{11}$ is preferably C1-6, and more preferably C1-3. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different.

Specific examples of the compound represented by the formula (9-1) include compounds shown below:

[Chemical Formula 56]

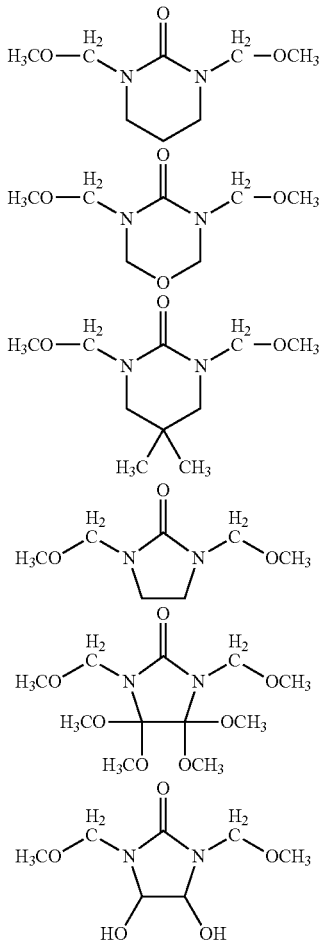

Specific examples of the compound represented by the formula (9-2) include N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among them, particularly, N,N,N,N-tetra(methoxymethyl)glycoluryl is preferable.

Specific examples of the compound represented by the formula (9-3) include compounds shown below:

[Chemical Formula 57]

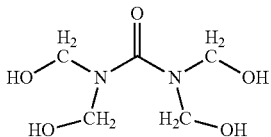

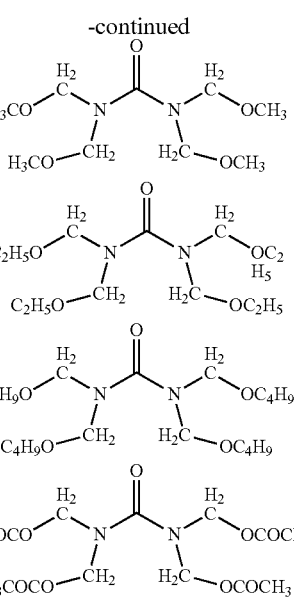

Specific examples of the alkoxymethylated melamine compound include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among them, particularly, N,N,N,N,N,N-hexa(methoxymethyl)melamine is preferable.

The above acid crosslinking agent (G1) can be obtained by, for example, conducting a condensation reaction of a urea compound or a glycoluryl compound with formalin to introduce an methylol group, etherifying the product with lower alcohols such as methyl alcohol, ethyl alcohol, propyl alcohol, and butyl alcohol, and then cooling the reaction solution to collect a precipitated compound or resin thereof. The above acid crosslinking agent (G1) can be obtained as a commercially available product such as CYMEL (trade name, manufactured by Mitsui Cyanamid) and NIKALAC (manufactured by Sanwa Chemical Co., Ltd.).

Other particularly preferable examples of the acid crosslinking agent (G) include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). Preferable examples thereof include a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one of or a plurality of the above benzene rings.

The hydroxyalkyl group bonded to a benzene ring is not particularly limited, but the one of C1-6 such as a hydroxymethyl group, a 2-hydroxyethyl group, and a 2-hydroxy-1-propyl group is preferable. As the alkoxyalkyl group bonded to a benzene ring, the one of C2-6 is preferable. Specifically, a methoxymethyl group, an ethoxymethyl group, an n-propoxymethyl group, an isopropoxymethyl group, an n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, particularly preferable ones are shown below:
[Chemical Formula 58]
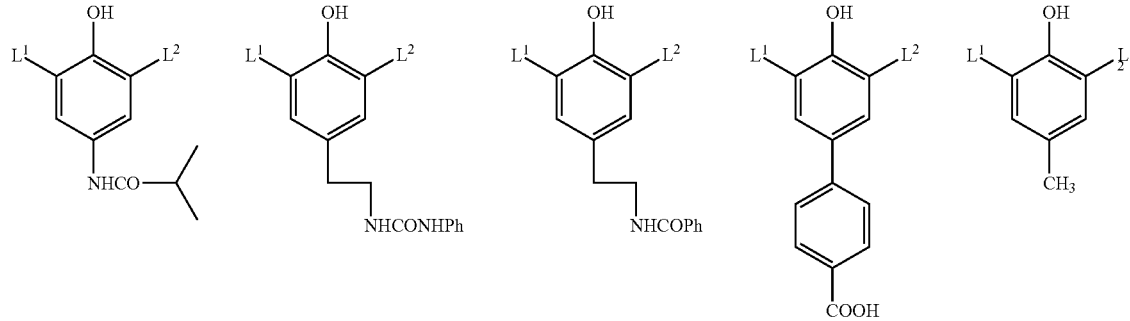
[Chemical Formula 59]
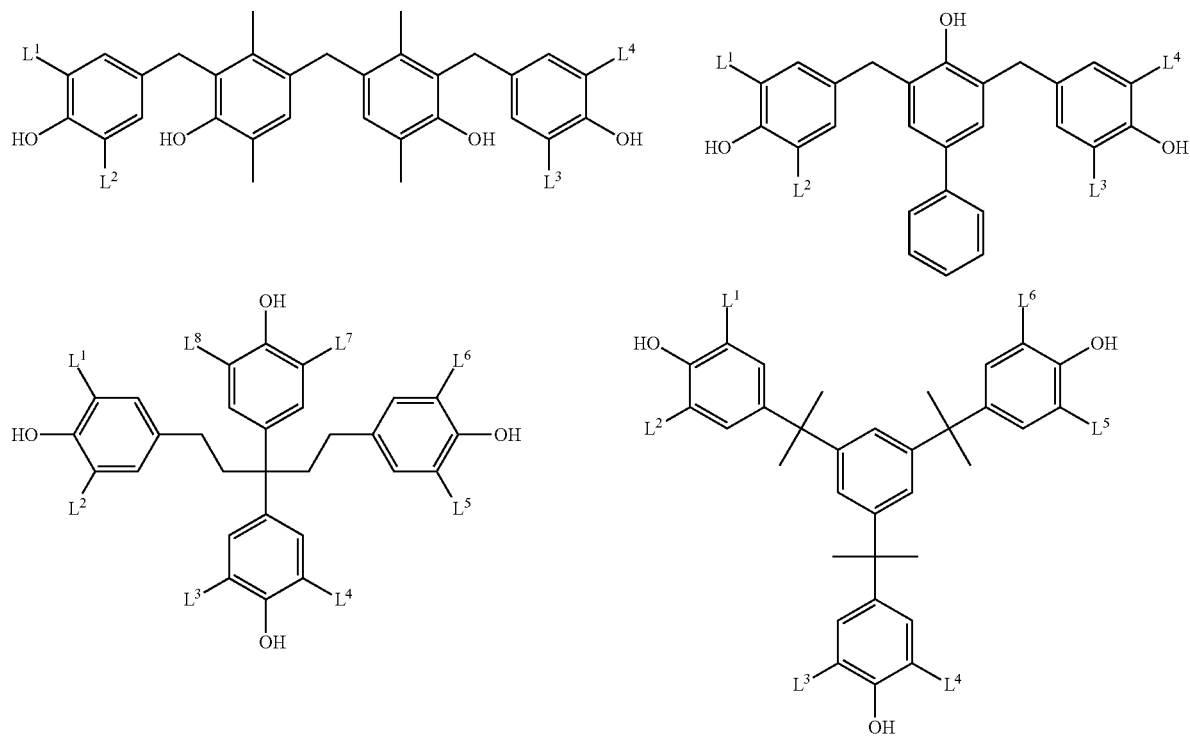
[Chemical Formula 60]
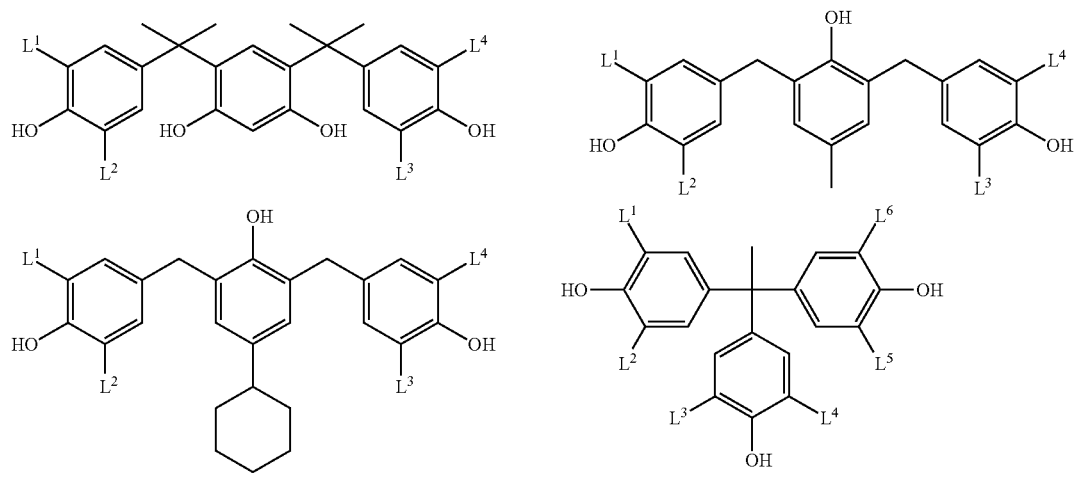

-continued
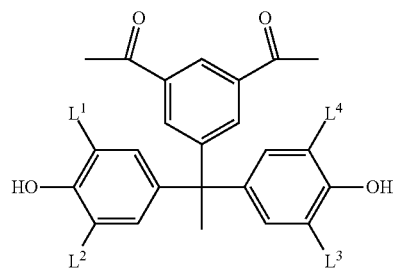
[Chemical Formula 61]
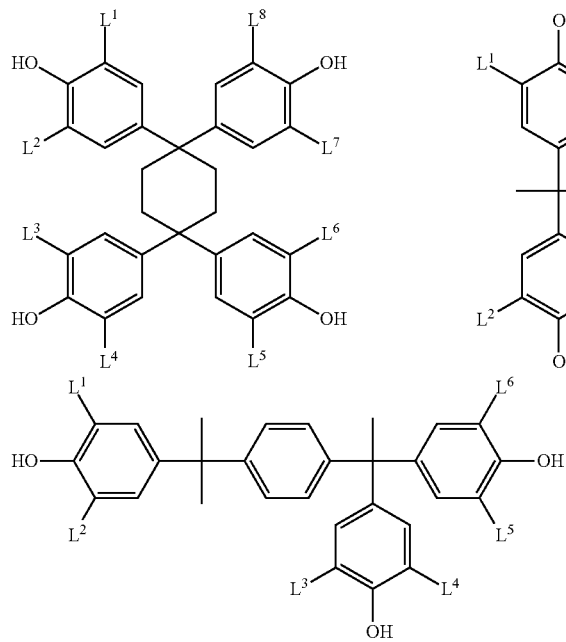 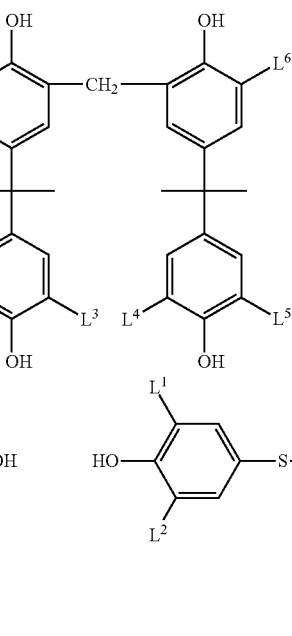
[Chemical Formula 62]
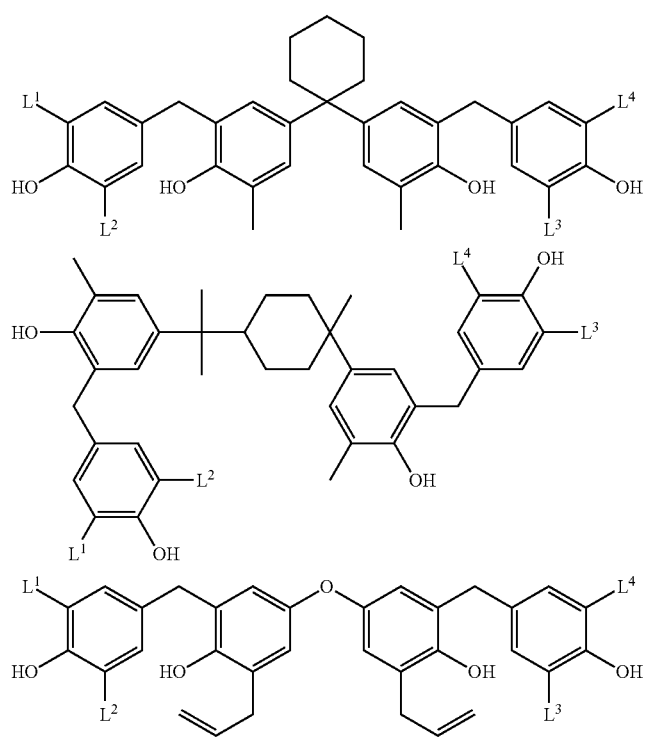

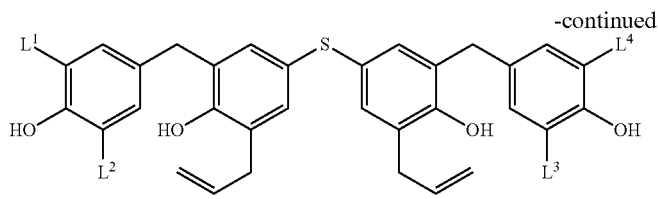

[Chemical Formula 63]

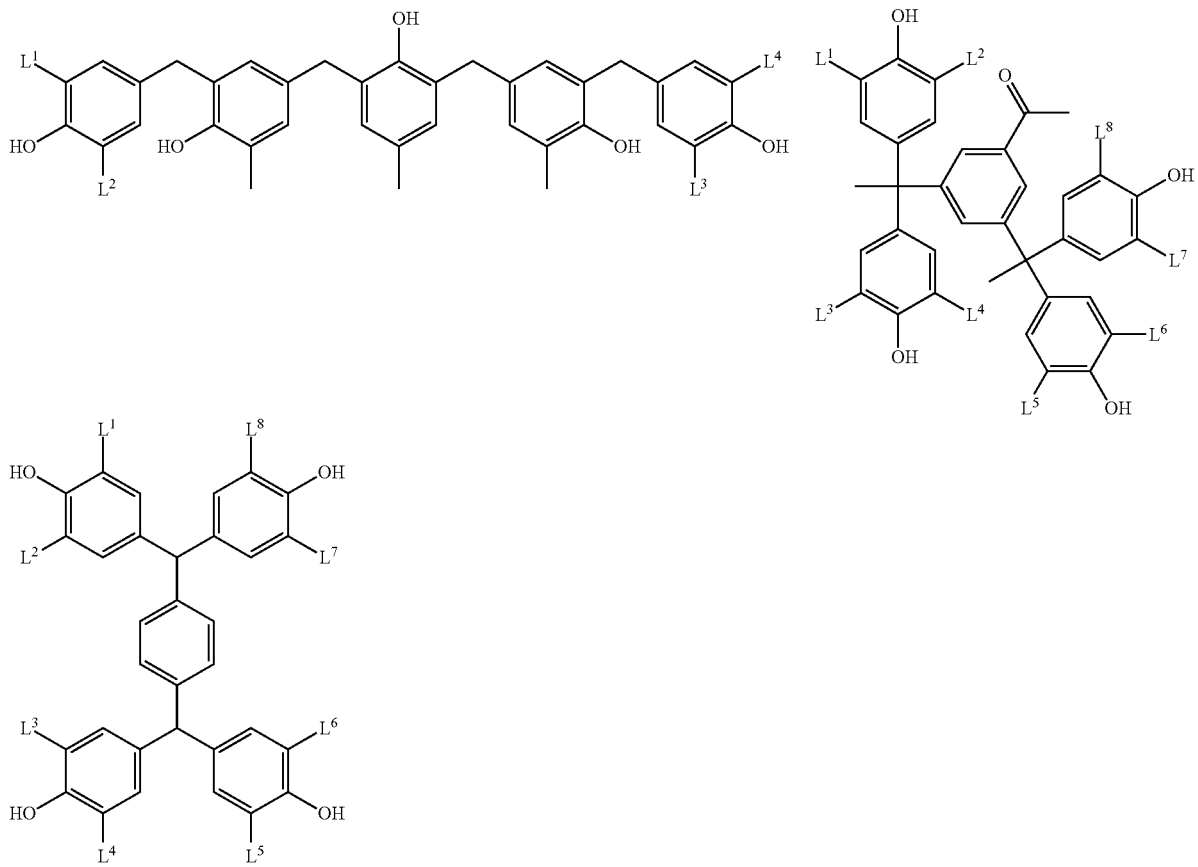

In the formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where $L^1$ to $L^8$ in the formulae are a hydrogen atom) with formaldehyde in the presence of a basic catalyst. In this case, in order to prevent resinification and gelation, the reaction temperature is preferably 60° C. or less. Specifically, it can be synthesized by methods described in Japanese Patent Application Laid-Open Nos. H6-282067 and H7-64285 or the like.

A phenol derivative having an alkoxymethyl group can be obtained by reacting the corresponding phenol derivative having a hydroxymethyl group with an alcohol in the presence of an acid catalyst. In this case, in order to prevent resinification and gelation, the reaction temperature is preferably 100° C. or less. Specifically, it can be synthesized by methods described in EP632003A1 or the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Other particularly preferable examples of the acid crosslinking agent (G) include a compound having at least one α-hydroxyisopropyl group (acid crosslinking agent (G3)). The compound is not particularly limited in the structure, as long as it has an α-hydroxyisopropyl group. A hydrogen atom of a hydroxyl group in the α-hydroxyisopropyl group may be substituted with one or more acid dissociation groups (R—COO— group, R—SO$_2$— group or the like, wherein R represents a substituent group selected from the group consisting of a linear hydrocarbon group having C1-12, a cyclic hydrocarbon group having C3-12, an alkoxy group having C1-12, a 1-branched alkyl group having C3-12, and an aromatic hydrocarbon group having C6-12). Examples of a compound having the α-hydroxyisopropyl group include one kind or two kinds or more of a substituted or non-substituted aromatic based compound, a diphenyl compound, a naphthalene compound, a furan compound or the like containing at least one α-hydroxyisopropyl group. Specific examples thereof include a compound represented by the following general formula (10-1) (hereinafter, referred to as "benzene based compound (1)"), a compound represented by the following general formula (10-2) (hereinafter, referred to as "diphenyl based compound (2)"), a compound represented by the following general formula (10-3) (hereinafter, referred to as "naphthalene based compound (3)"), and a compound represented by the following general formula (10-4) (hereinafter, referred to as "furan based compound (4)").

[Chemical Formula 64]

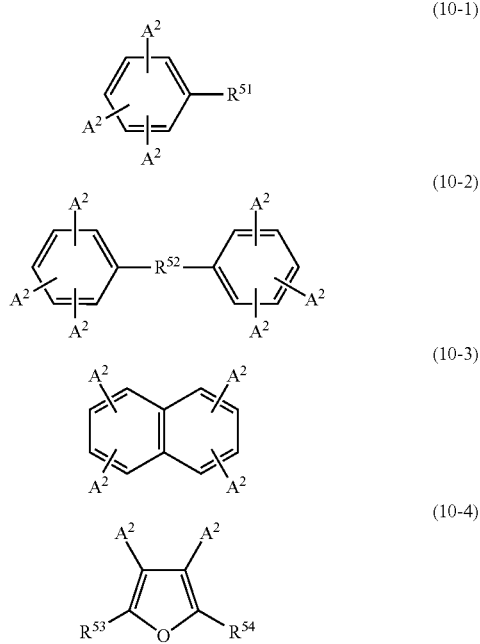

(10-1)
(10-2)
(10-3)
(10-4)

In the general formulae (10-1) to (10-4), each $A^2$ independently represents an α-hydroxyisopropyl group or a hydrogen atom, and at least one $A^2$ is an α-hydroxyisopropyl group. In the general formula (10-1), $R^{51}$ represents a hydrogen atom, a hydroxyl group, a linear or branched alkylcarbonyl group having C2-6, or a linear or branched alkoxycarbonyl group having C2-6. Furthermore, in the general formula (10-2), $R^{52}$ represents a single bond, a linear or branched alkylene group having C1-5, —O—, —CO—, or —COO—. Also, in the general formula (10-4), $R^{53}$ and $R^{54}$ represent a hydrogen atom or a linear or branched alkyl group having C1-6 independently from each other.

Specific examples of the benzene based compound (1) include α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl-n-propyl ketone, 4-α-hydroxyisopropylphenyl isopropyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the diphenyl based compound (2) include α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6,-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;
α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyl)diphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;
α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;
α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'- bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl) diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the naphthalene based compound (3) include 1-(α-hydroxyisopropyl) naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl) naphthalene.

Specific examples of the furan based compound (4) include 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl) furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are more preferable; and α-hydroxyisopropylbiphenyls having two or more α-hydroxyisopropyl groups and the above naphthalene based compound (3) having two or more α-hydroxyisopropyl groups are particularly preferable.

The acid crosslinking agent (G3) can normally be obtained by a method for reacting an acetyl group-containing compound such as 1,3-diacetylbenzene with Grignard reagent such as $CH_3MgBr$ to methylate and then hydrolyzing, or a method for oxidizing an isopropyl group-containing compound such as 1,3-diisopropylbenzene with oxygen or the like to produce a peroxide and then reducing.

The content of the acid crosslinking agent (G) in the present embodiment is preferably 0.5 to 49% by mass of the total mass of the solid component, more preferably 0.5 to 40% by mass, still more preferably 1 to 30% by mass, and particularly preferably 2 to 20% by mass. When the content of the above acid crosslinking agent (G) is 0.5% by mass or more, the inhibiting effect of the solubility of a resist film in an alkaline developing solution can be improved, and a decrease in the film remaining rate, and occurrence of swelling and meandering of a pattern can be inhibited, which is preferable. On the other hand, when the content is 50% by mass or less, a decrease in heat resistance as a resist can be further inhibited, which is preferable.

The content of at least one kind of compound selected from the acid crosslinking agent (G1), acid crosslinking agent (G2), and acid crosslinking agent (G3) in the acid crosslinking agent (G) is also not particularly limited, and can be within various ranges according to the kind of substrates or the like used upon forming a resist pattern.

In all acid crosslinking agent components, the content of the alkoxymethylated melamine compound and/or the compounds represented by (10-1) to (10-3) is not particularly limited, but is preferably 50 to 99% by mass, more preferably 60 to 99% by mass, much more preferably 70 to 98% by mass, and particularly preferably 80 to 97% by mass. By having the alkoxymethylated melamine compound and/or the compounds represented by (10-1) to (10-3) of 50% by mass or more of all acid crosslinking agent components, the resolution can be further improved, which is preferable. By having the compounds of 99% by mass or less, the pattern cross section is likely to have a rectangular shape, which is preferable.

The resist composition of the present embodiment may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition is improved. Also, along with the further improvement of the resolution, the line width change of a resist pattern due to variation in the post exposure delay time before radiation irradiation and the post exposure delay time after radiation irradiation can be inhibited, and the composition has extremely excellent process stability.

Examples of such an acid diffusion controlling agent (E) include, but not particularly limited to, a radiation degradable basic compound such as a nitrogen atom-containing basic compound, a basic sulfonium compound, and a basic iodonium compound. The acid diffusion controlling agent (E) can be used alone or in combination of two or more kinds.

Examples of the acid diffusion controlling agent include a nitrogen-containing organic compound, and a basic compound degradable by exposure. Examples of the nitrogen-containing organic compound include a compound represented by the following general formula (11):

[Chemical Formula 65]

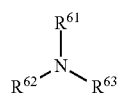

(11)

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the general formula (11), $R^{61}$, $R^{62}$, and $R^{63}$ represent a hydrogen atom, a linear, branched or cyclic alkyl group, an aryl group, or an aralkyl group independently from each other. The alkyl group, aryl group, or aralkyl group may be non-substituted or may be substituted with a hydroxyl group or the like. Herein, examples of the linear, branched or cyclic alkyl group include, but not particularly limited to, the one of C1-15, and preferably C1-10. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the aryl group include the one of C6-12. Specific examples thereof include a phenyl group, a tolyl group, a xylyl group, a cumenyl group, and a 1-naphthyl group. Furthermore, examples of the aralkyl group include, but not particularly limited to, the one of C7-19, and preferably C7-13. Specific examples thereof include a benzyl group, an α-methylbenzyl group, a phenethyl group, and a naphthylmethyl group.

Specific examples of the nitrogen-containing compound (I) include, but not particularly limited to, mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the nitrogen-containing compound (II) include, but not particularly limited to, ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Specific examples of the nitrogen-containing compound (III) include, but not particularly limited to, polymers of polyethyleneimine, polyarylamine, and N-(2-dimethylaminoethyl)acrylamide.

Specific examples of the amide group-containing compound include, but not particularly limited to, formamide, N-methylformamide, N,N-dimethylformamide, acetamide, N-methylacetamide, N,N-dimethylacetamide, propioneamide, benzamide, pyrrolidone, and N-methylpyrrolidone.

Specific examples of the urea compound include, but not particularly limited to, urea, methylurea, 1,1-dimethylurea, 1,3-dimethylurea, 1,1,3,3-tetramethylurea, 1,3-diphenylurea, and tri-n-butylthiourea.

Specific examples of the nitrogen-containing heterocyclic compound include, but not particularly limited to, imidazoles such as imidazole, benzimidazole, 4-methylimidazole, 4-methyl-2-phenyl imidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the radiation degradable basic compound include, but not particularly limited to, a sulfonium compound represented by the following general formula (12-1):

[Chemical Formula 66]

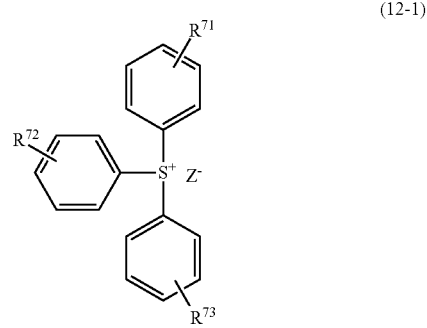

(12-1)

and an iodonium compound represented by the following general formula (12-2):

[Chemical Formula 67]

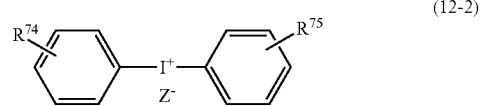

(12-2)

In the general formulae (12-1) and (12-2), $R^{71}$, $R^{72}$, $R^{73}$, $R^{74}$, and $R^{75}$ represent a hydrogen atom, an alkyl group having C1-6, an alkoxyl group having C1-6, a hydroxyl group, or a halogen atom independently from each other. Z⁻ represents HO⁻, R—COO⁻ (R represents an alkyl group having C1-6, an aryl group having C6-11, or an alkaryl group having C7-12), or an anion represented by the following general formula (12-3):

[Chemical Formula 68]

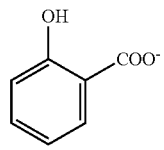

(12-3)

Specific examples of the radiation degradable basic compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total mass of the solid component, more preferably 0.01 to 10% by mass, still more preferably 0.01 to 5% by mass, and particularly preferably 0.01 to 3% by mass. Within the above range, a decrease in resolution, and deterioration of the pattern shape and the dimension fidelity or the like can be further prevented. Moreover, even if the post exposure delay time from electron beam irradiation to heating after radiation irradiation becomes longer, the shape of the pattern upper layer portion is not deteriorated. When the content is 10% by mass or less, a decrease in sensitivity, and developability of the unexposed portion or the like can be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition has extremely excellent process stability.

To the resist composition of the present embodiment, within the range of not inhibiting the purpose of the present embodiment, if required, as the other component (F), one kind or two kinds or more of various additive agents such as a dissolution promoting agent, a dissolution controlling agent, a sensitizing agent, a surfactant and an organic carboxylic acid or an oxo acid of phosphor or derivative of the oxo acid of phosphor can be added.

Dissolution Promoting Agent

A low molecular weight dissolution promoting agent is a component having a function of increasing the solubility of a compound represented by the formula (1) in a developing solution to moderately increase the dissolution rate upon developing, when the solubility of the compound is too low. The low molecular weight dissolution promoting agent can be used, within the range of not deteriorating the effect of the present invention. Examples of the above dissolution promoting agent include a low molecular weight phenolic compound. Examples thereof include bisphenols and tris(hydroxyphenyl)methane. These dissolution promoting agents can be used alone or in mixture of two or more kinds. The content of the dissolution promoting agent, which is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

Dissolution Controlling Agent

The dissolution controlling agent is a component having a function of controlling the solubility of the compound represented by the formula (1) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

Examples of the dissolution controlling agent include, but not particularly limited to, aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent, which is not particularly limited, but is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

Sensitizing Agent

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent include, but not particularly limited to, benzophenones, biacetyls, pyrenes, phenothiazines, and fluorenes. These sensitizing agents can be used alone or in two or more kinds. The content of the sensitizing agent, which is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

Surfactant

The surfactant is a component having a function of improving coatability and striation of the resist composition of the present embodiment, and developability of a resist or the like. Such a surfactant is not particularly limited, and may be any of anionic, cationic, nonionic or amphoteric. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Fat Chemical Industry Co., Ltd.). The content of the surfactant, which is not particularly limited, but is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

Organic Carboxylic Acid, or Oxo Acid of Phosphor or Derivative Thereof

For the purpose of prevention of sensitivity deterioration or improvement of a resist pattern shape and post exposure delay stability or the like, and as an additional optional component, the resist composition of the present embodiment may contain an organic carboxylic acid or an oxo acid of phosphor or derivative thereof. The composition can be used in combination with the acid diffusion controlling agent, or may be used alone. As the organic carboxylic acid, for example, malonic acid, citric acid, malic acid, succinic acid, benzoic acid, and salicylic acid, or the like are preferable. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among them, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

Other Additive Agent

Furthermore, the resist composition of the present embodiment can contain one kind or two kinds or more of additive agents other than the dissolution controlling agent, sensitizing agent, and surfactant, within the range of not inhibiting the purpose of the present invention, if required. Examples of such an additive agent include a dye, a pigment, and an adhesion aid. For example, the composition contains the dye or the pigment, and thereby a latent image of the exposed portion can be visualized and influence of halation upon exposure can be alleviated, which is preferable. The composition contains the adhesion aid, and thereby adhesiveness to a substrate can be improved, which is preferable. Furthermore, examples of other additive agent include a halation preventing agent, a storage stabilizing agent, a defoaming agent, and a shape improving agent. Specific examples thereof include 4-hydroxy-4'-methylchalkone.

The total content of the optional component (F) is preferably 0 to 49% by mass of the total mass of the solid component, more preferably 0 to 5% by mass, still more preferably 0 to 1% by mass, and particularly preferably 0% by mass.

The content ratio of the compound represented by the formula (1) and/or the compound represented by the formula (2), the acid generating agent (C), the acid crosslinking agent (G), the acid diffusion controlling agent (E), and the optional component (F) (compound represented by the formula (1) and/or compound represented by the formula (2)/acid generating agent (C)/acid crosslinking agent (G)/acid diffusion controlling agent (E)/optional component (F)) in the resist composition of the present embodiment is preferably 50 to 99.4/0.001 to 49/0.5 to 49/0.001 to 49/0 to 49 in % by mass based on the solid content, more preferably 55 to 90/1 to 40/0.5 to 40/0.01 to 10/0 to 5, still more preferably 60 to 80/3 to 30/1 to 30/0.01 to 5/0 to 1, and particularly preferably 60 to 70/10 to 25/2 to 20/0.01 to 3/0.

The content ratio of each component is selected from each range such that the summation thereof is 100% by mass. By the above content ratio, performance such as sensitivity, resolution, and developability becomes more excellent.

Examples of a method for preparing the resist composition of the present embodiment include, but not particularly limited to, a method of dissolving each component in a solvent upon use into a homogenous solution, and then if required, filtering through a filter or the like with a pore diameter of about 0.2 μm, for example.

Examples of the solvent used in the preparation of the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. These solvents can be used alone or in combination of two or more kinds.

The resist composition of the present embodiment can contain a resin within the range of not inhibiting the purpose of the present invention. Examples of the resin include, but not particularly limited to, a novolac resin, polyvinyl phenols, polyacrylic acid, polyvinyl alcohol; a styrene-maleic anhydride resin, and a polymer containing acrylic acid, vinyl alcohol or vinylphenol as a monomeric unit, or derivative thereof. The content of the resin, which is not particularly limited, but is arbitrarily adjusted according to the kind of the compound represented by the formula (1) to be used, is preferably 30 parts by mass or less per 100 parts by mass of the compound, more preferably 10 parts by mass or less, still more preferably 5 parts by mass or less, and particularly preferably 0 part by mass.

[Resist Pattern Formation Method]

A resist pattern formation method according to the present embodiment is not particularly limited. Suitable examples of the method include a method including steps of forming a resist film on a substrate using the above resist composition of the present embodiment, exposing the formed resist film, and developing the resist film to form a resist pattern.

The resist pattern of the present embodiment can be formed as an upper layer resist in a multilayer process.

In order to form a resist pattern, a resist film is formed by coating a conventionally publically known substrate with the resist composition of the present embodiment using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples include a substrate made of a metal such as a silicon wafer, copper, chromium, iron and aluminum, and a glass substrate. Examples of a wiring pattern material include copper, aluminum, nickel, and gold. Also if required, the substrate may be a substrate having an inorganic and/or organic film provided thereon. Examples of the inorganic film include an inorganic antireflection film (inorganic BARC). Examples of the organic film include an organic antireflection film (organic BARC). Surface treatment with hexamethylene disilazane or the like may be conducted.

Next, the coated substrate is heated if required. The heating conditions vary according to the content composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like.

In the present embodiment, in order to stably form a fine pattern with a high degree of accuracy in exposure, the resist film is preferably heated after radiation irradiation. The heating conditions vary according to the compounding composition of the resist composition, or the like, but are preferably 20 to 250° C., and more preferably 20 to 150° C.

Next, by developing the exposed resist film in a developing solution, a predetermined resist pattern is formed. As the developing solution, a solvent having a solubility parameter (SP value) close to that of the compound of the formula (1) to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include, but not particularly limited to, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include, but not particularly limited to, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include, but not particularly limited to, an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include, but not particularly limited to, dioxane and tetrahydrofuran in addition to the glycol ether-based solvents.

Examples of the amide-based solvent which can be used include, but not particularly limited to, N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include, but not particularly limited to, an aromatic hydrocarbon-based solvent such as toluene and xylene; and an aliphatic hydrocarbon-based solvent such as pentane, hexane, octane, and decane.

A plurality of these solvents may be mixed, or the solvent may be used by mixing the solvent with a solvent other than those described above or water within the range having performance. However, in order to sufficiently exhibit the effect of the present invention, the water content ratio as the whole developing solution is less than 70% by mass, preferably less than 50% by mass, more preferably less than 30% by mass, and still more preferably less than 10% by mass. Particularly preferably, the developing solution is substantially moisture free. That is, the content of the organic solvent in the developing solution is not particularly limited, but is 30% by mass or more and 100% by mass or less based on the total amount of the developing solution, preferably 50% by mass or more and 100% by mass or less, more preferably 70% by mass or more and 100% by mass or less, still more preferably 90% by mass or more and 100% by mass or less, and particularly preferably 95% by mass or more and 100% by mass or less.

Examples of the alkaline aqueous solution include, but not particularly limited to, an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. S62-36663, S61-226746, S61-226745, S62-170950, S63-34540, H7-230165, H8-62834, H9-54432, and H9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is more preferably used.

The amount of the surfactant used is usually 0.001 to 5% by mass based on the total amount of the developing solution, preferably 0.005 to 2% by mass, and more preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Yet still more preferably, after development, a step of rinsing the film by using a rinsing solution containing a monohydric alcohol is conducted. Particularly preferably, after development, a step of rinsing the film by using a rinsing solution containing a monohydric alcohol having C5 or more is conducted. The time for rinsing the pattern is not particularly limited, but is preferably 10 seconds to 90 seconds.

Herein, examples of the monohydric alcohol used in the rinsing step after development include a linear, branched or cyclic monohydric alcohol. Specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like can be used. As the particularly preferable monohydric alcohol having C5 or more, 1-hexanol, 2-hexanol, 4-methyl-2-pentanol, 1-pentanol, and 3-methyl-1-butanol or the like can be used.

A plurality of these components may be mixed, or the component may be used by mixing the component with an organic solvent other than those described above.

The water content ratio in the rinsing solution is not particularly limited, but is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and much more preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the plating method include copper plating, solder plating, nickel plating, and gold plating.

The remaining resist pattern after etching can be peeled by an organic solvent. Examples of the organic solvent include PGMEA (propylene glycol monomethyl ether acetate), PGME (propylene glycol monomethyl ether), and EL (ethyl lactate). Examples of the peeling method include a dipping method and a spraying method. A wiring substrate having a resist pattern formed thereon may be a multilayer wiring substrate, and may have a small diameter through hole.

The wiring substrate obtained in the present embodiment can also be formed by a method for forming a resist pattern, then depositing a metal in vacuum, and subsequently dissolving the resist pattern in a solution, i.e., a liftoff method.

[Polyphenolic Compound]

The polyphenolic compound of the present embodiment is a compound represented by the general formula (3) (hereinafter, may be referred to as a "polyphenolic compound A") or a polyphenolic compound represented by the general formula (4) (hereinafter, may be referred to as a "polyphenolic compound B"):

[Chemical Formula 69]

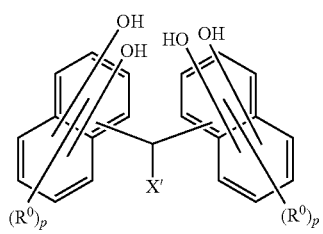

(3)

[Chemical Formula 70]

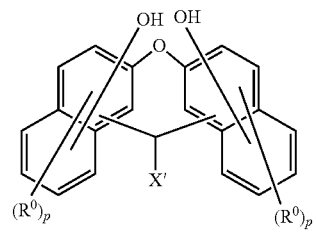

(4)

wherein X' are each independently a hydrogen atom or a C1-18 monovalent substituent; $R^0$ are each independently a C1-4 alkyl group or a halogen atom and may be the same or different on the same naphthalene ring; and p is an integer of 0 to 5.

The polyphenolic compound of the present embodiment has a naphthalene skeleton and is thereby excellent in heat resistance. The polyphenolic compound of the present embodiment has two hydroxyl groups per naphthalene ring and therefore exhibits an effect of being also excellent in solubility in a safe solvent in addition to heat resistance.

The position of the hydroxyl groups on the naphthalene ring is not particularly limited and is preferably position 1,5, 1,6, 1,7, 2,3, 2,7, or 2,6 in terms of industrial usability of raw materials, and more preferably position 2,6 in terms of higher solubility in a safe solvent and low crystallinity.

That is, the above general formula (30) or (40) is preferable.

(Polyphenolic Compound A and Method for Producing the Compound)

The polyphenolic compound A of the present embodiment is represented by the above general formula (3).

In the general formula (3), X' is a hydrogen atom or a C1-18 monovalent substituent. Examples of the C1-18 monovalent substituent include, but not particularly limited to, a methyl group, an ethyl group, a propyl group, a butyl group, a pentyl group, a hexyl group, a heptyl group, an octyl group, a nonyl group, a decyl group, an octadecyl group, a cyclopropyl group, a cyclohexyl group, an adamantyl group, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group.

Of these, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, or a pyrenyl group having an aromatic ring skeleton is preferable from the viewpoint of heat resistance. Among them, a biphenyl group, a terphenyl group, a naphthyl group, an anthracyl group, a phenanthryl group, or a pyrenyl group is particularly preferable.

In the general formula (3), $R^0$ is a C1-4 alkyl group or a halogen atom. Examples thereof include a methyl group, an ethyl group, a propyl group, a butyl group, a fluorine atom, a chlorine atom, a bromine atom, and an iodine atom.

In the general formula (3), p is an integer of 0 to 5 and is preferably 0 or 1 in terms of solubility.

The polyphenolic compound A of the present embodiment can be produced by a publicly known method, and the production method is not limited. For example, a production method of reacting a compound represented by the general formula (5) with a C1-19 aldehyde in the presence of an acid catalyst produces only a few by-products and can efficiently produce the compound, which is particularly preferable.

[Chemical Formula 71]

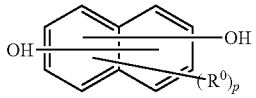
(5)

wherein R⁰, p, and the like are the same as above.

As a specific example of the method for producing the polyphenolic compound A of the present embodiment, 2,6-naphthalenediol can be reacted with 4-biphenylcarboxaldehyde in the presence of a sulfuric acid catalyst at 30° C. to produce a compound represented by the formula (3'):

[Chemical Formula 72]

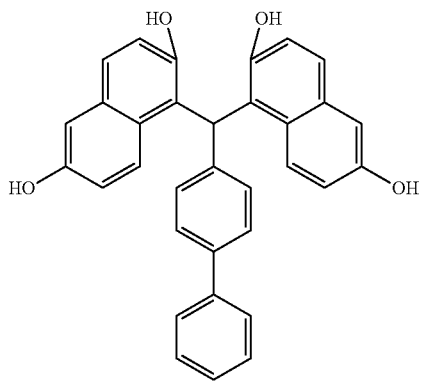
(3')

The compound represented by the above general formula (5) can be used without particular limitations as long as the compound has a dihydroxynaphthalene skeleton. Examples thereof include 2,6-naphthalenediol, methyl-2,6-naphthalenediol, ethyl-2,6-naphthalenediol, propyl-2,6-naphthalenediol, butyl-2,6-naphthalenediol, fluoro-2,6-naphthalenediol, chloro-2,6-naphthalenediol, bromo-2,6-naphthalenediol, iodo-2,6-naphthalenediol, compounds in which diol in the above compounds is attached to position 1,5, compounds in which diol is attached to position 1,6, compounds in which diol is attached to position 1,7, compounds in which diol is attached to position 2,3, and compounds in which diol in the above compounds is attached to position 2,7. One kind or two or more kinds thereof can be used. By having the naphthalene skeleton, the polyphenolic compound can be expected to improve performance in terms of heat resistance over polyphenol produced using a dihydroxy compound having a benzene ring skeleton.

The position of the hydroxyl groups in the naphthalenediol used is not particularly limited and can be selected according to, for example, the structure of the objective polyphenolic compound. In the case of producing, for example, a preferable polyphenolic compound (30), use of naphthalenediol having hydroxyl groups at positions 2,6, i.e., a compound represented by the following general formula (50), enables highly selective reaction, and thereby the objective compound can be obtained at high yields.

[Chemical Formula 73]

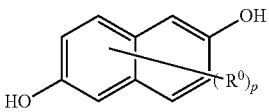
(50)

wherein R⁰, p, and the like are the same as above.

The compound represented by the above general formula (50) is not particularly limited, and, for example, 2,6-naphthalenediol, methyl-2,6-naphthalenediol, ethyl-2,6-naphthalenediol, propyl-2,6-naphthalenediol, butyl-2,6-naphthalenediol, fluoro-2,6-naphthalenediol, chloro-2,6-naphthalenediol, bromo-2,6-naphthalenediol, or iodo-2,6-naphthalenediol is used. These are easily available as reagents.

In the method for producing the polyphenolic compound A of the present embodiment, the structure of the substituent X' in the produced polyphenolic compound of the general formula (3) is determined depending on the kind of the C1-19 aldehyde used. Examples of the aldehyde include formaldehyde, acetaldehyde, propionaldehyde, butylaldehyde, pentylaldehyde, hexylaldehyde, heptylaldehyde, octylaldehyde, nonylaldehyde, decylaldehyde, octadecylaldehyde, cyclopropylaldehyde, cyclohexylaldehyde, adamantylcarboxaldehyde, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxaldehyde, terphenylcarboxaldehyde, naphthalenecarboxaldehyde, anthracenecarboxaldehyde, phenanthrenecarboxaldehyde, and pyrenecarboxaldehyde. Of these, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxaldehyde, terphenylcarboxaldehyde, naphthalenecarboxaldehyde, anthracenecarboxaldehyde, phenanthrenecarboxaldehyde, or pyrenecarboxaldehyde having an aromatic ring skeleton is preferable from the viewpoint of heat resistance. Among them, biphenylcarboxaldehyde, terphenylcarboxaldehyde, naphthalenecarboxaldehyde, anthracenecarboxaldehyde, phenanthrenecarboxaldehyde, or pyrenecarboxaldehyde is particularly preferable.

These C1-19 aldehydes are easily available as industrial products or reagents.

As the C1-19 aldehyde, one kind or two or more kinds can be used.

The acid catalyst used in the method for producing the polyphenolic compound A of the present embodiment is not particularly limited and can be arbitrarily selected from well known inorganic acids and organic acids. Examples thereof include: inorganic acids such as hydrochloric acid, sulfuric acid, phosphoric acid, hydrobromic acid, and hydrofluoric acid; organic acids such as oxalic acid, formic acid, p-toluenesulfonic acid, methanesulfonic acid, trifluoroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. From the viewpoint of production such as easy availability and handleability, hydrochloric acid or sulfuric acid is preferable.

As the acid catalyst, one kind or two or more kinds can be used.

Next, conditions for the reaction of the compound represented by the above general formula (5) with the C1-19 aldehyde will be described in detail.

By using 1 mol to an excess of the compound of the general formula (5) and 0.001 to 1 mol of the acid catalyst, based on 1 mol of the C1-19 aldehyde in the reaction, the reaction proceeds at 20 to 60° C. at normal pressure for about 20 minutes to 100 hours. This reaction may also form the compound represented by the above general formula (4) and however, can yield the polyphenolic compound A represented by the general formula (3) of the present embodiment as a main component by controlling the reaction temperature within relatively low temperatures of 10 to 60° C.

After the reaction terminates, the target component is isolated by a publicly known method. For example, the reaction solution is concentrated. The reaction product is precipitated by the addition of pure water. The reaction solution is cooled to room temperature. Then, the precipitates are separated by filtration. The obtained solid matter is filtered, dried, and then separated and purified from by-products by column chromatography. The solvent is distilled off, followed by filtration and drying to obtain the objective compound represented by the general formula (3).

(Polyphenolic Compound B and Method for Producing the Compound)

The polyphenolic compound B of the present embodiment is represented by the above general formula (4):

[Chemical Formula 74]

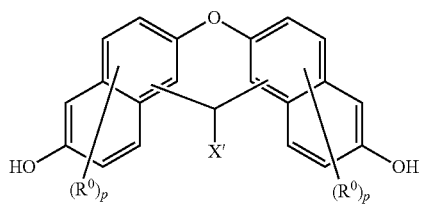

(4)

wherein X' are each independently a hydrogen atom or a C1-18 monovalent substituent; $R^0$ are each independently a C1-4 alkyl group or a halogen atom and may be the same or different on the same naphthalene ring; and p is an integer of 0 to 5.

In the general formula (4), X' is a hydrogen atom or a C1-18 monovalent substituent. Examples of the C1-18 monovalent substituent include, but not particularly limited to, a methyl group, an ethyl group, a propyl group, a butyl group, a pentyl group, a hexyl group, a heptyl group, an octyl group, a nonyl group, a decyl group, an octadecyl group, a cyclopropyl group, a cyclohexyl group, an adamantyl group, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group of these, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, or a pyrenyl group having an aromatic ring skeleton is preferable from the viewpoint of heat resistance. Among them, a biphenyl group, a terphenyl group, a naphthyl group, an anthracyl group, a phenanthryl group, or a pyrenyl group is particularly preferable.

$R^0$ is a C1-4 alkyl group or a halogen atom. Examples thereof include a methyl group, an ethyl group, a propyl group, a butyl group, a fluorine atom, a chlorine atom, a bromine atom, and an iodine atom.

In the general formula (4), p is an integer of 0 to 5 and is preferably 0 or 1 in terms of solubility.

The polyphenolic compound B of the present embodiment can be produced by a publicly known method, and the production method is not limited. For example, a production method of reacting a compound represented by the above general formula (5) with a C1-19 aldehyde in the presence of an acid catalyst produces only a few by-products and can efficiently produce the compound, which is particularly preferable.

As a specific example of the method for producing the polyphenolic compound B of the present embodiment, 2,6-naphthalenediol can be reacted with 4-biphenylcarboxaldehyde in the presence of a sulfuric acid catalyst at 100° C. to produce a compound represented by the formula (4'):

[Chemical Formula 75]

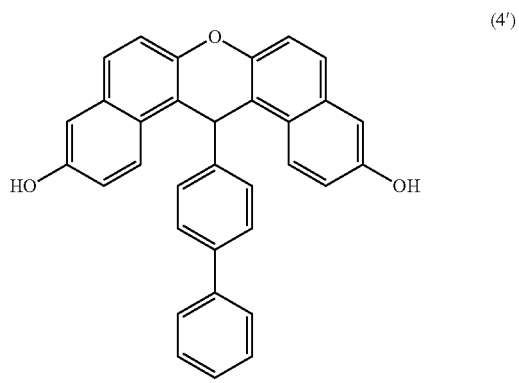

(4')

The same compound represented by the above general formula (5) as used in the method for producing the above polyphenolic compound A can be used in the production method of the present embodiment.

The same C1-19 aldehyde and acid catalyst as used in the method for producing the above polyphenolic compound A can be used in the method for producing the polyphenolic compound B of the present embodiment.

Next, conditions for the reaction of the compound represented by the general formula (5) with the C1-19 aldehyde will be described in detail.

By using 1 mol to an excess of the compound of the general formula (5) and 0.001 to 1 mol of the acid catalyst, based on 1 mol of the C1-19 aldehyde in the reaction, the reaction proceeds at 60 to 120° C. at normal pressure for about 20 minutes to 100 hours. This reaction may also form the compound represented by the general formula (3) and however, can yield the polyphenolic compound B represented by the general formula (4) of the present embodiment as a main component by controlling the reaction temperature within relatively high temperatures of 60 to 120° C.

A method for isolating the target component after the reaction terminates is not particularly limited, and the same method as in the method for producing the above polyphenolic compound A can be adopted.

(Physical Properties of Polyphenolic Compound)

In terms of heat resistance, the thermal decomposition temperature of the polyphenolic compound of the present embodiment measured by differential scanning calorimetry (DSC) is preferably 200 to 500° C.

In terms of heat resistance, the glass transition temperature of the polyphenolic compound of the present embodiment measured by differential scanning calorimetry (DSC) is preferably 100 to 300° C.

[Alcoholic Compound]

The alcoholic compound of the present embodiment is an alcohol represented by the general formula (6) (hereinafter, may be referred to as an "alcoholic compound A") or an alcoholic compound represented by the general formula (7) (hereinafter, may be referred to as an "alcoholic compound B").

[Chemical Formula 76]

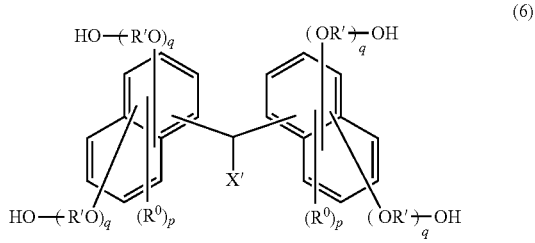

(6)

[Chemical Formula 77]

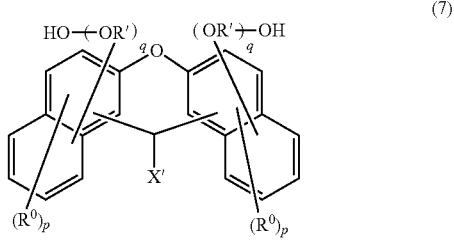

(7)

wherein X', R', q, p, and the like are the same as above.

The alcoholic compound of the present embodiment has the above naphthalene skeleton and is thereby excellent in heat resistance.

The position of the hydroxyl groups on the naphthalene ring is not particularly limited and is preferably position 1,5, 1,6, 1,7, 2,3, 2,7, or 2,6 in terms of industrial usability of raw materials, and more preferably position 2,6 in terms of higher solubility in a safe solvent and low crystallinity.

That is, the above general formula (60) or (70) is preferable.

[Chemical Formula 78]

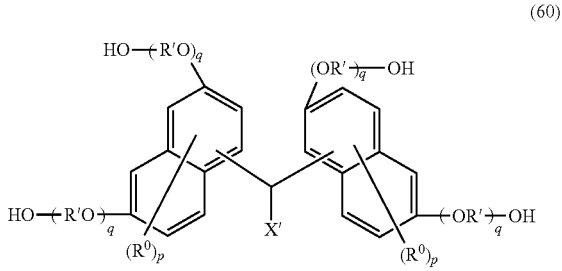

(60)

[Chemical Formula 79]

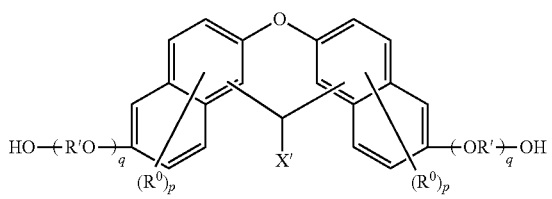

(70)

wherein X', R', R⁰, q, p, and the like are the same as above.

(Alcoholic Compound A and Method for Producing the Compound)

The alcoholic compound A of the present embodiment is represented by the above general formula (6).

In the above general formula (6), X' is a hydrogen atom or a C1-18 monovalent substituent. Examples of the C1-18 monovalent substituent include, but not particularly limited to, a methyl group, an ethyl group, a propyl group, a butyl group, a pentyl group, a hexyl group, a heptyl group, an octyl group, a nonyl group, a decyl group, an octadecyl group, a cyclopropyl group, a cyclohexyl group, an adamantyl group, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group of these, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, or a pyrenyl group having an aromatic ring skeleton is preferable as X' from the viewpoint of heat resistance. Among them, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, or a pyrenyl group is particularly preferable.

In terms of mechanical characteristics, the compound preferably has no cardo structure. Particularly, a fluorene compound having a cardo structure has a bulky structure and may have poor mechanical physical properties.

$R^0$ are each independently a C1-4 alkyl group or a halogen atom. Examples thereof include a methyl group, an ethyl group, a propyl group, a butyl group, a fluorine atom, a chlorine atom, a bromine atom, and an iodine atom. $R^0$ may be the same or different on the same naphthalene ring.

R' are each independently a C1-4 alkylene group. Examples thereof include, but not particularly limited to, a methylene group, an ethylene group, a propylene group, a trimethylene group, a butylene group, and a tetramethylene group. R' may be the same or different on the same naphthalene ring.

p are each independently an integer of 0 to 5 and are each preferably an integer of 0 or 1 in terms of heat resistance and solubility.

q are each independently an integer of 1 or larger and are each preferably an integer of 1 or 2 in terms of heat resistance, solubility, and mechanical characteristics.

The alcoholic compound A of the present embodiment can be produced by a publicly known method, and the production method is not particularly limited. For example, a method of reacting a compound represented by the above general formula (3) with an alkylene oxide introducing agent in the presence of a basic catalyst produces only a few by-products and can efficiently produce the compound, which is particularly preferable. Examples of a method for isolating the obtained compound include, but not limited to, a method of obtaining a crude crystal by crystallization or the like, then dissolving the crude crystal in an organic solvent, adding a strong base to the solution, and stirring the mixture at normal pressure for about 20 minutes to 100 hours.

As a specific example of the method for producing the alcoholic compound A of the present embodiment, 1 mol of the compound represented by the formula (3'), 2.6 mol of 2-chloroethyl acetate, and 5.2 mol of potassium carbonate are placed in a 3 L flask and reacted in a dimethylformamide solvent at 90° C. while heating using an oil bath in the dimethylformamide. Subsequently, the reaction solution is cooled to crystallize. The obtained crude crystal is isolated and refluxed together with sodium hydroxide in a methanol solvent for 4 hours. A crystal precipitated by cooling in air can be filtered and rinsed to produce a compound represented by the formula (6').

[Chemical Formula 80]

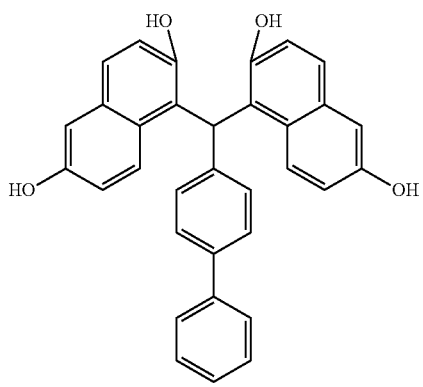

(3')

[Chemical Formula 81]

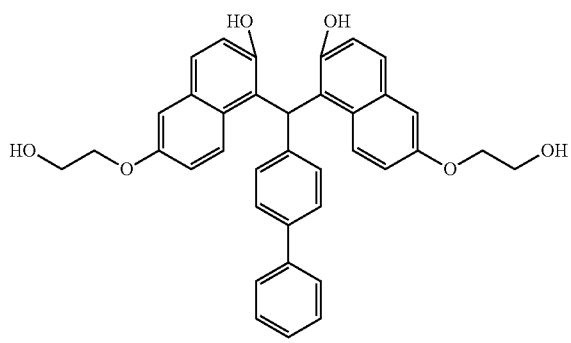

(6')

A method for producing the compound represented by the above general formula (3) used in the present embodiment is not particularly limited and is as described in the above section [Polyphenolic Compound].

The alkylene oxide introducing agent used in the present embodiment can be used without particular limitations as long as it can introduce a hydroxy polyalkylene oxide group represented by the general formula (80) to a hydroxyl group in the compound represented by the general formula (3). Examples thereof include acetic acid-2-haloethyl, alkylene oxide, and alkylene carbonate.

As the alkylene oxide introducing agent, one kind or two or more kinds can be used.

[Chemical Formula 82]

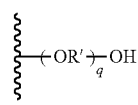

(80)

wherein R' and q are the same as above.

Examples of the acetic acid-2-haloethyl include, but not particularly limited to, acetic acid-2-chloroethyl, acetic acid-2-bromoethyl, and acetic acid-2-iodoethyl. In the case of using the acetic acid-2-haloethyl, after an acetoxyethyl group is introduced, deacylation reaction occurs, thereby introducing a hydroxyethyl group.

Examples of the alkylene oxide include, but not particularly limited to, ethylene oxide, propylene oxide, and butylene oxide.

Examples of the alkylene carbonate include, but not particularly limited to, ethylene carbonate, propylene carbonate, and butylene carbonate. In the case of using the alkylene carbonate, after the alkylene carbonate is added, decarboxylation reaction occurs, thereby introducing alkylene oxide.

The basic catalyst used in the reaction of the compound of the general formula (3) of the present embodiment with the alkylene oxide introducing agent is not particularly limited and can be arbitrarily selected from well known basic catalysts. Examples thereof include: inorganic bases such as metal hydroxides (e.g., alkali metal or alkaline earth metal hydroxides such as sodium hydroxide and potassium hydroxide), metal carbonates (e.g., alkali metal or alkaline earth metal carbonates such as sodium carbonate and potassium carbonate), and alkali metal or alkaline earth metal bicarbonates such as sodium bicarbonate and potassium bicarbonate; and organic bases such as amines (for example, tertiary amines (trialkylamines such as triethylamine, aromatic tertiary amines such as N,N-dimethylaniline, and heterocyclic tertiary amines such as 1-methylimidazole) and carboxylic acid metal salts (e.g., acetic acid alkali metal or alkaline earth metal salts such as sodium acetate and calcium acetate). From the viewpoint of production such as easy availability and handleability, sodium carbonate or potassium carbonate is preferable.

As the basic catalyst, one kind or two or more kinds can be used.

Next, conditions for the reaction of the compound represented by the general formula (3) with the alkylene oxide introducing agent will be described in detail.

The reaction conditions are not particularly limited. For example, by using 1 mol to an excess of the alkylene oxide introducing agent and 0.001 to 1 mol of the basic catalyst, based on 1 mol of the compound represented by the general formula (3), the reaction proceeds at 20 to 150° C. at normal pressure for about 20 minutes to 100 hours. After the reaction, the target component is purified by a publicly known method. Examples of the purification method include, but not particularly limited to, a method of precipitating a crystal by cooling in ice water or the like, and isolating the crystal to obtain a crude crystal.

Subsequently, the crude crystal is dissolved in an organic solvent, and a strong base is added to the solution and reacted at normal pressure at 20 to 150° C. for about 20 minutes to 100 hours. After the reaction, the target component is isolated by a publicly known method. Examples thereof include a method of concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the objective compound represented by the general formula (6).

(Alcoholic Compound B and Method for Producing the Compound)

The alcoholic compound B of the present embodiment is represented by the above general formula (7).

X', $R^0$, R', p, and q are the same as above.

The alcoholic compound B of the present embodiment can be produced by a publicly known method, and the production method is not particularly limited. For example, a method of reacting a compound represented by the above general formula (4) with an alkylene oxide introducing agent in the presence of a basic catalyst produces only a few by-products and can efficiently produce the compound, which is particularly preferable.

Examples of a method for isolating the obtained compound include, but not limited to, a method of obtaining a crude crystal by crystallization or the like, then dissolving the crude crystal in an organic solvent, adding a strong base to the solution, and stirring the mixture at normal pressure for about 20 minutes to 100 hours.

As a specific example of the method for producing the alcoholic compound B of the present embodiment, 1 mol of the compound represented by the formula (4'), 2.6 mol of 2-chloroethyl acetate, and 5.2 mol of potassium carbonate are placed in a 3 L flask and reacted in a dimethylformamide solvent at 90° C. while heating using an oil bath in the dimethylformamide. Subsequently, the reaction solution is cooled to crystallize. The obtained crude crystal is isolated and refluxed together with sodium hydroxide in a methanol solvent for 4 hours. A crystal precipitated by cooling in air can be filtered and rinsed to produce a compound represented by the formula (7').

[Chemical Formula 83]

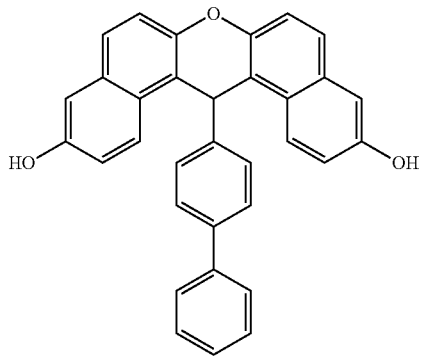

(4')

[Chemical Formula 84]

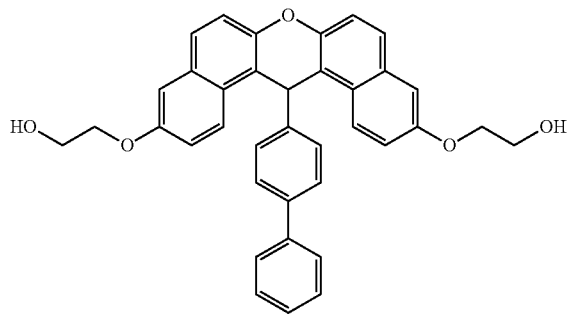

(7')

A method for producing the compound represented by the above general formula (4) used in the method for producing the alcoholic compound of the present embodiment is not particularly limited and is as described in the above section [Polyphenolic Compound].

The alkylene oxide introducing agent and the basic catalyst used in the present embodiment are not particularly limited, and the same ones that can be used in the production of the above alcoholic compound A can be used.

Next, conditions for the reaction of the compound represented by the general formula (4) with the alkylene oxide introducing agent will be described in detail.

The reaction conditions are not particularly limited. For example, by using 1 mol to an excess of the alkylene oxide introducing agent and 0.001 to 1 mol of the basic catalyst, based on 1 mol of the compound represented by the general formula (4), the reaction proceeds at 20 to 150° C. at normal pressure for about 20 minutes to 100 hours. After the reaction, the target component is purified by a publicly known method. Examples of the purification method include, but not particularly limited to, a method of precipitating a crystal by cooling in ice water or the like, and isolating the crystal to obtain a crude crystal.

Subsequently, the crude crystal is dissolved in an organic solvent, and a strong base is added to the solution and reacted at normal pressure at 20 to 150° C. for about 20 minutes to 100 hours. After the reaction, the target component is isolated by a publicly known method. Examples thereof include a method of concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the objective compound represented by the general formula (1).

(Physical Properties of Alcoholic Compound)

In terms of heat resistance, the thermal decomposition temperature of the alcoholic compound of the present embodiment measured by differential scanning calorimetry (DSC) is preferably 200 to 500° C.

In terms of heat resistance, the glass transition temperature of the alcoholic compound of the present embodiment measured by differential scanning calorimetry (DSC) is preferably 50 to 200° C.

EXAMPLES

The present embodiment will be more specifically described with reference to examples below. However, the present invention is not limited to these examples.

Hereinafter, a method for measuring a compound in examples and a method for evaluating resist performance or the like are shown.

<Measurement Method>

(1) Structure of Compound

The structure of a compound was confirmed using Advance600II spectrometer manufactured by Bruker Corporation according to $^1$H-NMR measurement under the following conditions:

Frequency: 400 MHz

Solvent: d6-DMSO (except for Synthesis Example 4)

Internal standard: TMS

Measurement temperature: 23° C.

(2) Molecular Weight of Compound

A compound was measured using Agilent 5975/6890N manufactured by Agilent Corporation according to GC-MS analysis or measured using Acquity UPLC/MALDI-Synapt HDMS manufactured by Water Corporation according to LC-MS analysis.

(3) Thermal Decomposition Temperature

The apparatus EXSTAR6000DSC (trade name) manufactured by SII NanoTechnology Inc. was used. About 5 mg of each sample was placed in a non-sealed container made of aluminum, and the temperature was raised to 500° C. at the rate of temperature rise of 10° C./min in a nitrogen gas stream (30 mL/min). The temperature corresponding to a descending peak appeared in the baseline was defined as the thermal decomposition temperature.

(4) Glass Transition Temperature

The apparatus EXSTAR6000DSC (trade name) manufactured by SII NanoTechnology Inc. was used. About 5 mg of each sample was placed in a non-sealed container made of aluminum, and the temperature was raised to 300° C. at the rate of temperature rise of 10° C./min in a nitrogen gas stream (30 mL/min). After the non-sealed container made of aluminum was quenched, again the temperature was raised to 300° C. at the rate of temperature rise of 10° C./min in a nitrogen gas stream (30 mL/min), thereby performing DSC measurement. The temperature corresponding to the middle point (where the specific heat was changed into the half) of a region in which a discontinuous portion appeared in the baseline was defined as the glass transition point.

(5) Dissolution Rate of Amorphous Film (Before and after Exposure) in Developing Solution An amorphous film was dipped in a developing solution at 23° C. for a predetermined time, and film thicknesses before and after dipping were visually confirmed to determine a dissolution rate.

[Evaluation Method]

(1) Solubility of Compound in Methyl Ethyl Ketone (MEK)

The solubility of the compound in MEK was evaluated according to the following standard using the dissolution amount in MEK at 23° C. For the measurement of the dissolution amount, the compound was precisely weighed in a test tube at 23° C.; and the target solvent was added to the compound so that a predetermined concentration of the liquid to be obtained was set; a ultrasonic wave was applied to the liquid in an ultrasonic washing machine for 30 minutes; and the state of the resulting liquid was visually evaluated.

Evaluation A: 50% by weight or more
Evaluation B: 10% by weigh or more and less than 50% by weight
Evaluation C: less than 10% by weight (2) Solubility Test of Compound in Safe Solvent The solubility of the compound in PGME and PGMEA was evaluated according to the following standard using the dissolution amount in each solvent. For the measurement of the dissolution amount, the compound was precisely weighed in a test tube at 23° C.; and the target solvent was added to the compound so that a predetermined concentration of the liquid to be obtained was set; a ultrasonic wave was applied to the liquid in an ultrasonic washing machine for 30 minutes; and the state of the resulting liquid was visually evaluated.

A: 5.0% by weight ≤dissolution amount
B: 3.0% by weight ≤dissolution amount <5.0% by weight
C: dissolution amount <3.0% by weight (3) Heat Resistance Each prepared resist composition was evaluated for its heat resistance by the following procedures.

A clean silicon wafer was spin coated with a resist, and then baked in an oven of 110° C. to form a resist film with a thickness of 60 nm. The film was visually observed. A good film having no defect was evaluated as having good heat resistance (evaluation: ○ (good)).

(4) Pattern Evaluation of Resist Pattern (Resolution, Shape, LER)

The line and space of each resist pattern was observed by a scanning electron microscope (S-4800 manufactured by Hitachi High-Technologies Corporation). The pattern having the resolution of 30 nm was evaluated for whether or not pattern shape, line edge roughness, and sensitivity were good.

The rectangular pattern shape was evaluated as goodness. For LER (line edge roughness), the distance between the edge and the standard line was measured using a Hitachi SEM Terminal PC V5 Offline Length Measuring Software for Semiconductor (manufactured by Hitachi Science Systems) for arbitrary 300 points in the length direction (0.75 μm) with 50 nm interval and 1:1 line and space to calculate the standard deviation (3σ). The distance of less than 5 nm was evaluated as goodness. The minimum line width of the pattern which could be well formed was used as the resolution of the pattern. The minimum dose amount ($\mu C/cm^2$) when the pattern could be well formed was used as sensitivity. The minimum dose amount of less than 150 $\mu C/cm^2$ was evaluated as goodness.

A resist pattern having good pattern shape, LER, and sensitivity was evaluated as ○ (good). Unsuccessful formation of a resist pattern was evaluated as x (poor).

Synthesis Examples

Synthesis Example 1

Synthesis of BisN-1 (Polyphenolic Compound)

In a container (internal capacity: 100 ml) equipped with a stirrer, a condenser tube, and a burette, 3.20 g (20 mmol) of 2,6-naphthalenediol (reagent manufactured by Sigma-Aldrich Corporation) and 1.82 g (10 mmol) of 4-biphenylcarboxaldehyde (manufactured by Mitsubishi Gas Chemical Company, Inc.) were charged to 30 ml of methyl isobutyl ketone, and 5 ml of 95% sulfuric acid was further added thereto. The reaction solution was stirred at 30° C. for 6 hours to perform reaction. Next, the reaction solution was concentrated. The reaction product was precipitated by the addition of 50 g of pure water. After cooling to room temperature, the precipitates were separated by filtration.

The obtained solid matter was filtered, dried, and then separated and purified by column chromatography to obtain 0.2 g of the objective compound (BisN-1) represented by the following formula.

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The signals of protons at positions 3 and 4 were found as a doublet, thereby confirming that the substitution position of 2,6-naphthalenediol was position 1.

The compound had the thermal decomposition temperature of 250° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 85]

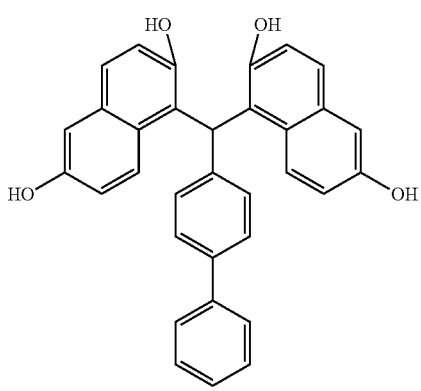

(BisN-1)

Synthesis Example 2

Synthesis of BisN-2 (Polyphenolic Compound)

0.2 g of the objective compound (BisN-2) represented by the following formula was obtained in the same way as in Synthesis Example 1 except that 3.20 g (20 mmol) of 2,6-naphthalenediol was changed to 3.20 g (20 mmol) of 2,7-naphthalenediol (reagent manufactured by Sigma-Aldrich Corporation).

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 250° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 86]

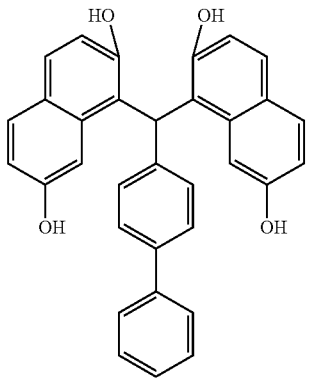

(BisN-2)

Synthesis Example 3

Synthesis of BisN-3 (Polyphenolic Compound)

0.2 g of the objective compound (BisN-3) represented by the following formula was obtained in the same way as in Synthesis Example 1 except that 3.20 g (20 mmol) of 2,6-naphthalenediol was changed to 3.20 g (20 mmol) of 1,5-naphthalenediol (reagent manufactured by Sigma-Aldrich Corporation).

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 250° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 87]

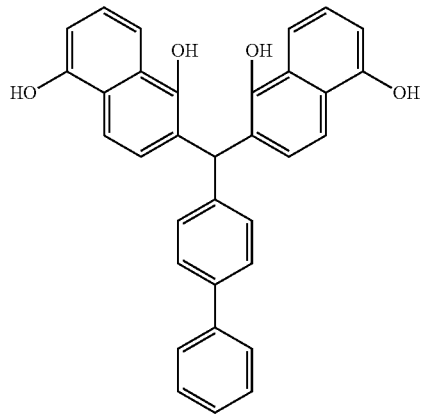

(BisN-3)

Synthesis Example 4

Synthesis of BisN-4 (Polyphenolic Compound)

0.2 g of the objective compound (BisN-4) represented by the following formula was obtained in the same way as in Synthesis Example 1 except that 3.20 g (20 mmol) of 2,6-naphthalenediol was changed to 3.20 g (20 mmol) of 1,6-naphthalenediol (reagent manufactured by Sigma-Aldrich Corporation).

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 250° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 88]

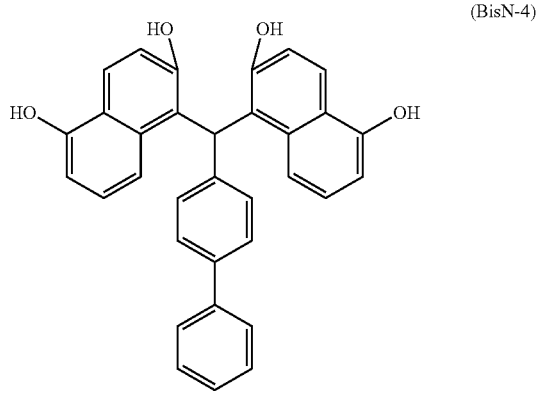

(BisN-4)

Synthesis Example 5

Synthesis of BisN-5 (Polyphenolic Compound)

0.2 g of the objective compound (BisN-5) represented by the following formula was obtained in the same way as in Synthesis Example 1 except that 3.20 g (20 mmol) of 2,6-naphthalenediol was changed to 3.20 g (20 mmol) of 1,7-naphthalenediol (reagent manufactured by Sigma-Aldrich Corporation).

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 250° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 89]

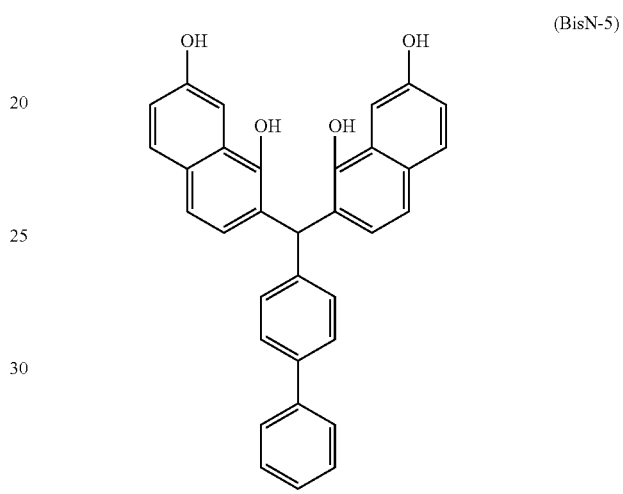

(BisN-5)

Synthesis Example 6

Synthesis of BisN-6 (Polyphenolic Compound)

0.2 g of the objective compound (BisN-6) represented by the following formula was obtained in the same way as in Synthesis Example 1 except that 3.20 g (20 mmol) of 2,6-naphthalenediol was changed to 3.20 g (20 mmol) of 2,3-naphthalenediol (reagent manufactured by Sigma-Aldrich Corporation).

As a result of measuring the molecular weight of the obtained compound by the above method, it was 484.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 250° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 90]

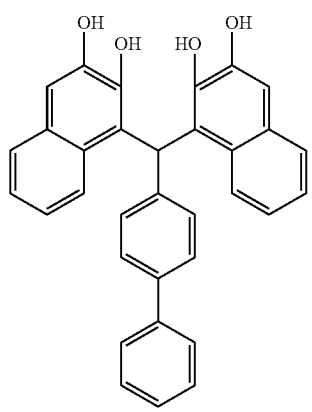

(B is N-6)

Synthesis Example 7

Synthesis of BisN-7 (Polyphenolic Compound)

0.2 g of the objective compound (BisN-7) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 1.56 g (10 mmol) of 1-naphthaldehyde (reagent manufactured by Sigma-Aldrich Corporation).

As a result of measuring the molecular weight of the obtained compound by the above method, it was 458.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (17H, Ph-H), 6.8 (1H, C—H)

The compound had the thermal decomposition temperature of 255° C. and the glass transition point of 135° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 91]

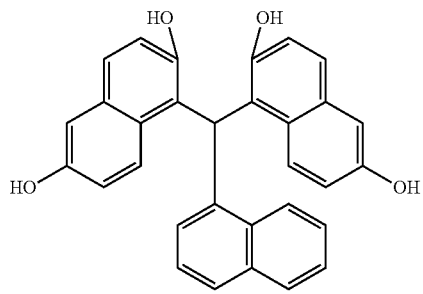

(BisN-7)

Synthesis Example 8

Synthesis of BisN-8 (Polyphenolic Compound)

0.2 g of the objective compound (BisN-8) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 2.06 g (10 mmol) of 9-phenanthrenealdehyde (reagent manufactured by Wako Pure Chemical Industries, Ltd.).

As a result of measuring the molecular weight of the obtained compound by the above method, it was 508.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 255° C. and the glass transition point of 140° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 92]

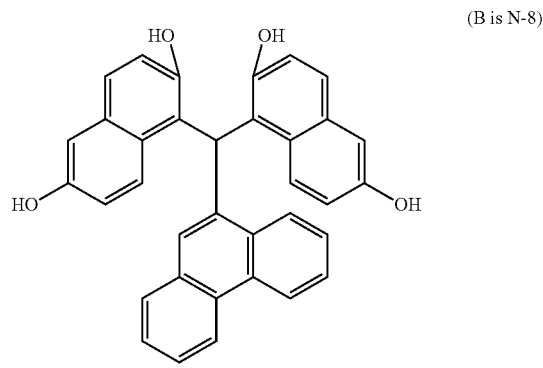

(B is N-8)

Synthesis Example 9

Synthesis of BisN-9 (Polyphenolic Compound)

0.2 g of the objective compound (BisN-9) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 2.30 g (10 mmol) of 1-pyrenealdehyde (reagent manufactured by Sigma-Aldrich Corporation).

As a result of measuring the molecular weight of the obtained compound by the above method, it was 532.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (19H, Ph-H), 6.8 (1H, C—H)

The compound had the thermal decomposition temperature of 260° C. and the glass transition point of 140° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 93]

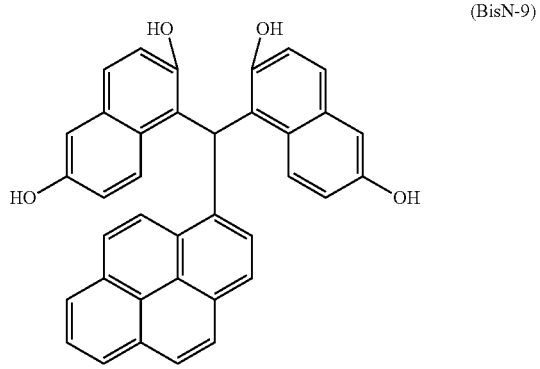

(BisN-9)

Synthesis Example 10

Synthesis of BisN-10 (Polyphenolic Compound)

0.2 g of the objective compound (BisN-10) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 0.98 g (10 mmol) of cyclohexanone (reagent manufactured by Sigma-Aldrich Corporation).

As a result of measuring the molecular weight of the obtained compound by the above method, it was 400.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (10H, Ph-H), 2.1-2.5 (10H, C—H)

The compound had the thermal decomposition temperature of 210° C. and the glass transition point of 100° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 94]

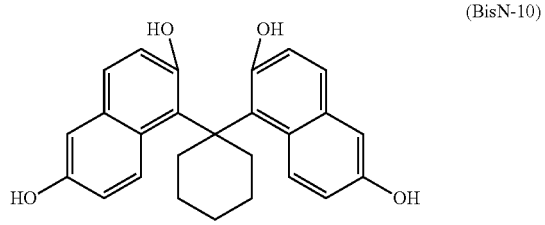

(BisN-10)

Synthesis Example 11

Synthesis of BisN-11 (Polyphenolic Compound)

0.2 g of the objective compound (BisN-11) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 1.80 g (10 mmol) of 9-fluorenone (reagent manufactured by Sigma-Aldrich Corporation).

As a result of measuring the molecular weight of the obtained compound by the above method, it was 482.

The obtained compound was subjected to NMR measurement under the above measurement conditions. The following peaks were found, and the compound was confirmed to have a chemical structure of the following formula.

δ (ppm) 9.3-9.4 (4H, O—H), 7.0-8.1 (18H, Ph-H)

The compound had the thermal decomposition temperature of 250° C. and the glass transition point of 135° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 95]

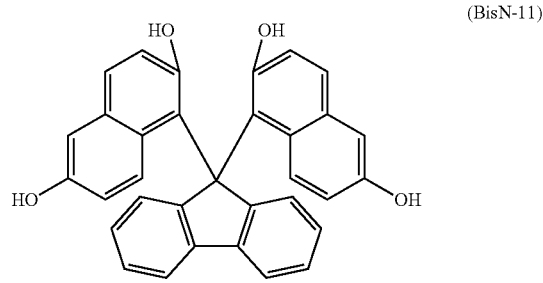

(BisN-11)

Synthesis Example 12

Synthesis of BisN-12 (Polyphenolic Compound)

0.1 g of the objective compound (BisN-12) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 0.67 g (5 mmol) of terephthalaldehyde (reagent manufactured by Sigma-Aldrich Corporation).

As a result of measuring the molecular weight of the obtained compound by the above method, it was 738.

The obtained compound was subjected to NMR measurement under the above measurement conditions. The following peaks were found, and the compound was confirmed to have a chemical structure of the following formula.

δ (ppm) 9.3-9.4 (8H, O—H), 7.0-8.1 (24H, Ph-H), 6.8 (2H, C—H)

The compound had the thermal decomposition temperature of 245° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 96]

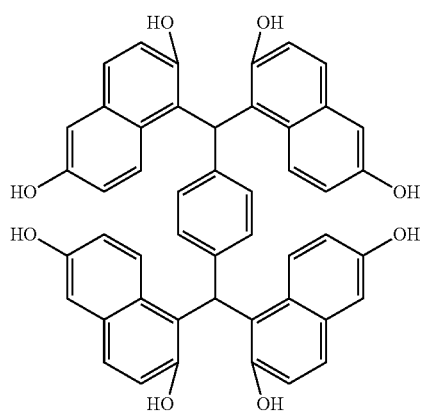

(BisN-12)

Synthesis Example 13

Synthesis of BisN-13 (Polyphenolic Compound)

0.1 g of the objective compound (BisN-13) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 1.05 g (5 mmol) of 4,4'-diformylbiphenyl (reagent manufactured by Sigma-Aldrich Corporation).

As a result of measuring the molecular weight of the obtained compound by the above method, it was 814.

The obtained compound was subjected to NMR measurement under the above measurement conditions. The following peaks were found, and the compound was confirmed to have a chemical structure of the following formula.

δ (ppm) 9.3-9.4 (8H, O—H), 7.0-8.1 (28H, Ph-H), 6.8 (2H, C—H)

The compound had the thermal decomposition temperature of 245° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 97]

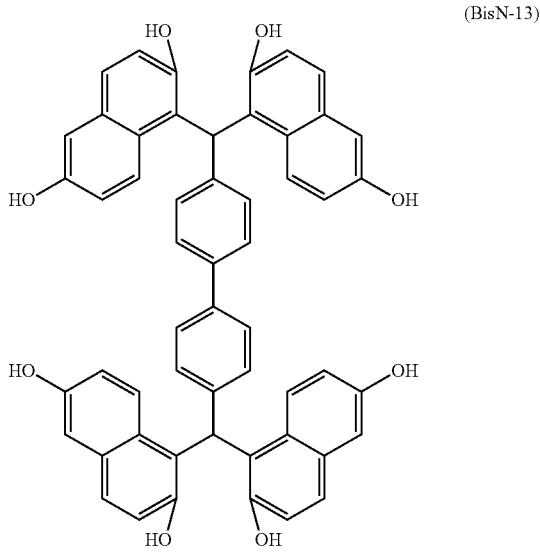

(BisN-13)

Synthesis Example 14

Synthesis of BisN-14 (Polyphenolic Compound)

0.1 g of the objective compound (BisN-14) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 0.53 g (3.3 mmol) of 1,3,5-benzenetricarbaldehyde (reagent manufactured by Mitsubishi Gas Chemical Company, Inc.).

As a result of measuring the molecular weight of the obtained compound by the above method, it was 1068.

The obtained compound was subjected to NMR measurement under the above measurement conditions. The following peaks were found, and the compound was confirmed to have a chemical structure of the following formula.

δ (ppm) 9.3-9.4 (12H, O—H), 7.0-8.1 (33H, Ph-H), 6.8 (3H, C—H)

The compound had the thermal decomposition temperature of 245° C. and the glass transition point of 130° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 98]

(BisN-14)

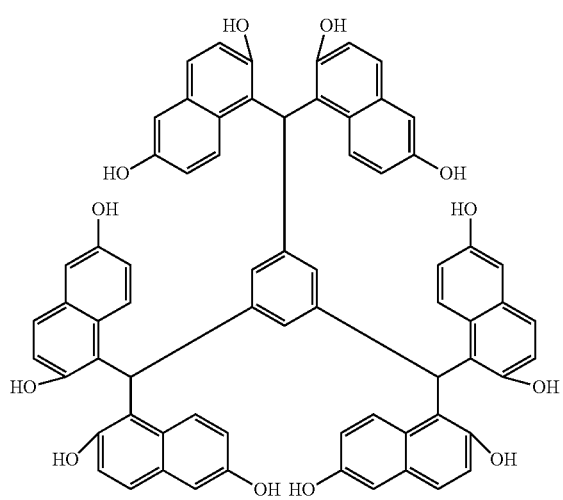

Synthesis Example 15

Synthesis of XBisN-1 (Polyphenolic Compound)

In a container (internal capacity: 100 ml) equipped with a stirrer, a condenser tube, and a burette, 3.20 g (20 mmol) of 2,6-naphthalenediol (reagent manufactured by Sigma-Aldrich Corporation) and 1.82 g (10 mmol) of 4-biphenylcarboxaldehyde (manufactured by Mitsubishi Gas Chemical Company, Inc.) were charged to 30 ml of methyl isobutyl ketone, and 5 ml of 95% sulfuric acid was further added thereto. The reaction solution was stirred at 100° C. for 6 hours to perform reaction. Next, the reaction solution was concentrated. The reaction product was precipitated by the addition of 50 g of pure water. After cooling to room temperature, the precipitates were separated by filtration.

The obtained solid matter was filtered, dried, and then separated and purified by column chromatography to obtain 3.05 g of the objective compound (XBisN-1) represented by the following formula.

As a result of measuring the molecular weight of the obtained compound by the above method, it was 466.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The signals of protons at positions 3 and 4 were found as a doublet, thereby confirming that the substitution position of 2,6-naphthalenediol was position 1.

The compound had the thermal decomposition temperature of 410° C. and the glass transition point of 152° C. and could thereby be confirmed to have high heat resistance.

The solubility in MEK was evaluated by the above method. The compound was evaluated as excellence with evaluation A (50% by weight or more).

The solubility in a safe solvent was further evaluated by the above method. The results are shown in Table 1.

[Chemical Formula 99]

(XBisN-1)

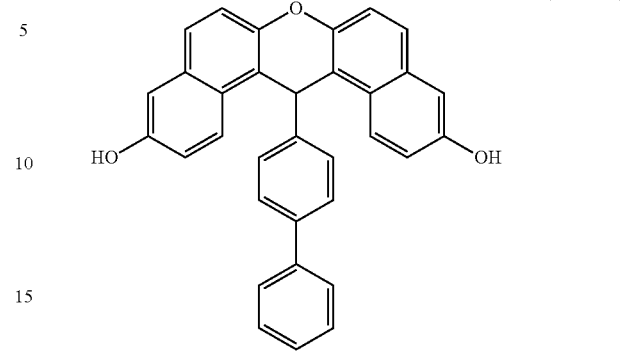

Synthesis Example 16

Synthesis of XBisN-2 (Polyphenolic Compound)

0.2 g of the objective compound (XBisN-2) represented by the following formula was obtained in the same way as in Synthesis Example 15 except that 3.20 g (20 mmol) of 2,6-naphthalenediol was changed to 3.20 g (20 mmol) of 2,7-naphthalenediol (reagent manufactured by Sigma-Aldrich Corporation).

As a result of measuring the molecular weight of the obtained compound by the above method, it was 466.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 100]

(XBisN-2)

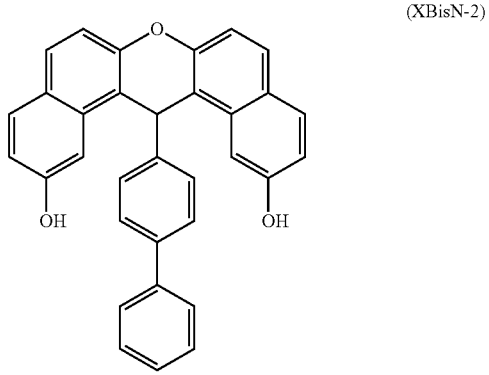

Synthesis Example 17

Synthesis of XBisN-3 (Polyphenolic Compound)

0.2 g of the objective compound (XBisN-3) represented by the following formula was obtained in the same way as in Synthesis Example 15 except that 3.20 g (20 mmol) of 2,6-naphthalenediol was changed to 3.20 g (20 mmol) of 1,5-naphthalenediol (reagent manufactured by Sigma-Aldrich Corporation).

As a result of measuring the molecular weight of the obtained compound by the above method, it was 466.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 101]

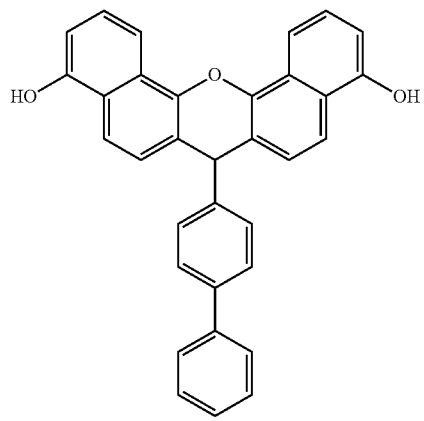

(XBisN-3)

Synthesis Example 18

Synthesis of XBisN-4 (Polyphenolic Compound)

0.2 g of the objective compound (XBisN-4) represented by the following formula was obtained in the same way as in Synthesis Example 15 except that 3.20 g (20 mmol) of 2,6-naphthalenediol was changed to 3.20 g (20 mmol) of 1,6-naphthalenediol (reagent manufactured by Sigma-Aldrich Corporation).

As a result of measuring the molecular weight of the obtained compound by the above method, it was 466.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 102]

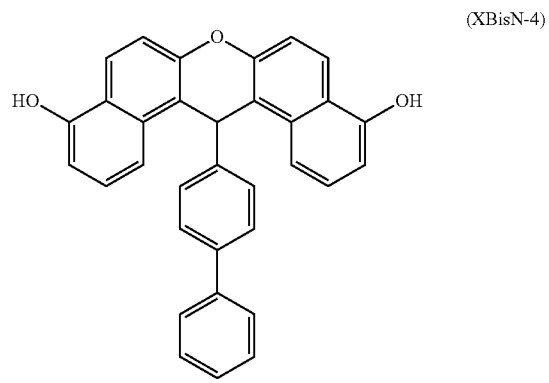

(XBisN-4)

Synthesis Example 19

Synthesis of XBisN-5 (Polyphenolic Compound)

0.2 g of the objective compound (XBisN-5) represented by the following formula was obtained in the same way as in Synthesis Example 15 except that 3.20 g (20 mmol) of 2,6-naphthalenediol was changed to 3.20 g (20 mmol) of 1,7-naphthalenediol (reagent manufactured by Sigma-Aldrich Corporation).

As a result of measuring the molecular weight of the obtained compound by the above method, it was 466.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 103]

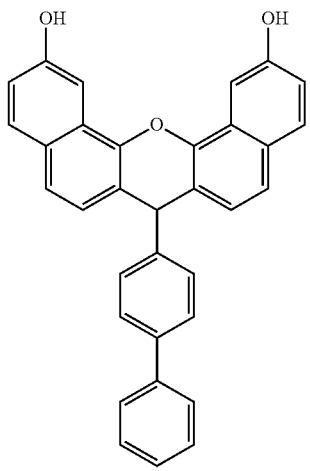

(XBisN-5)

Synthesis Example 20

Synthesis of XBisN-6 (Polyphenolic Compound)

0.2 g of the objective compound (XBisN-6) represented by the following formula was obtained in the same way as in Synthesis Example 15 except that 3.20 g (20 mmol) of 2,6-naphthalenediol was changed to 3.20 g (20 mmol) of 2,3-naphthalenediol (reagent manufactured by Sigma-Aldrich Corporation).

As a result of measuring the molecular weight of the obtained compound by the above method, it was 466.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 104]

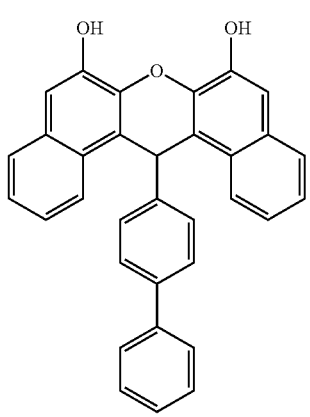

(XBisN-6)

Synthesis Example 21

Synthesis of XBisN-7 (Polyphenolic Compound)

0.2 g of the objective compound (XBisN-7) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 1.56 g (10 mmol) of 1-naphthaldehyde (reagent manufactured by Sigma-Aldrich Corporation).

As a result of measuring the molecular weight of the obtained compound by the above method, it was 440.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (17H, Ph-H), 6.6 (1H, C—H)

The compound had the thermal decomposition temperature of 415° C. and the glass transition point of 155° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 105]

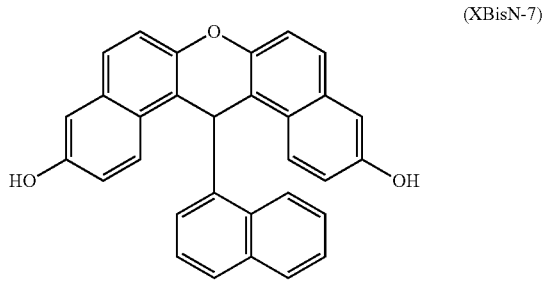

(XBisN-7)

Synthesis Example 22

Synthesis of XBisN-8 (Polyphenolic Compound)

0.2 g of the objective compound (XBisN-8) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 2.06 g (10 mmol) of 9-phenanthrenealdehyde (reagent manufactured by Wako Pure Chemical Industries, Ltd.).

As a result of measuring the molecular weight of the obtained compound by the above method, it was 490.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 415° C. and the glass transition point of 155° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 106]

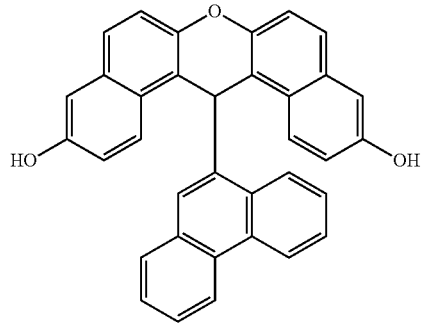

(XBisN-8)

Synthesis Example 23

Synthesis of XBisN-9 (Polyphenolic Compound)

0.2 g of the objective compound (XBisN-9) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 2.30 g (10 mmol) of 1-pyrenealdehyde (reagent manufactured by Sigma-Aldrich Corporation).

As a result of measuring the molecular weight of the obtained compound by the above method, it was 514.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (19H, Ph-H), 6.6 (1H, C—H)

The compound had the thermal decomposition temperature of 420° C. and the glass transition point of 155° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 107]

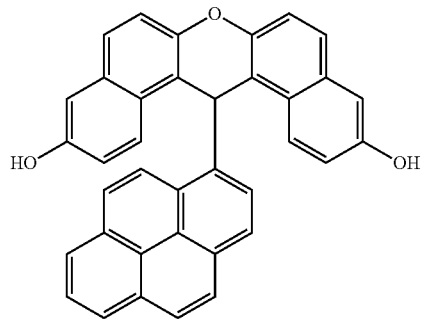

(XBisN-9)

Synthesis Example 24

Synthesis of XBisN-10 (Polyphenolic Compound)

0.2 g of the objective compound (XBisN-10) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 0.98 g (10 mmol) of cyclohexanone (reagent manufactured by Sigma-Aldrich Corporation).

As a result of measuring the molecular weight of the obtained compound by the above method, it was 382.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (10H, Ph-H), 2.1-2.5 (10H, C—H)

The compound had the thermal decomposition temperature of 400° C. and the glass transition point of 140° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 108]

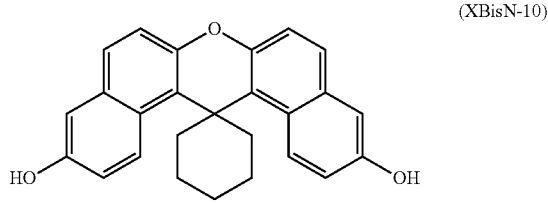

(XBisN-10)

Synthesis Example 25

Synthesis of XBisN-11 (Polyphenolic Compound)

0.2 g of the objective compound (XBisN-11) represented by the following formula was obtained in the same way as in Synthesis Example 1 except that 1.82 g (10 mmol) of 4-biphenylcarboxaldehyde (manufactured by Mitsubishi Gas Chemical Company, Inc.) was changed to 1.80 g (10 mmol) of 9-fluorenone (reagent manufactured by Sigma-Aldrich Corporation).

As a result of measuring the molecular weight of the obtained compound by the above method, it was 464.

The obtained compound was subjected to NMR measurement under the above measurement conditions. The following peaks were found, and the compound was confirmed to have a chemical structure of the following formula.

δ (ppm) 9.7 (2H, O—H), 7.2-8.5 (18H, Ph-H)

The compound had the thermal decomposition temperature of 450° C. and the glass transition point of 145° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 109]

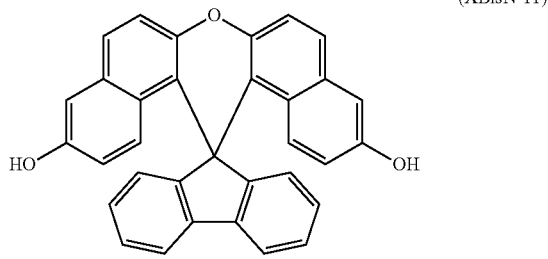

(XBisN-11)

Synthesis Example 26

Synthesis of XBisN-12 (Polyphenolic Compound)

0.1 g of the objective compound (XBisN-12) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 0.67 g (5 mmol) of terephthalaldehyde (reagent manufactured by Sigma-Aldrich Corporation).

As a result of measuring the molecular weight of the obtained compound by the above method, it was 702.

The obtained compound was subjected to NMR measurement under the above measurement conditions. The following peaks were found, and the compound was confirmed to have a chemical structure of the following formula.

δ (ppm) 9.7 (4H, O—H), 7.2-8.5 (24H, Ph-H), 6.6 (2H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 110]

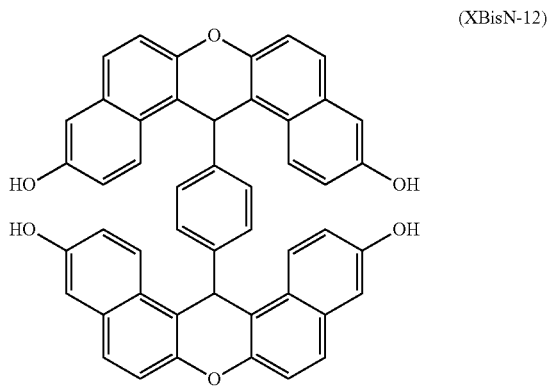

(XBisN-12)

Synthesis Example 27

Synthesis of XBisN-13 (Polyphenolic Compound)

0.1 g of the objective compound (XBisN-13) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 1.05 g (5 mmol) of 4,4'-diformylbiphenyl (reagent manufactured by Sigma-Aldrich Corporation).

As a result of measuring the molecular weight of the obtained compound by the above method, it was 778.

The obtained compound was subjected to NMR measurement under the above measurement conditions. The following peaks were found, and the compound was confirmed to have a chemical structure of the following formula.

δ (ppm) 9.7 (4H, O—H), 7.2-8.5 (28H, Ph-H), 6.6 (2H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 111]

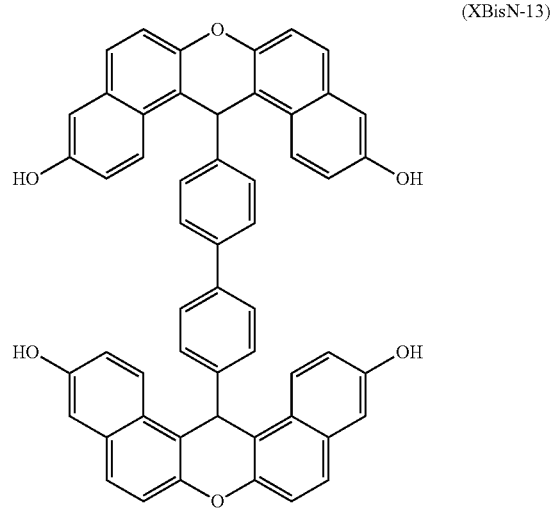

(XBisN-13)

Synthesis Example 28

Synthesis of XBisN-14 (Polyphenolic Compound)

0.1 g of the objective compound (XBisN-14) represented by the following formula was obtained in the same way as in Synthesis Example 15 except that 1.82 g (10 mmol) of 4-biphenylcarboxaldehyde (manufactured by Mitsubishi Gas Chemical Company, Inc.) was changed to 0.53 g (3.3 mmol) of 1,3,5-benzenetricarbaldehyde (reagent manufactured by Mitsubishi Gas Chemical Company, Inc.).

As a result of measuring the molecular weight of the obtained compound by the above method, it was 1014.

The obtained compound was subjected to NMR measurement under the above measurement conditions. The following peaks were found, and the compound was confirmed to have a chemical structure of the following formula.

δ (ppm) 9.7 (6H, O—H), 7.2-8.5 (33H, Ph-H), 6.6 (3H, C—H)

The compound had the thermal decomposition temperature of 410° C. and the glass transition point of 152° C. and could thereby be confirmed to have high heat resistance.

The solubility in MEK was evaluated by the above method. The compound was evaluated as goodness with evaluation B (10% by weight or more and less than 50% by weight).

The solubility in a safe solvent was further evaluated by the above method. The results are shown in Table 1.

[Chemical Formula 112]

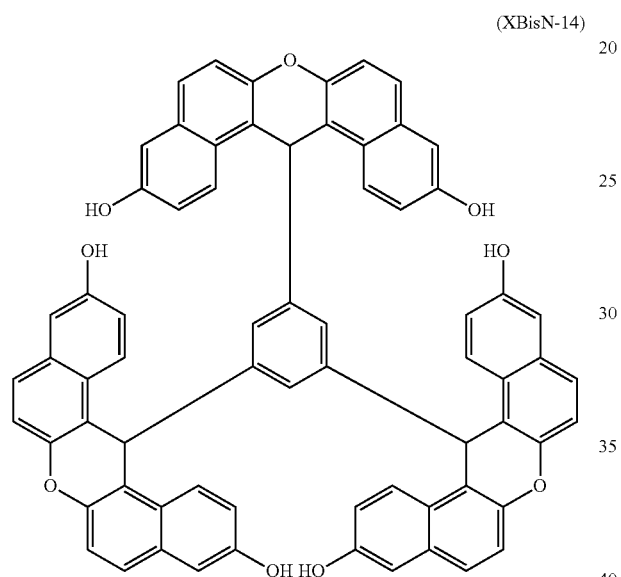

(XBisN-14)

Synthesis Comparative Example 1

Synthesis of TetP-1 (Polyphenolic Compound)

In a four necked flask (1000 ml) sufficiently dried, substituted with nitrogen, and equipped with a dropping funnel, a Dimroth condenser tube, a thermometer, and a stirring blade, 108.8 g/0.8 mol of 2,3,6-trimethylphenol manufactured by Honshu Chemical Industry Co., Ltd. and 18.4 g/0.1 mol of 2,7-naphthalenedicarboxaldehyde manufactured by Mitsubishi Gas Chemical Company, Inc. were mixed under a nitrogen gas stream, and dissolved by heating to about 60° C. Then, 0.1 ml of sulfuric acid, 0.8 ml of 3-mercaptopropionic acid, and 10 ml of toluene were added, and the mixture was reacted while stirring.

After the reaction terminated, it was stood to cool, and after it reached room temperature, it was cooled in an ice bath. It was left at rest for 1 hour, to produce a target light yellow crude crystal, which was filtered. Subsequently, the crude crystal was washed with warm water of 60° C. by stirring and recrystallized to obtain 8.99 g of the objective product (TetP-1) represented by the following formula.

The obtained compound was subjected to NMR measurement under the above measurement conditions and thereby confirmed to have a chemical structure of the following formula.

Also, the solubility in a safe solvent was evaluated by the above method. The results are shown in Table 1.

[Chemical Formula 113]

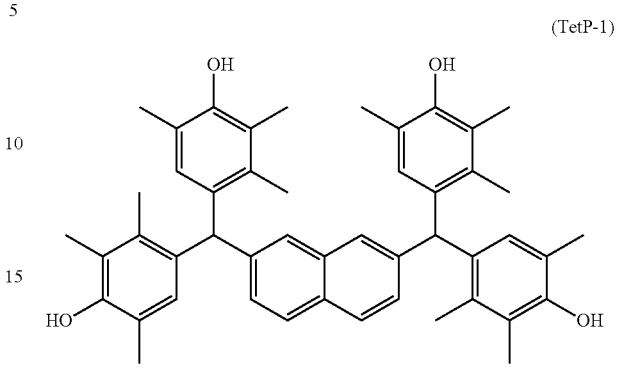

(TetP-1)

Synthesis Comparative Example 2

Synthesis of CR-1 (Polyphenolic Compound)

74.3 g (3.71 mol) of anhydrous HF and 50.5 g (0.744 mol) of BF₃ were charged into a temperature-controllable autoclave (made of SUS316L) having an internal capacity of 500 ml and equipped with an electromagnetic stirring device, and the content was stirred and increased in pressure with carbon monoxide to 2 MPa while maintaining the liquid temperature to −30° C. Thereafter, while maintaining the pressure to 2 MPa and the liquid temperature to −30° C., a raw material obtained by mixing 57.0 g (0.248 mol) of 4-cyclohexylbenzene and 50.0 g of n-heptane was fed thereto. After maintaining the content for 1 hour, the content was collected into ice, diluted with benzene, and neutralized to provide an oily layer, which was analyzed by gas chromatograph for evaluating the reaction performance. The 4-cyclohexylbenzene conversion was 100%, and the 4-cyclohexylbenzaldehyde selectivity was 97.3%.

The target component was isolated by simple distillation and analyzed by GC-MS, and the result exhibited a molecular weight of 188 corresponding to the molecular weight of 4-cyclohexylbenzaldehyde (CHBAL) as the following formula. The chemical shift value of ¹H-NMR in a deuterated chloroform solvent (δ ppm, TMS standard) was 1.0 to 1.6 (m, 10H), 2.6 (m, 1H), 7.4 (d, 2H), 7.8 (d, 2H), and 10.0 (s, 1H).

The obtained compound was subjected to NMR measurement under the above measurement conditions and thereby confirmed to have a chemical structure of the following formula.

Also, the solubility in a safe solvent was evaluated by the above method. The results are shown in Table 1.

[Chemical Formula 114]

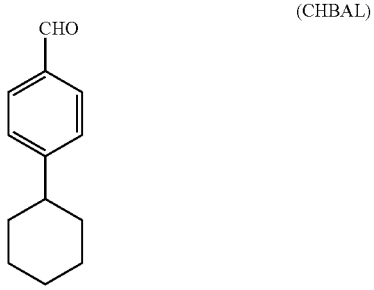

(CHBAL)

Under a nitrogen gas stream, resorcinol manufactured by Kanto Chemical Co., Inc. (22 g, 0.2 mol), the above 4-cyclohexylbenzaldehyde (46.0 g, 0.2 mol), and dehydrated ethanol (200 ml) were charged to a four necked flask (1000 ml) sufficiently dried, substituted with nitrogen, and equipped with a dropping funnel, a Dimroth condenser tube, a thermometer, and a stirring blade, to prepare an ethanol solution. This solution was heated to 85° C. by a mantle heater while stirring. Then, 75 ml of concentrated hydrochloric acid (35%) was dropped through the dropping funnel for 30 minutes, and continuously stirred at 85° C. for 3 hours. After the reaction terminated, it was stood to cool, and after it reached room temperature, it was cooled in an ice bath. It was left at rest for 1 hour, to produce a target light yellow crude crystal, which was filtered. The crude crystal was washed twice with 500 ml of methanol, filtered, and dried in a vacuum to obtain 50 g of the product (CR-1A) represented by the following formula.

The result of LC-MS analysis for the product exhibited a molecular weight of 1121. The chemical shift value (δ ppm, TMS standard) of $^1$H-NMR in a deuterated chloroform solvent was 0.8 to 1.9 (m, 44H), 5.5 to 5.6 (d, 4H), 6.0 to 6.8 (m, 24H), and 8.4 to 8.5 (m, 8H). From these results, the obtained product was identified as an objective compound (CR-1) (yield: 91%).

[Chemical Formula 115]

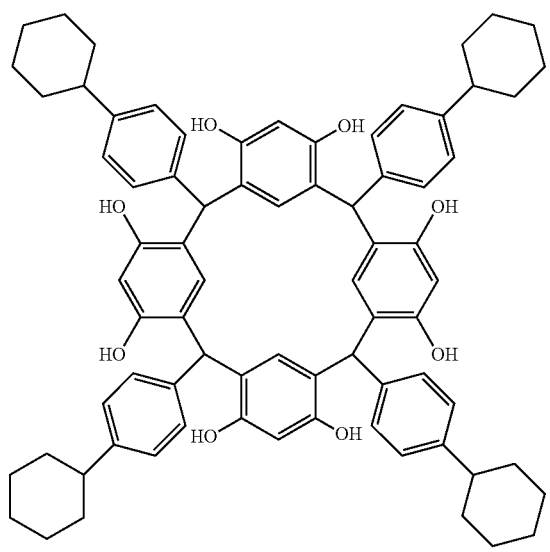

(CR-1)

Also, the solubility in a safe solvent was evaluated by the above method. The results are shown in Table 1.

EXAMPLES AND COMPARATIVE EXAMPLES

Examples 1 to 28 and Comparative Examples 1 and 2

Synthesis of Resist Composition

Resist compositions having formulations shown in Table 2 were prepared as Examples 1 to 14 using Synthesis Examples 1 to 14, Examples 15 to 28 using Synthesis Examples 15 to 28, Comparative Example 1 using Synthesis Comparative Example 1, and Comparative Example 2 using Synthesis Comparative Example 2.

Of the components in Table 2, as the acid generating agent (C), the acid crosslinking agent (G), the acid diffusion controlling agent (E), and the solvent, the followings were used:
Acid Generating Agent (C)
P-1: triphenylbenzenesulfonium trifluoromethanesulfonate (Midori Kagaku Co., Ltd.)
Acid Crosslinking Agent (G)
C-1: NIKALAC MW-100LM (Sanwa Chemical Co., Ltd.)
Acid Diffusion Controlling Agent (E)
Q-1: trioctylamine (Tokyo Kasei Kogyo Co., Ltd.) Solvent
S-1: propylene glycol monomethyl ether (Tokyo Kasei Kogyo Co., Ltd.)

The heat resistance of the obtained compositions was evaluated by the above method. The obtained results are shown in Table 2.

Resist patterns were formed using the obtained resist compositions according to the following procedures. A clean silicon wafer was spin coated with a resist composition, and then prebaked (PB) before exposure in an oven of 110° C. to form a resist film with a thickness of 60 nm. The obtained resist film was irradiated with electron beams of 1:1 line and space setting with a 50 nm interval, a 40 nm interval, and a 30 nm interval using an electron beam lithography system (ELS-7500 manufactured by ELIONIX INC.). After irradiation, it was heated at each predetermined temperature for 90 seconds, and immersed in 2.38% by weight TMAH alkaline developing solution for 60 seconds for development. Subsequently, it was washed with ultrapure water for 30 seconds, and dried to form a negative type resist pattern.

Pattern evaluation was carried out for the obtained resist patterns according to the above method. The obtained results are shown in Table 2.

As is evident from Table 2, the films from the resists of Examples were all confirmed to be good films having no defect and have good heat resistance (evaluation: ○ (good)).

As is evident from Table 1, in the resists of Examples 1 to 28, resist patterns with good resolution of 30 nm and good sensitivity could be obtained. The roughness of the patterns was also small, and their shapes were also good.

On the other hand, in the resists of Comparative Examples 1 and 2, resist patterns with good resolution of 40 nm could be obtained, however, a resist pattern with resolution of 30 nm could not be obtained.

Example 29

Synthesis of Alcoholic Compound

In a container (internal capacity: 100 ml) equipped with a stirrer, a condenser tube, and a burette, 10 g (21 mmol) of the above XBisN-1 of (Synthesis Example 15) and 14.8 g (107 mmol) of potassium carbonate were charged to 50 ml of dimethylformamide, and 6.56 g (54 mmol) of acetic acid-2-chloroethyl was further added thereto. The reaction solution was stirred at 90° C. for 12 hours to perform reaction. Next, the reaction solution was cooled in an ice bath to precipitate a crystal, which was separated by filtration. Subsequently, 40 g of the crystal, 40 g of methanol, 100 g of THF, and 24% aqueous sodium hydroxide solution were charged to a container (internal capacity: 100 ml) equipped with a stirrer, a condenser tube, and a burette. The reaction solution was stirred for 4 hours under reflux to perform reaction. Subsequently, the reaction solution was cooled in an ice bath and concentrated. The precipitated solid matter was filtered, dried, and then separated and purified by column chromatography to obtain 5.9 g of the objective compound represented by the following formula (7').

The obtained compound was subjected to NMR measurement under the above measurement conditions. The following peaks were found, and the compound was confirmed to have a chemical structure of the following formula (7').

δ (ppm) 8.6 (2H, O—H), 7.2-7.8 (19H, Ph-H), 6.7 (1H, C—H), 4.0 (4H, —O—C$\underline{H}_2$—), 3.8 (4H, —C$\underline{H}_2$—OH)

The compound had the thermal decomposition temperature of 375° C., the glass transition point of 132° C., and the melting point of 256° C. and could thereby be confirmed to have high heat resistance.

[Chemical Formula 116]

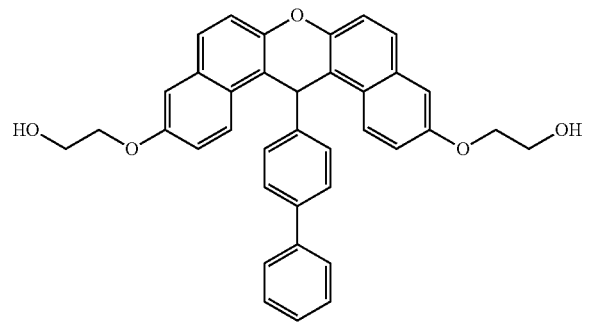

(7')

TABLE 1

| | Polyphenolic compound | Solubility test of compound in safe solvent | |
|---|---|---|---|
| | | PGME | PGMEA |
| Synthesis Example 1 | BisN-1 | A | A |
| Synthesis Example 2 | BisN-2 | A | A |
| Synthesis Example 3 | BisN-3 | A | A |
| Synthesis Example 4 | BisN-4 | A | A |
| Synthesis Example 5 | BisN-5 | A | A |
| Synthesis Example 6 | BisN-6 | A | A |
| Synthesis Example 7 | BisN-7 | A | A |
| Synthesis Example 8 | BisN-8 | A | A |
| Synthesis Example 9 | BisN-9 | A | A |
| Synthesis Example 10 | BisN-10 | A | A |
| Synthesis Example 11 | BisN-11 | A | A |
| Synthesis Example 12 | BisN-12 | A | A |
| Synthesis Example 13 | BisN-13 | A | A |
| Synthesis Example 14 | BisN-14 | A | A |
| Synthesis Example 15 | XBisN-1 | A | A |
| Synthesis Example 16 | XBisN-2 | A | A |
| Synthesis Example 17 | XBisN-3 | A | A |
| Synthesis Example 18 | XBisN-4 | A | A |
| Synthesis Example 19 | XBisN-5 | A | A |
| Synthesis Example 20 | XBisN-6 | A | A |
| Synthesis Example 21 | XBisN-7 | A | A |
| Synthesis Example 22 | XBisN-8 | A | A |
| Synthesis Example 23 | XBisN-9 | A | A |
| Synthesis Example 24 | XBisN-10 | A | A |
| Synthesis Example 25 | XBisN-11 | A | A |
| Synthesis Example 26 | XBisN-12 | A | A |
| Synthesis Example 27 | XBisN-13 | A | A |
| Synthesis Example 28 | XBisN-14 | A | A |
| Synthesis Comparative Example 1 | TetP-1 | A | A |
| Synthesis Comparative Example 2 | CR-1 | B | C |

TABLE 2

| | | Resist performance evaluation | | | | | | |
|---|---|---|---|---|---|---|---|---|
| | | Resist composition | | | | | | |
| | Polyphenolic compound | Compound of Synthesis Example [g] | Acid generating agent (C) P-1 [g] | Acid crosslinking agent (G) C-1 [g] | Acid diffusion controlling agent (E) Q-1 [g] | Solvent S-1 [g] | Heat resistance evaluation | Pattern evaluation |
| Example 1 | BisN-1 | 1.0 | 0.3 | 0.3 | 0.03 | 30.0 | ○ | ○ |
| Example 2 | BisN-2 | 1.0 | 0.3 | 0.3 | 0.03 | 30.0 | ○ | ○ |
| Example 3 | BisN-3 | 1.0 | 0.3 | 0.3 | 0.03 | 30.0 | ○ | ○ |
| Example 4 | BisN-4 | 1.0 | 0.3 | 0.3 | 0.03 | 30.0 | ○ | ○ |
| Example 5 | BisN-5 | 1.0 | 0.3 | 0.3 | 0.03 | 30.0 | ○ | ○ |
| Example 6 | BisN-6 | 1.0 | 0.3 | 0.3 | 0.03 | 30.0 | ○ | ○ |
| Example 7 | BisN-7 | 1.0 | 0.3 | 0.3 | 0.03 | 30.0 | ○ | ○ |
| Example 8 | BisN-8 | 1.0 | 0.3 | 0.3 | 0.03 | 30.0 | ○ | ○ |
| Example 9 | BisN-9 | 1.0 | 0.3 | 0.3 | 0.03 | 30.0 | ○ | ○ |
| Example 10 | BisN-10 | 1.0 | 0.3 | 0.3 | 0.03 | 30.0 | ○ | ○ |
| Example 11 | BisN-11 | 1.0 | 0.3 | 0.3 | 0.03 | 30.0 | ○ | ○ |
| Example 12 | BisN-12 | 1.0 | 0.3 | 0.3 | 0.03 | 30.0 | ○ | ○ |
| Example 13 | BisN-13 | 1.0 | 0.3 | 0.3 | 0.03 | 30.0 | ○ | ○ |
| Example 14 | BisN-14 | 1.0 | 0.3 | 0.3 | 0.03 | 30.0 | ○ | ○ |
| Example 15 | XBisN-1 | 1.0 | 0.3 | 0.3 | 0.03 | 30.0 | ○ | ○ |
| Example 16 | XBisN-2 | 1.0 | 0.3 | 0.3 | 0.03 | 30.0 | ○ | ○ |
| Example 17 | XBisN-3 | 1.0 | 0.3 | 0.3 | 0.03 | 30.0 | ○ | ○ |
| Example 18 | XBisN-4 | 1.0 | 0.3 | 0.3 | 0.03 | 30.0 | ○ | ○ |
| Example 19 | XBisN-5 | 1.0 | 0.3 | 0.3 | 0.03 | 30.0 | ○ | ○ |
| Example 20 | XBisN-6 | 1.0 | 0.3 | 0.3 | 0.03 | 30.0 | ○ | ○ |
| Example 21 | XBisN-7 | 1.0 | 0.3 | 0.3 | 0.03 | 30.0 | ○ | ○ |
| Example 22 | XBisN-8 | 1.0 | 0.3 | 0.3 | 0.03 | 30.0 | ○ | ○ |
| Example 23 | XBisN-9 | 1.0 | 0.3 | 0.3 | 0.03 | 30.0 | ○ | ○ |
| Example 24 | XBisN-10 | 1.0 | 0.3 | 0.3 | 0.03 | 30.0 | ○ | ○ |
| Example 25 | XBisN-11 | 1.0 | 0.3 | 0.3 | 0.03 | 30.0 | ○ | ○ |
| Example 26 | XBisN-12 | 1.0 | 0.3 | 0.3 | 0.03 | 30.0 | ○ | ○ |

TABLE 2-continued

| | Polyphenolic compound | Compound of Synthesis Example [g] | Resist composition | | | | Resist performance evaluation | |
|---|---|---|---|---|---|---|---|---|
| | | | Acid generating agent (C) P-1 [g] | Acid crosslinking agent (G) C-1 [g] | Acid diffusion controlling agent (E) Q-1 [g] | Solvent S-1 [g] | Heat resistance evaluation | Pattern evaluation |
| Example 27 | XBisN-13 | 1.0 | 0.3 | 0.3 | 0.03 | 30.0 | ○ | ○ |
| Example 28 | XBisN-14 | 1.0 | 0.3 | 0.3 | 0.03 | 30.0 | ○ | ○ |
| Comparative Example 1 | TetP-1 | 1.0 | 0.3 | 0.3 | 0.03 | 30.0 | ○ | x |
| Comparative Example 2 | CR-1 | 1.0 | 0.3 | 0.3 | 0.03 | 30.0 | ○ | x |

As seen in the above results, the resist composition containing the compound (BisN-1) of the present invention has higher sensitivity than that of the composition containing the comparative compound (TetP-1) or (CR-1), and enables the formation of the resist pattern having a better shape and having smaller roughness. As long as the requirements of the above present invention are met, compounds other than those described in examples also exhibit the same effects.

This application claims the priority based on Japanese Patent Application No. 2011-176923 filed with JPO on Aug. 12, 2011, Japanese Patent Application No. 2011-201757 filed with JPO on Sep. 15, 2011, and Japanese Patent Application No. 2011-218626 filed with JPO on Sep. 30, 2011, the entire contents of which are hereby incorporated by reference.

INDUSTRIAL APPLICABILITY

The present invention can provide a resist composition which is excellent in heat resistance, has high solubility in a safe solvent, has high sensitivity, and can impart a good shape to a resist pattern, and a method for forming a resist pattern using the composition. Thus, the resist composition of the present invention is useful in the fields of semiconductors, displays, photomasks, thin film magnetic heads, compound semiconductors, and research and development, or the like in which resist compositions such as acid amplification type non-polymer based resist materials are used.

The present invention can also provide a polyphenolic compound which is excellent in heat resistance and has high solubility in a safe solvent. Thus, the polyphenolic compound of the present invention is preferably used in base materials for photosensitive materials such as photoresists for semiconductors, raw materials for epoxy resins or curing agents used in sealing materials or the like of integrated circuits, developers or discoloration preventing agents used in thermal recording materials, and other additives such as germicides and antifungal and antibacterial agents, and the like.

The present invention can provide an alcoholic compound which has high heat resistance. Thus, the alcoholic compound of the present invention is useful as raw materials for light curing or thermosetting resins such as epoxy resins or acrylic resins (di(meth)acrylate, etc.), thermoplastic resins such as polyester, polycarbonate, and polyurethane, or as epoxy resin curing agents.

The invention claimed is:

1. A compound represented by formula (1) or formula (2):

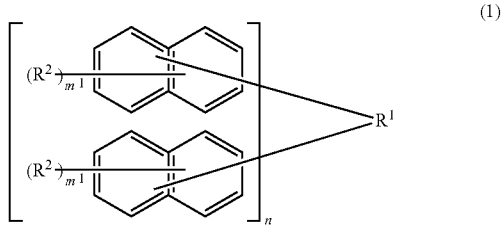

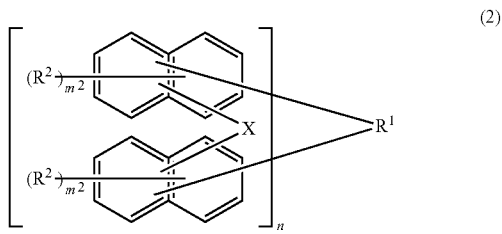

wherein $R^1$ are each independently a single bond or a 2n-valent hydrocarbon group having 1 to 30 carbon atoms wherein the hydrocarbon group may have a cyclic hydrocarbon group, a double bond, a heteroatom, or an aromatic group having 6 to 30 carbon atoms;

$R^2$ are each independently a hydrogen atom, a halogen atom, a linear, branched, or cyclic alkyl group having 1 to 10 carbon atoms, an aryl group having 6 to 10 carbon atoms, an alkenyl group having 2 to 10 carbon atoms, or a hydroxyl group and may be the same or different on the same naphthalene ring;

at least two of $R^2$ on at least one of the naphthalene moieties is a hydroxyl group in the formula (1);

at least one of $R^2$ is a hydroxyl group in the formula (2);

n is an integer of 2 to 4;

the structural formulas of the repeating units in the formulas (1) and (2) may be the same or different;

in the formula (1), $m^1$ are each independently an integer of 1 to 7; and in the formula (2), X are each independently an oxygen atom or a sulfur atom, and $m^2$ are each independently an integer of 1 to 6.

2. The compound according to claim 1, wherein the formula (1) is the general formula (1-1), and the formula (2) is the formula (2-1):

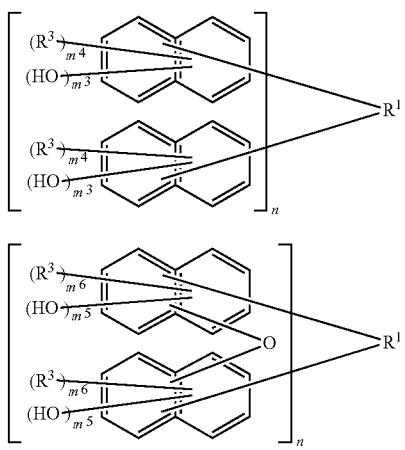

(1-1)

(2-1)

wherein $R^1$ are each independently a single bond or a 2n-valent hydrocarbon group having 1 to 30 carbon atoms wherein the hydrocarbon group may have a cyclic hydrocarbon group, a double bond, a heteroatom, or an aromatic group having 6 to 30 carbon atoms;

$R^3$ are each independently a hydrogen atom, a linear, branched, or cyclic alkyl group having 1 to 10 carbon atoms, an aryl group having 6 to 10 carbon atoms, or an alkenyl group having 2 to 10 carbon atoms and may be the same or different on the same naphthalene ring;

the structural formulas of the repeating units in the formulas (1-1) and (2-1) may be the same or different;

n is an integer of 2 to 4; in the formula (1-1), $m^3$ are each independently an integer of 2 to 7, $m^4$ are each independently an integer of 0 to 6, and $m^3+m^4$ is an integer of 2 to 7; and in the formula (2-1), $m^5$ are each independently an integer of 1 to 6, $m^6$ are each independently an integer of 0 to 5, and $m^5+m^6$ is an integer of 1 to 6.

3. The compound according to 1, wherein the formula (2) is the formula (2-2):

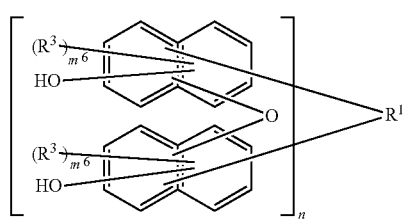

(2-2)

wherein $R^1$ is a single bond or a 2n-valent hydrocarbon group having 1 to 30 carbon atoms wherein the hydrocarbon group may have a cyclic hydrocarbon group, a double bond, a heteroatom, or an aromatic group having 6 to 30 carbon atoms;

$R^3$ are each independently a hydrogen atom, a linear, branched, or cyclic alkyl group having 1 to 10 carbon atoms, an aryl group having 6 to 10 carbon atoms, or an alkenyl group having 2 to 10 carbon atoms and may be the same or different on the same naphthalene ring;

the structural formulas of the repeating units in the formula (2-2) may be the same or different;

n is an integer of 2 to 4; and in the formula (2-2), $m^6$ are each independently an integer of 0 to 5.

* * * * *